US009708306B2

United States Patent
Ge et al.

(10) Patent No.: US 9,708,306 B2
(45) Date of Patent: Jul. 18, 2017

(54) BENZIMIDAZOLE DERIVATIVES AND PREPARATION PROCESS AND PHARMACEUTICAL USES THEREOF

(71) Applicants: WUHAN LL SCIENCE AND TECHNOLOGY DEVELOPMENT CO., LTD, Wuhan, Hubei (CN); WUHAN QR PHARMACEUTICALS CO., LTD, Wuhan, Hubei (CN)

(72) Inventors: Jian Ge, Hubei (CN); Jianyi Ma, Hubei (CN); Guangya Xiang, Hubei (CN); Wei Wang, Hubei (CN); Chaodong Wang, Hubei (CN)

(73) Assignees: WUHAN LL SCIENCE AND TECHNOLOGY DEVELOPMENT CO., LTD, Wuhan, Hubei (CN); WUHAN QR PHARMACEUTICALS CO., LTD, Wuhan, Hubei (CN)

( * ) Notice: Subject to any disclaimer, the term of this patent is extended or adjusted under 35 U.S.C. 154(b) by 0 days.

(21) Appl. No.: 15/123,961

(22) PCT Filed: Mar. 18, 2015

(86) PCT No.: PCT/CN2015/074426
§ 371 (c)(1),
(2) Date: Sep. 6, 2016

(87) PCT Pub. No.: WO2016/145622
PCT Pub. Date: Sep. 22, 2016

(65) Prior Publication Data
US 2017/0022188 A1  Jan. 26, 2017

(51) Int. Cl.
*C07D 413/10* (2006.01)
*A61K 31/4245* (2006.01)
(Continued)

(52) U.S. Cl.
CPC ........ *C07D 413/10* (2013.01); *A61K 31/4245* (2013.01); *A61K 31/497* (2013.01);
(Continued)

(58) Field of Classification Search
None
See application file for complete search history.

(56) References Cited

U.S. PATENT DOCUMENTS 5,583,141 A    12/1996  Naka et al.
2014/0113942 A1  4/2014  Dwivedi et al.

FOREIGN PATENT DOCUMENTS

CN    1079966 A    12/1993
CN    1946717 A     4/2007
(Continued)

OTHER PUBLICATIONS

Kirk-Othmer Encyclopedia of Chemical Technology Copyright © 2002 by John Wiley & Sons, Inc., pp. 95-147, Article Online Posting Date: Aug. 16, 2002.*

(Continued)

*Primary Examiner* — Karl J Puttlitz
(74) *Attorney, Agent, or Firm* — Novick, Kim & Lee, PLLC; Allen Xue

(57) ABSTRACT

The invention belongs to the technical field of pharmaceutical chemistry, and particularly pertains to benzimidazole derivatives, and preparation process and pharmaceutical uses thereof. Benzimidazole derivatives include Ligustrazine and NO donor derivatives. The kind of the compounds can rapidly release Ligustrazine or No in vivo, so that they can produce effective synergetic effects with Azilsartan, to enhance the anti-hypertension effect, and reduce adverse effects, and the released Ligustrazine can produce ideal protection to patients' livers and kidneys, thereby filling blanks in the prior art.

22 Claims, 3 Drawing Sheets

Figure 1:
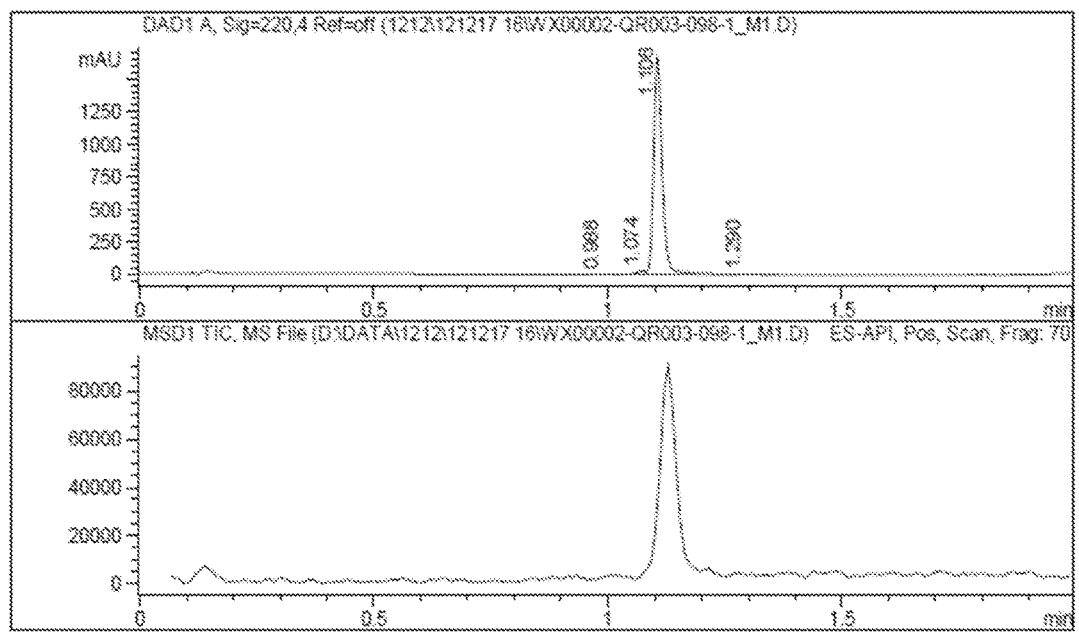

(51) Int. Cl.
    *A61K 31/497*  (2006.01)
    *A61K 31/501*  (2006.01)
    *C07D 403/14*  (2006.01)
    *C07D 493/04*  (2006.01)
    *C07D 498/18*  (2006.01)
    *C07D 413/14*  (2006.01)
(52) U.S. Cl.
    CPC .......... *A61K 31/501* (2013.01); *C07D 403/14*
        (2013.01); *C07D 413/14* (2013.01); ***C07D
        493/04* (2013.01); *C07D 498/18*** (2013.01)

(56) References Cited

FOREIGN PATENT DOCUMENTS

| CN | 102351853 A | | 2/2012 |
| CN | 103709154 | * | 4/2014 |
| CN | 103709154 A | | 4/2014 |
| CN | 104774196 A | | 7/2015 |
| CN | 104774197 A | | 7/2015 |
| WO | 2012090043 A1 | | 7/2012 |
| WO | 2012107814 A1 | | 8/2012 |
| WO | 2014080365 A1 | | 4/2014 |

OTHER PUBLICATIONS

Rouhi, "The Right Stuff, from research and development to the clinic, getting drug crystals right is full of pitfalls", Chemical & Engineering News, Feb. 24, 2003, pp. 32-35.*

"Crystallization and Precipitation" in Ullmann's Encyclopedia of Industrial Chemistry, Copyright © 2002 by Wiley-VCH Verlag GmbH & Co. KGaA , pp. 1-51.*

Database Caplus Chemical Abstracts Service, Columbus, Ohio, US; Database Accession No. 2014:573410, Abstract of CN 103709154, Wuhan Q & R Pharmaceutical Co., Ltd., Peop. Rep. China, Ge et al., Apr. 9, 2014.*

Chunyan Zhao et al., Pharmacology and clinical evaluation of edarbi, a new drug for the treatment of cardiovascular disease, Chinese Journal of New Drugs, 2011, vol. 20, No. 19, pp. 1831-1834.

* cited by examiner

BENZIMIDAZOLE DERIVATIVES AND PREPARATION PROCESS AND PHARMACEUTICAL USES THEREOF

TECHNICAL FIELD

The invention belongs to the technical field of pharmaceutical chemistry, and particularly pertains to benzimidazole derivatives, and preparation process and pharmaceutical uses thereof.

BACKGROUND ART

Hypertension is the most common cardiovascular disease, and it also is the primary dangerous factors which can lead to increased morbidity and mortality of congestive heart failure, stroke, coronary heart disease, renal failure, and aortic aneurysm. Antihypertensive drugs play a key role in the treatment and prevention of hypertension disease. With the deepening of understandings to the pathogenesis of the hypertension, many antihypertensive drugs having good efficacy, for example, such as diuretics, β-acceptor blockers, calcium channel blockers, angiotensin-converting enzyme inhibitor (ACEI, Pooley), Angiotensin II AT1 receptor blockers (ABR, Sartans), are continuously discovered and successfully applied in clinical practices. After years of clinical practice, it can be confirmed that because the kind of drugs can steadily reduce blood pressure and have good efficacy, long action time, good tolerance for patients, particularly, have many advantages in preventing stroke, delaying renal insufficiency of diabetes and non-diabetes nephropathy, improving left ventricular hypertrophy, and protecting target organs while producing no impacts on degradation of bradykinin and synthesis of prostaglandin, thereby not to cause dry cough and angioneurotic edema, AT1 receptor blockers Sartan drugs have been mainstream variety in global antihypertensive drug market. Although Sartan antihypertensive drugs have many advantages, their efficiency for reducing blood pressure is approximately about 50 to 60%, and the drugs have some adverse effects to some extent. Therefore, the development of long acting drugs with a low dosage and having good effect on reducing blood pressure, less adverse effects while having ideal efficacy in treatments of other diseases, e.g., diabetes, and good protective action on target organs, has been a developing direction in hot issue.

Nitrogen monoxide, as a messenger substance and an effect molecule, can have very important physiological functions in mammals, including controls to angiotasis, nerve conduction, hormone secretion, inflammation and immune reactions. In addition, it can also play important roles in regulations to vascular diastolic function, cell adhesion to vascular endothelium and platelet aggregation, cell proliferation of vascular smooth muscle and protections to ischemia-reperfusion injuries. ACE inhibitors have good actions on reducing blood pressure and protecting target organs. By inhibiting the activity of the ACE, on one hand, they can inhibit generations of angiotensin II so as to exert the function; on the other hand, they can work on the inhibition of endogenous peptides, e.g., bradykinin, to result in the increase of the concentration of bradykinin in vivo, so as to enhance the eNOs activity by activating $β_2$-receptors, thereby to promote endothelium-derived hyperpolarizing factor and NO release, thus to exert functions such as NO-mediated vasodilation and platelet aggregation inhibition.

AT1 receptor Losartan antagonists are a kind of novel antihypertensive drugs which are selectively bound to AT1 receptors, and block the actions of Ang II, thereby to result in reduction of blood pressure. However, as compared with ACE inhibitors, AT1 receptor blockers are lack of NO-mediated regulation function. Thus, AT1 acceptor blockers of NO donor type are developed to achieve the dual efficacy of blocking ATI acceptors and enhancing NO functions in vivo, and the type of ATI acceptor blockers can have more effective treating effects on hypertension, while having potential values to treat other cardiovascular diseases.

Ligustrazine (Lig) is one of primary chemical ingredients in the rhizomas of umbelliferae plant *Ligusticum Chuanxiong Hort* and Zingiberaceae plant *Curcuma Aromatica Salisb*, and the stem of Euphorbiaceae plant *Jatropha podagrica Hook*. Pharmacological studies proved that the Ligustrazine can act their functions to improve microcirculation, dilate blood vessels and increase blood flow, inhibit platelet aggregation and reduce platelet activity, and can have significant effects on the treatment of cardiovascular disease. Thus, clinically, the Ligustrazine is widely used in treatments of brain stroke, asthma, emphysema, pulmonary heart disease, chronic respiratory failure, adult respiratory distress syndrome and other diseases, and the mechanism primarily includes cleaning free radicals, resisting peroxidization of lipids, protecting crown pulse endothelial, promoting energy metabolism of myocardial cells, resisting fiberization, controlling expressions of apoptosis related genes c-fos and bcl-2, resisting injuries to free radicals, influencing cell factors, calcium antagonism, resisting myocardial hypoxia-complex oxygen injury, resisting myocardial mast caused by anti-vascular tension pigment II (blocking AT1 receptor), expanding vascular, and resisting platelet gathered and thrombogenesis. Ligustrazine AT1 acceptor blockers are developed, which either can effectively enhance the efficacy of the ATI acceptor blockers on resisting high blood pressure, or can effectively protect liver and kidney, while having potential therapeutical implications to other cardiovascular diseases. No relative reports are found in the prior art.

DESCRIPTIONS OF THE INVENTION

Directed to the defects present in the prior art, the objective of the invention is to provide a series of benzimidazole derivatives, comprising Ligustrazines and NO donor derivatives. The kind of the compounds can rapidly release Ligustrazine or NO in vivo, so that they can produce effective synergetic effects with Azilsartan, to enhance the anti-hypertension effect and reduce adverse effects, and released Ligustrazine can produce ideal protections to patients' liver and kidney.

In order to achieve the objective of the invention, the invention employs the following technical solution:

Benzimidazole derivatives as represented by the general formula I and pharmaceutically acceptable salts, solvates or polymorphs thereof:

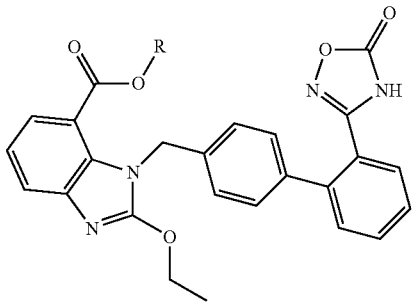

Where, R in the general formula I represents

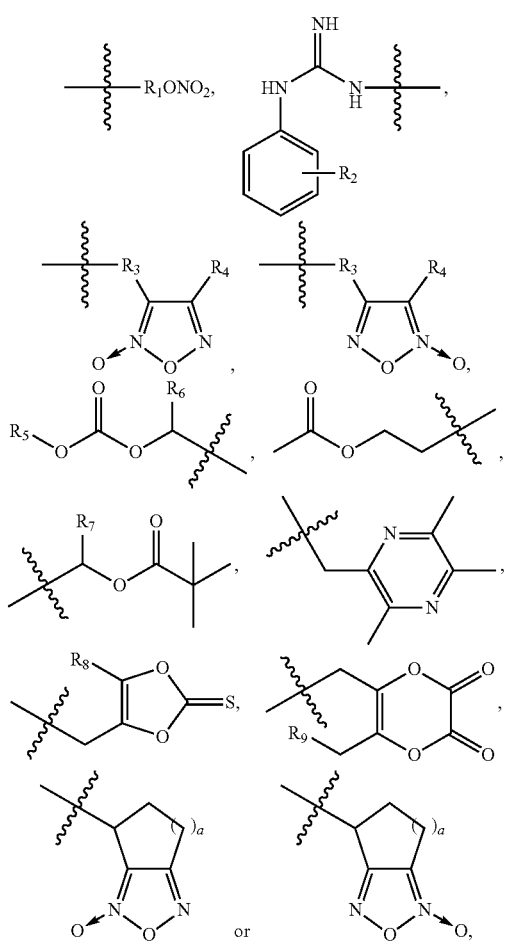

where a=0, 1, 2, 3, 4, 5 or 6;

Further, $R_1$ represents a $C_2$-$C_8$ alkyl, $C_2$-$C_8$ alkenyl, $C_2$-$C_8$ alkynyl,

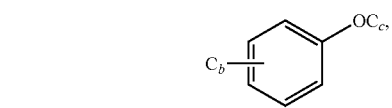

$(CH_2)_nO(CH_2)_m$,

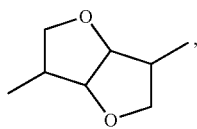

phenyl, substituted phenyl, aromatic heterocycle or substituted aromatic heterocycle, where in

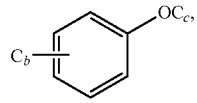

b, c=0, 1, 2, 3, 4, 5 or 6; in $(CH_2)_nO(CH_2)_m$, n, m=1, 2, 3, 4, 5 or 6.

Further, $R_2$ represents hydrogen, halogens, trifluoromethyl, $C_1$-$C_8$ alkoxy, $C_1$-$C_8$ alkyl, nitro, sulfonamido, amino or cyano.

Further, $R_3$ represents a $C_1$-$C_8$ alkylidene, $C_1$-$C_8$ alkoxy, $C_2$-$C_8$ alkenyloxy, $C_2$-$C_8$ alkynyloxy, $(C_1$-$C_6)O(C_1$-$C_6)$,

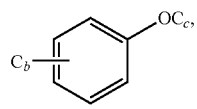

phenyl, substituted phenyl, aromatic heterocycle or substituted aromatic heterocycle, where in

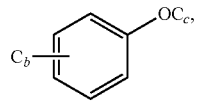

b, c=0, 1, 2, 3, 4, 5 or 6.

Further, $R_4$ represents a phenyl, substituted phenyl, benzene sulphonyl, 5- to 6-membered aromatic heterocycle, substituted 5- to 6-membered aromatic heterocycle, cyano, trifluoromethyl, $C_1$-$C_8$ alkyoxy, $C_1$-$C_8$ nitrate ester group or $C_1$-$C_8$ alkyl.

Further, $R_5$ represents a phenyl, substituted phenyl, 5- to 6-membered aromatic heterocycle, substituted 5- to 6-membered aromatic heterocycle, cyano, trifluoromethyl, $C_1$-$C_8$ alkoxy, $C_1$-$C_8$ nitrate ester group, $C_1$-$C_8$ alkyl, $C_2$-$C_8$ alkenyl, $C_2$-$C_8$ alknyl,

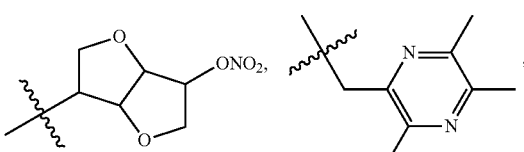

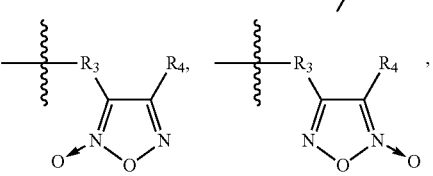

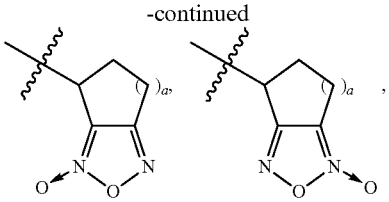

or $(CH_2)_nO(CH_2)_m$, where $R_3$, $R_4$, a, n, m have the meanings as previously described.

Further, $R_6$ and $R_7$ represent hydrogen, $C_1$-$C_8$ alkoxy or $C_1$-$C_8$ alkyl.

Further, $R_8$ and $R_9$ represent hydrogen, $C_1$-$C_8$ alkoxy, $C_1$-$C_8$ nitrate ester group or $C_1$-$C_8$ alkyl.

The "substituted phenyl" means a phenyl which is substituted with one or more selected from the group consisting of hydroxyl, $C_1$-$C_6$ alkyl, $C_1$-$C_6$ alkoxy, halogens, nitro, amino, cyano, trifluoromethyl, —CH=CHCO$_2$R$_{11}$, each of which may be the same or different from each other, wherein $R_{11}$ represents hydrogen or $C_1$-$C_6$ alkyl.

The "aromatic heterocycle" means a 5 to 7-membered aromatic cycle containing 1 to 4 heteroatoms, the heteroatoms, independently from each other, being selected from the group of O, S, or N.

The "substituted aromatic heterocycle" means being optionally substituted with one or more group selected from the group consisting of $C_1$-$C_6$ alkyl, $C_1$-$C_6$ alkoxy, halogens, each of which may be the same or different.

Further, R represents

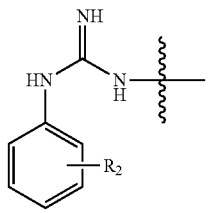

wherein $R_2$ is a meta- or para-substituent.

Further, R represents

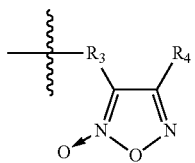

wherein $R_3$ represents $C_1$-$C_8$ alkylidene, and $R_4$ represents a phenyl, or a substituted phenyl at meta- or para-position.

Further, R represents

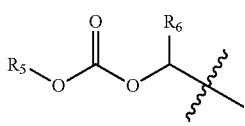

wherein $R_5$ represents

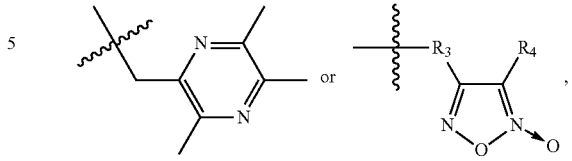

and $R_6$ represents hydrogen or a $C_1$-$C_8$ alkyl.
Further, the $R_3$ represents $C_1$-$C_8$ alkylidene group.
Further, R represents

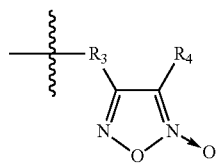

wherein $R_3$ represents $C_1$-$C_8$ alkylidene, and $R_4$ represents $C_1$-$C_8$ alkyl, $C_1$-$C_8$ nitrate ester group or cyano.

Representative compounds having the general formula I according to the invention may be exemplified as follows:

QR01002: (isopropyloxy-carbonyloxy)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01003: 1-(isopropyloxy-carbonyloxy)ethyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01004: acetoxyethyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01005: pivaloyloxymethyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01006: (3,5,6-trimethylpyrazine-2-yl)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01007: 6-(nitrooxyester)hexahydrofuran[3,2-b]furan-3-yl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01008: 4-nitrooxybutyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01009: (4-phenyl-1,2,5-oxadiazole-2-oxide-3-)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01010: (4-phenyl-1,2,5-oxadiazole-2-oxide-3-)methoxyphenoxy-2-ethoxy-1-{[2'-(5-oxo-4,5-dihydro-1,2,4-oxadiazole)-3-yl)biphenyl-4-yl]methyl}-1H-benzimidazole-7-carboxylate;

QR01011: 4-(3-benzenesulfonyl-1,2,5-oxadiazole-2-oxide-3-)oxybutyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01012: 2-ethoxy-1-{[2'-(5-oxo-4,5-dihydro-1,2,4-oxadiazole)-3-yl)biphenyl-4-yl]methyl}-1H-benzimidazole-7-carboxylic acid-(N-phenyl-N'-hydroxyguanidine) ester;

QR01013: (5-methyl-3-thio-1,3-dioxole-4-yl)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01014: (3-methyl-5,6-dioxy-5,6-dihydro-1,4-dioxa-2-)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01015: 3-[hydroxy-ethyl oxalate]-2-oxo-butyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01016: 2-nitrooxyethyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01017: (3,5,6-trimethylpyrazine-2-methoxy-carbonyloxy)methyl-2-ethoxy-1-{[2'-(5-oxo-4,5-dihydro-1,2,4-oxadiazole)-3-yl]biphenyl-4-yl]methyl}-1H-benzimidazole-7-carboxylate;

QR01019: 1-(3,5,6-trimethylpyrazine-2-methoxy-carbonyloxy)ethyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01020: (3-methyl-1,2,5-oxadiazole-2-oxide-3-methoxy-carbonyloxy)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01021: 1-(3-methyl-1,2,5-oxadiazole-2-oxide-3-methoxy-carbonyloxy)ethyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01023: 4-(3-methyl-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01025: 3-(4-methyl-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01026: 4-(3-tert-butyl-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01027: 1-(3,5,6-trimethylpyrazine-2-methoxy-carbonyloxy)isobutyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01028: 1-(3,5,6-trimethylpyrazine-2-methoxy-carbonyloxy)neopentyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01029: 1-(6-methypyridazine-2-methoxy-carbonyloxy)ethyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01030: (isoxazole-5-methoxy-carbonyloxy)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01031: (1-methylimidazole-4-methoxy-carbonyloxy)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01032: (1-methylpyrrole-3-methoxy-carbonyloxy)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01033: 1-(1-methylpyrrole-3-methoxy-carbonyloxy)ethyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01034: 4-(3-nitratemethyl-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

QR01035: 4-{2-ethoxy-1-[2'-(5-oxo-4,5-dihydro-1,2,4-oxadiazole)-3-yl)biphenyl-4-yl]methyl}-1H-benzimidazole-7-carboxylate-5,6-dihydro-4H-cyclopentyl[c]{[1,2,5]oxadiazole-2-oxide}-1-methyl QR01036: 4-(3-cyano-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate.

The above compounds QR01002 to QR01036 have the following corresponding chemical formulae:

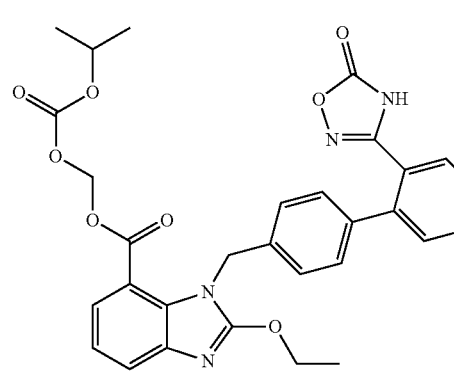

QR01002

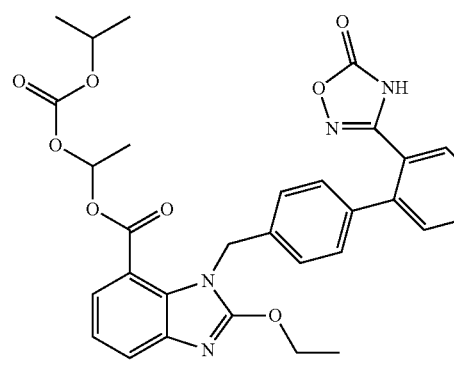

QR01003

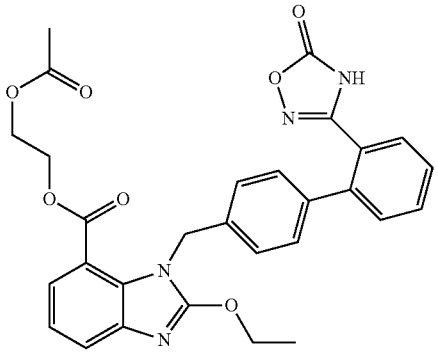

QR01004

QR01005
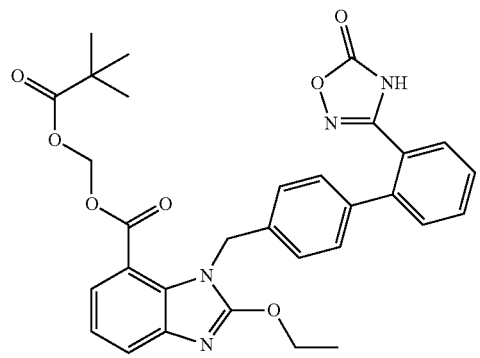
QR01006
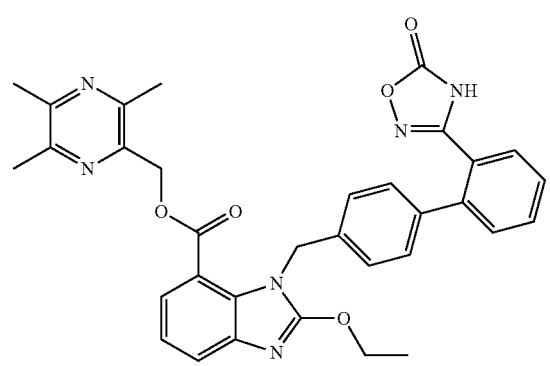
QR01007
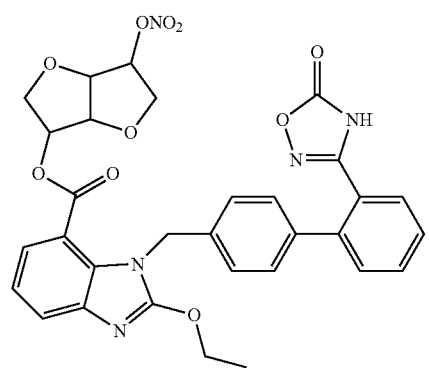
QR01008
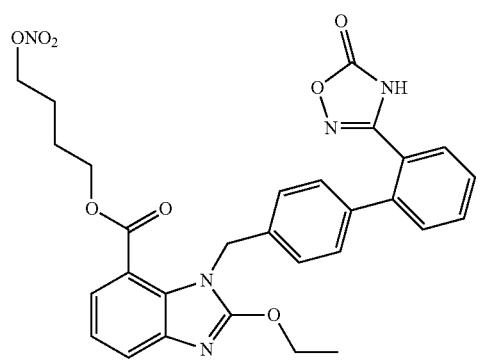
QR01009
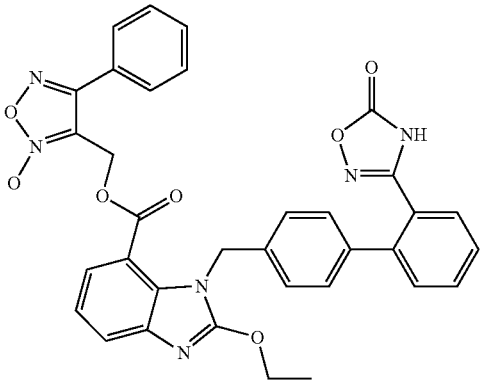
QR01010
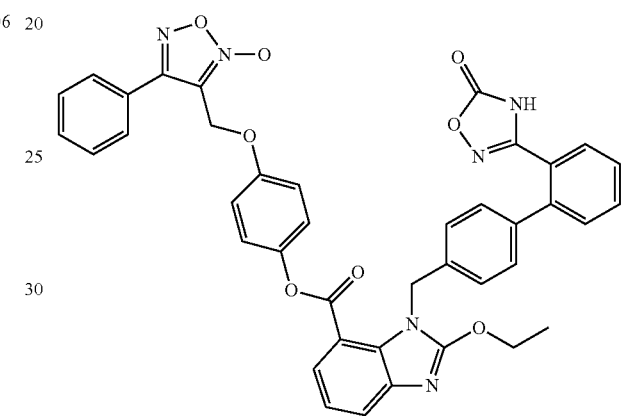
QR01011
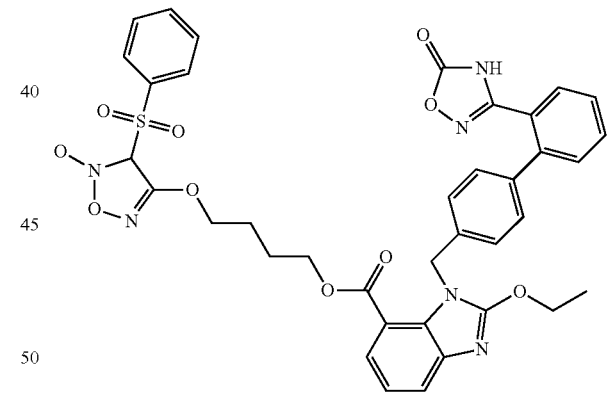
QR01012
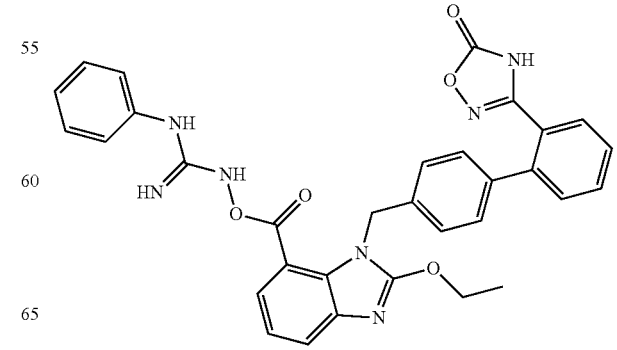

-continued
QR01013
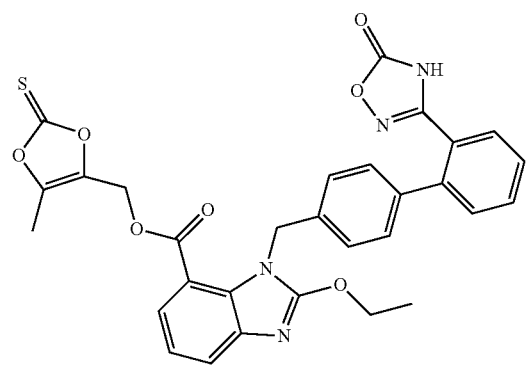
QR01014
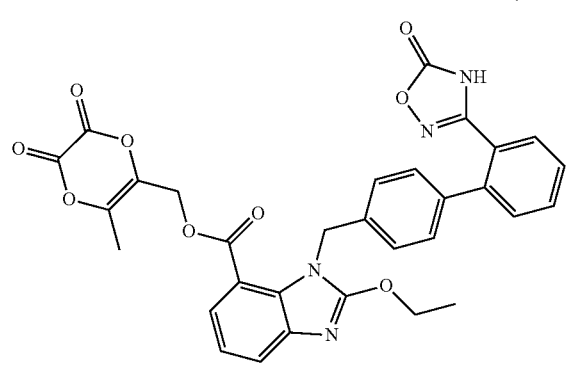
QR01015
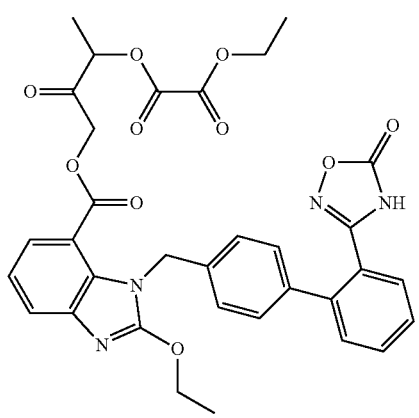
QR01016
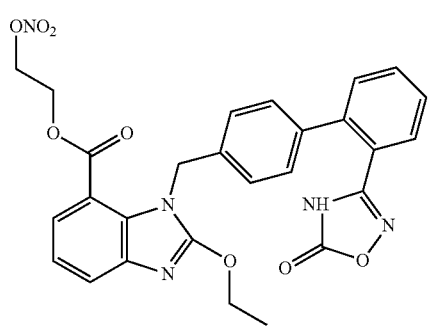
-continued
QR01017
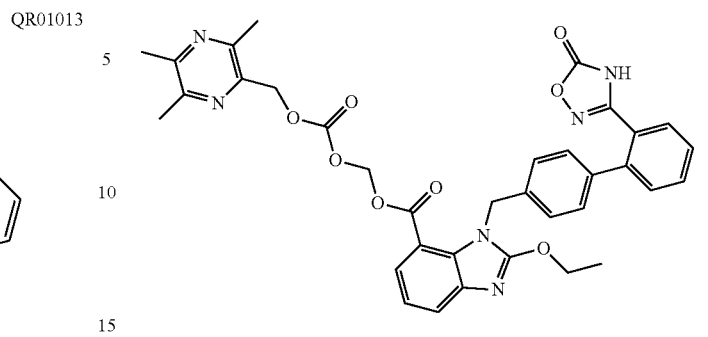
QR01019
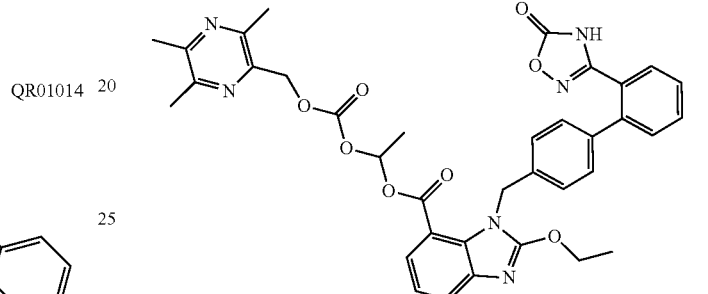
QR01020
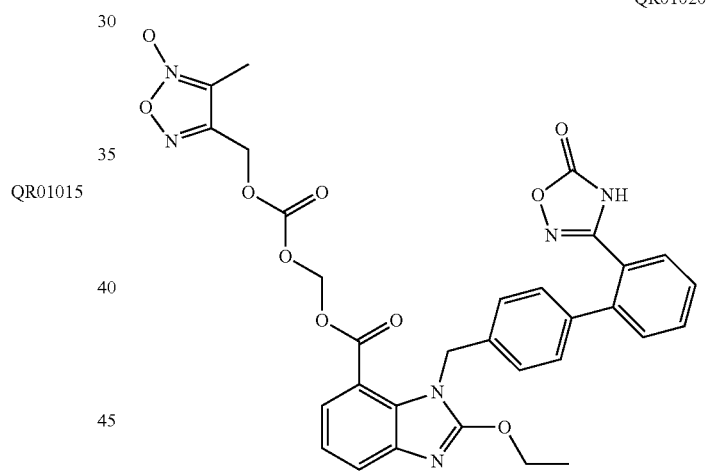
QR01021
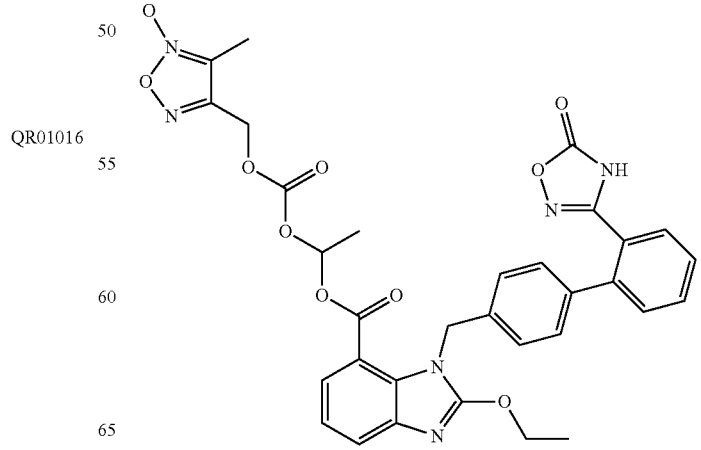

QR01023
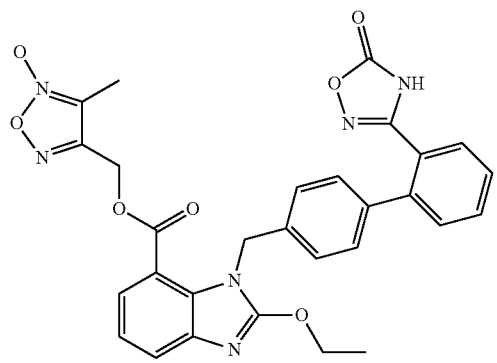
QR01028
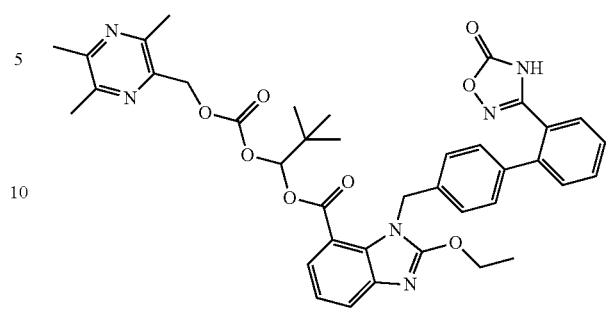
QR01025
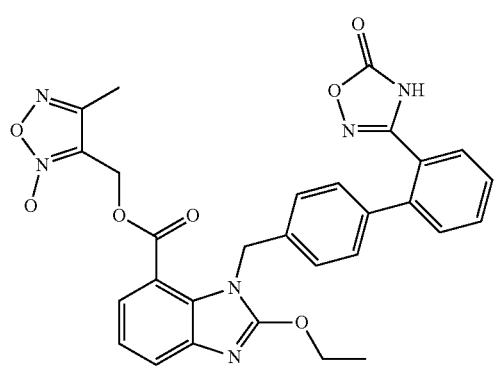
QR01029
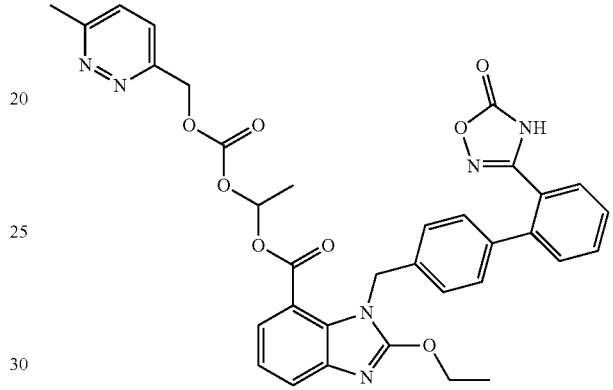
QR01026
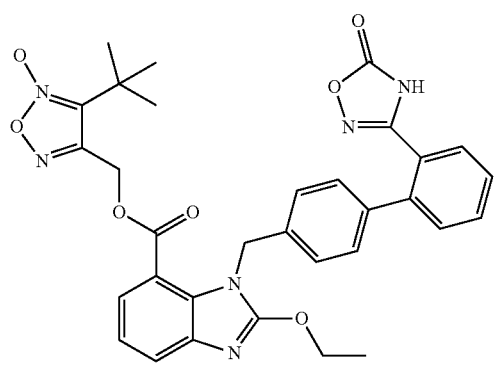
QR01030
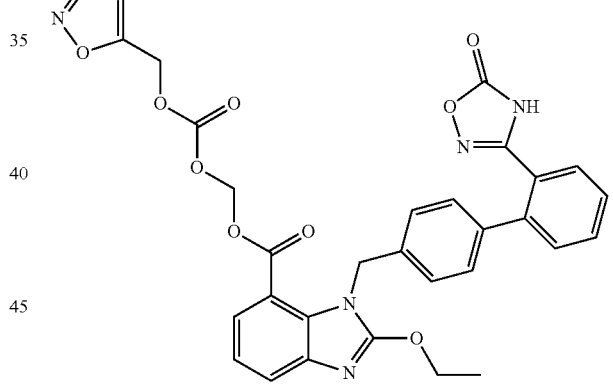
QR01027
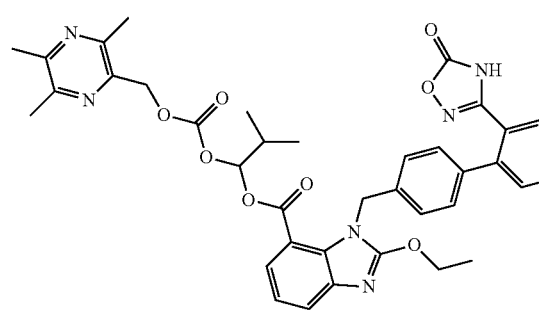
QR01031
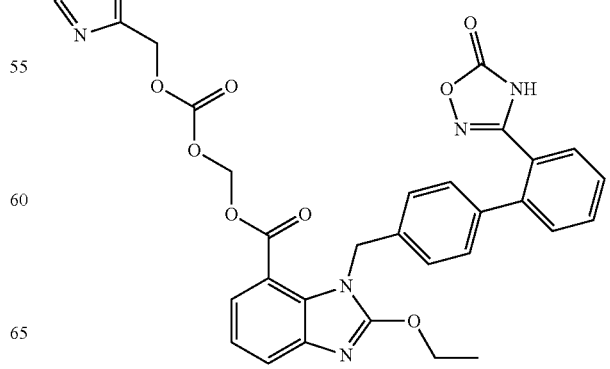

QR01032

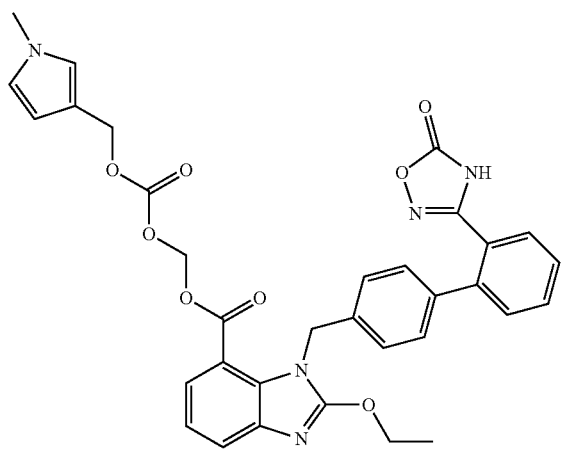

QR01033

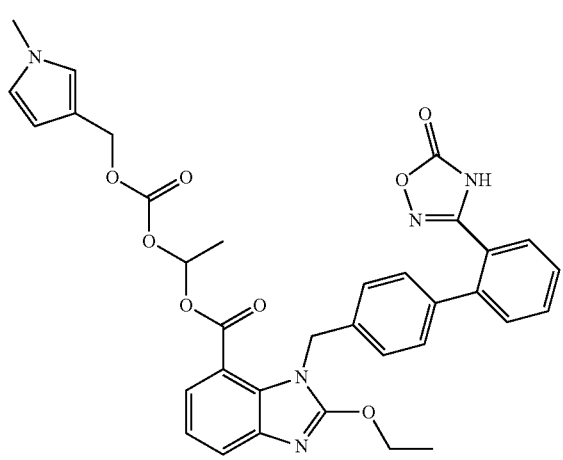

QR01034

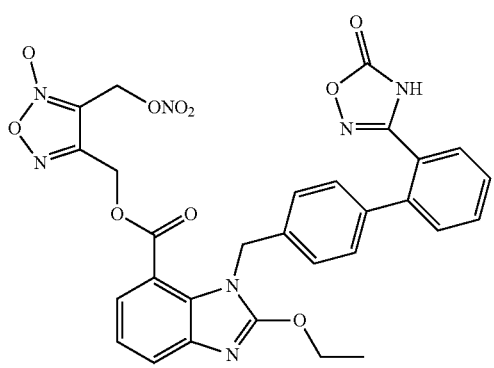

QR01035

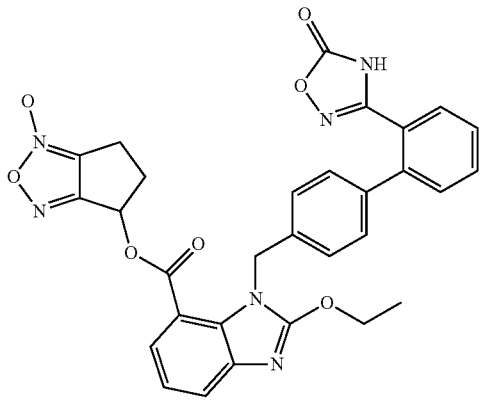

QR01036

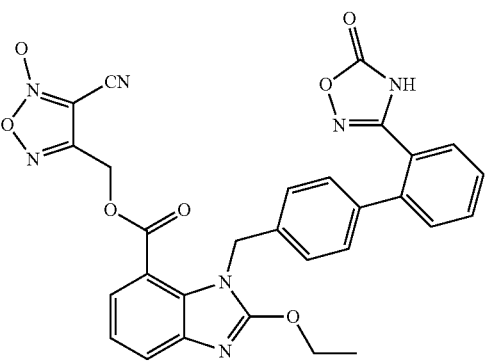

Further, the pharmaceutically acceptable salts may be potassium salts.

More further, the pharmaceutically acceptable salts may be potassium salts as represented by the general formula II:

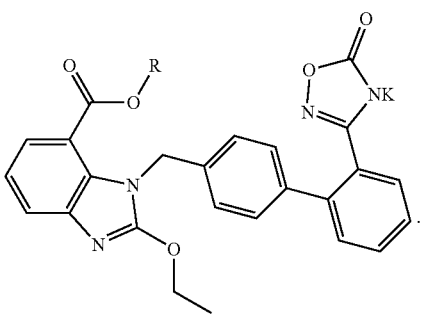

II

For example, potassium salt of the QR01019 may be potassium 1-(3,5,6-trimethylpyrazine-2-methoxy-carbonyloxy)ethyl-2-ethoxy-1-{[2'-(5-oxo-4,5-dihydro-1,2,4-oxadiazole)-3-yl)biphenyl-4-yl]methyl}-1H-benzimidazole-7-carboxylate:

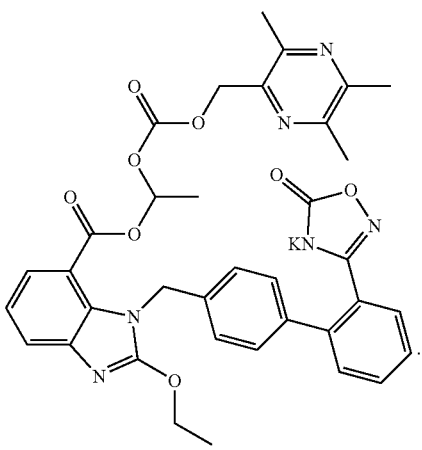

The invention further provides a plurality of processes for manufacturing the compounds as represented by the general formula I:

(1) a process comprising the steps of reacting Azilsartan with an acylating agent in the presence of an alkali to produce a mixed acid anhydride, and reacting the mixed acid anhydride with an alcohol having the structure R—OH in the presence of an alkali:

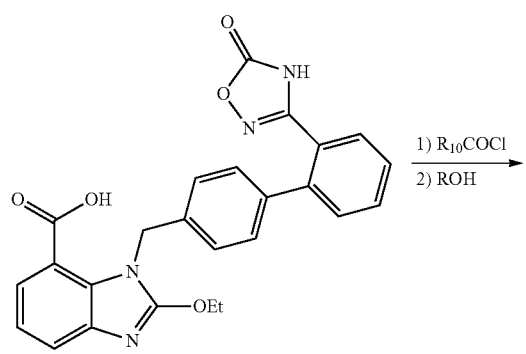

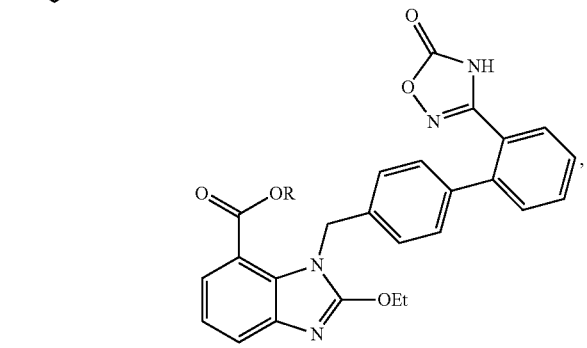

where $R_{10}COCl$ is an acylating agent and $R_{10}$ is not specially required. In a certain embodiment, the acylating agent may be paramethybenzenesulfonyl chloride, and the alkali is a mixture of potassium carbonate and N,N-dimethylpyridylamine.

(2) a process comprising the step of reacting Azilsartan with an alkylating agent in the presence of an alkali, where the alkali is $Et_3N$/N-methylpyrrolidone, and the alkylating agent may be an halogenating agent having the structure R—X, wherein X is a halogen atom:

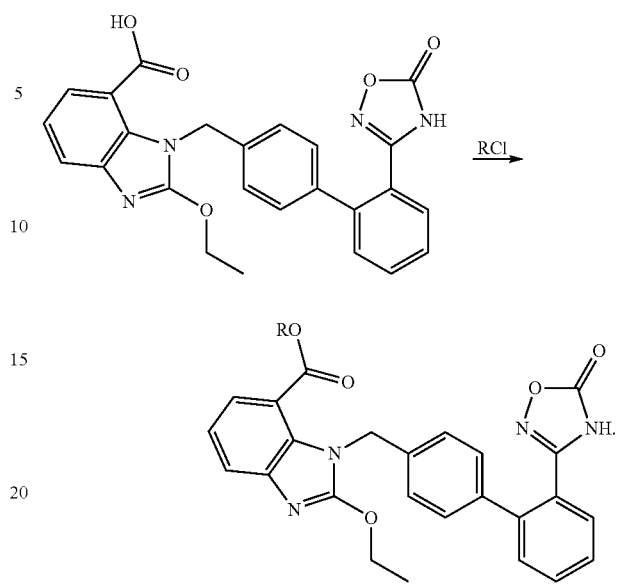

In a certain embodiment, the alkylating agent is prepared by reacting any one of chloromethyl chloroformate and 2-chloro-ethyl chloroformate with an alcohol:

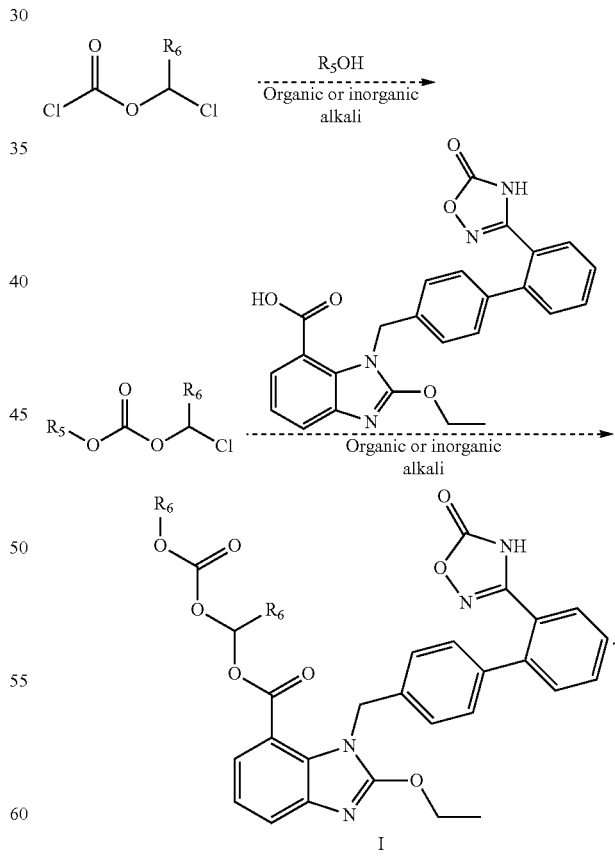

(3) a process comprising the esterification reaction of Azilsartan with an alcohol having the structure R—OH in the presence of a condensation agent, in which, the condensation agent is DCC/DMAP:

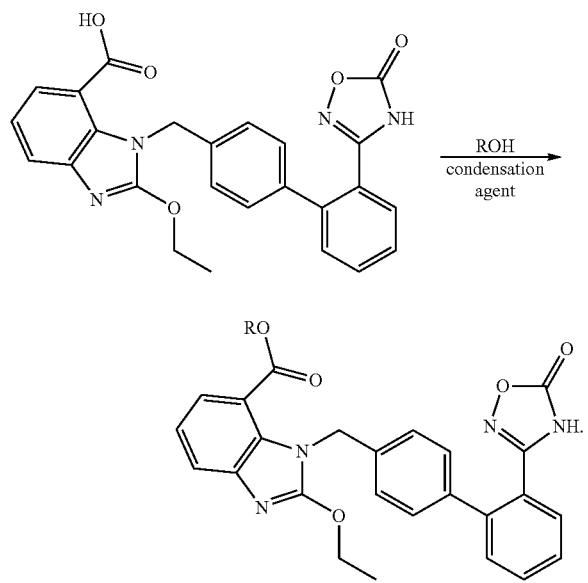

In a certain embodiment, the alcohol having the structure R—OH is a halogenated alcohol. The halogenated alcohol and Azilsartan take esterification to produce an ester, and thereafter, the process further comprises the step of reacting the ester with silver nitrate:

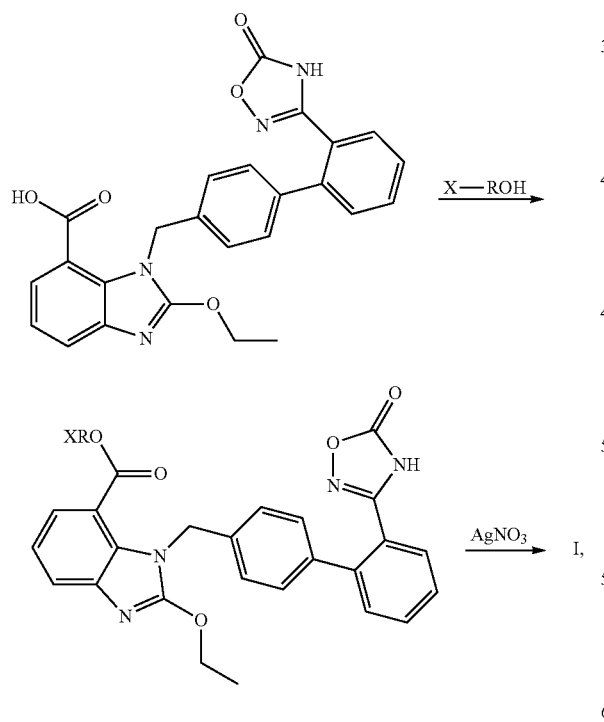

In which X represents Cl or Br.

In another certain embodiment, the alcohol having the structure R—OH is a diol. The diol and Azilsartan take monoesterification to produce a monoester, and thereafter, the process comprises the step of reacting the monoester with fuming nitric acid:

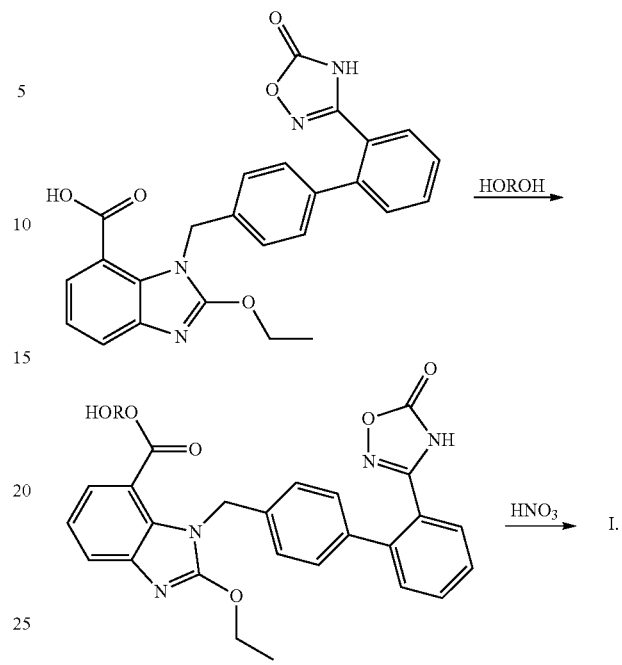

In another embodiment, when R represents the substituent

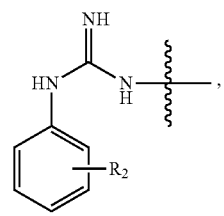

the R—OH is an N-aryl-N'-hydroxyguanidine, and the specific reaction step is shown as follow:

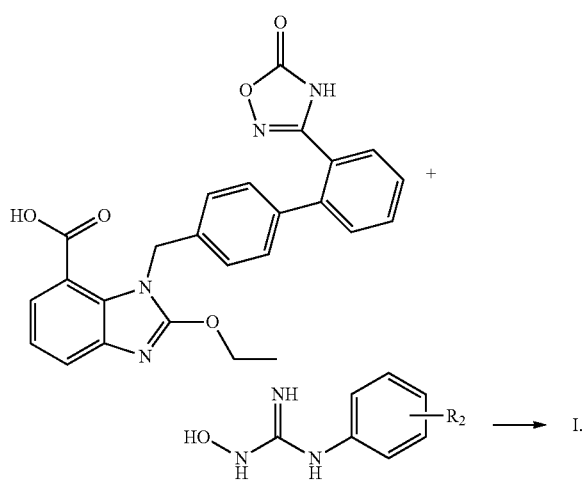

(4) a process comprising the step of reacting Azilsartan with furazan oxynitride NO donors in the presence of an alkali catalyst, in which R represents

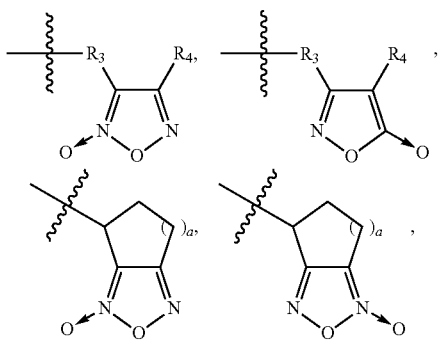

and the alkali catalyst may be DCC/DMAP or Et$_3$N/N-methylpyrrolidone:

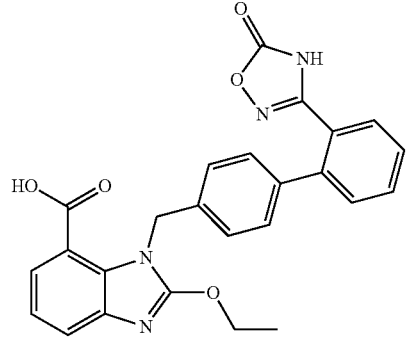
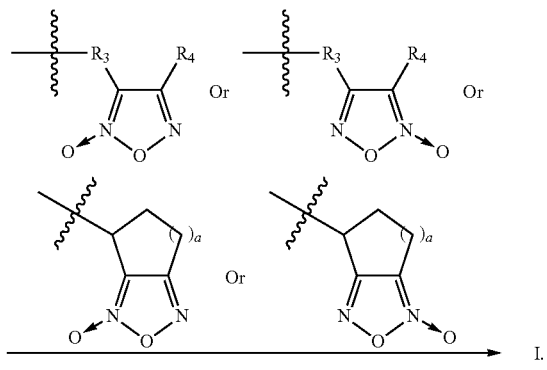

The invention further provides a process for preparing the compounds as represented by the general formula II, comprising the steps of dissolving the compounds as represented by the general formula I according to any one of claims 1 to 7 in a solvent, adding potassium salts thereto in a refluxing state to conduct the reaction, and cooling the reaction mixture to precipitate crystals.

Further, the solvent may be any organic solvents which can dissolve the compounds as represented by the general formula I.

More further, the solvent may be selected from the group consisting of ether solvents, ketone solvents, alcohol solvents, esters solvents, alkane solvents, aromatic hydrocarbon solvents, nitrile solvents or combinations thereof.

In certain embodiments, the ether solvents can be selected from the group consisting of methyltetrahydrofuran, tetrahydrofuran, dioxane, ethylene glycol dimethyl ether, methyl tert-butyl ether or isopropyl ether, etc.; the ketone solvents can be selected from the groups of acetone, methyl ethyl ketone or 4-methyl-2-pentanone, etc.; the alcohol solvents can be selected from the group consisting of methanol, ethanol, n-propanol, isopropanol, n-butanol or t-butanol, etc.; the ester solvents can be selected from the group consisting of ethyl acetate, n-propyl acetate, isopropyl acetate, n-butyl acetate, isobutyl acetate, sec-butyl or tert-butyl acetate, etc.; the alkane solvents can be selected from the group consisting of dichloromethane, 1,2-dichloroethane, chloroform, carbon tetrachloride, nitroethane, n-hexane, cyclohexane, pentane or n-heptane, etc.; the aromatic hydrocarbon solvents can be selected from the group consisting of benzene, toluene or xylene, etc.; the nitrile solvents can be selected from acetonitrile or malononitrile, etc.

Further, examples of the potassium salt may include potassium nitrate, potassium sulfate, potassium sulfite, potassium bromate, potassium bicarbonate, potassium thiocyanate, potassium hydrogen phosphate, potassium hydrogen phthalate, potassium acetate, potassium formate, tert-butyl potassium phosphate, dipotassium glycyrrhizinate, potassium 2-ethylhexanoate, potassium ethyl xanthate, potassium sorbate, potassium phthalimide, maleimide potassium, potassium oxalate, potassium salt of olefine acid, potassium citrate, potassium malate, potassium grapes, potassium lactate, potassium tartrate, potassium salicylate, potassium fumarate, potassium stearate, potassium laurate, etc., or combinations thereof.

The invention further provides uses of the compounds as represented by the general formula I and pharmaceutically acceptable salts, solvates or polymorphs thereof in the manufacture of drugs which can treat and/or prevent cardiovascular diseases.

Particularly, the cardiovascular diseases may include primary hypertension, secondary hypertension, heart disease, heart failure, myocardial infarction, atherosclerosis, diabetic complications, diabetic nephropathy, dyslipidemia or high triglyceride hyperlipidemia, etc.

The invention further provides a pharmaceutical composition comprising a therapeutically effective amount of compounds of the general formula I according to any one of claims 1 to 7, and pharmaceutically acceptable salts, solvates or polymorphs thereof, and pharmaceutically acceptable adjuvants.

Further, the adjuvants may include fillers and disintegrating agents which are commonly used in pharmaceutical technology. For example, the fillers may include one or more selected from lactose, mannitol, and microcrystalline cellulose; the disintegrating agents may include one or more selected from hydroxypropylcellulose, carboxymethylcellulose, sodium carboxymethylcelluse and crospovidone.

The pharmaceutical compositions in accordance with the invention may be in various dosage forms applicable for clinical applications, such as oral agents, e.g., tablets or soft capsules, dispersible tablets, release retarders or liposome formulations.

The invention further provides a method of treating various cardiovascular diseases as above described, comprising administrating the above pharmaceutical composition to patients. As to an adult patient having a body weight in a normal range, the administrate dosage for clinical treatment may be 10 to 100 mg per day, orally administrated.

As compared with the prior art, the technical solution of the invention has the following advantages and beneficial effects:

1. The invention discloses a series of benzimidazole derivatives, mainly including derivatives that can form esters with ligustrazine, nitrogen monoxide donor, (5-methyl-2-thio-1,3-dioxole-)methanol and (3-methyl-5,6-dioxy-5,6-dihydrogen-1,4-dioxa-2-) methanol.

2. After the novel compounds of the present invention enter a human body, these compounds will be rapidly metabolized into Azilsartan and ligustrazine or release a certain level of NO, thereby greatly enhancing the antihypertensive activity of the Azilsartan.

3. The compounds as provided in the invention, as Ligustrazine ATI acceptor blockers, either can effectively enhance the antihypertensive efficacy of the ATI acceptor blockers, or can achieve effective protections to liver and kidney.

DESCRIPTION TO THE DRAWINGS

Figure 2:
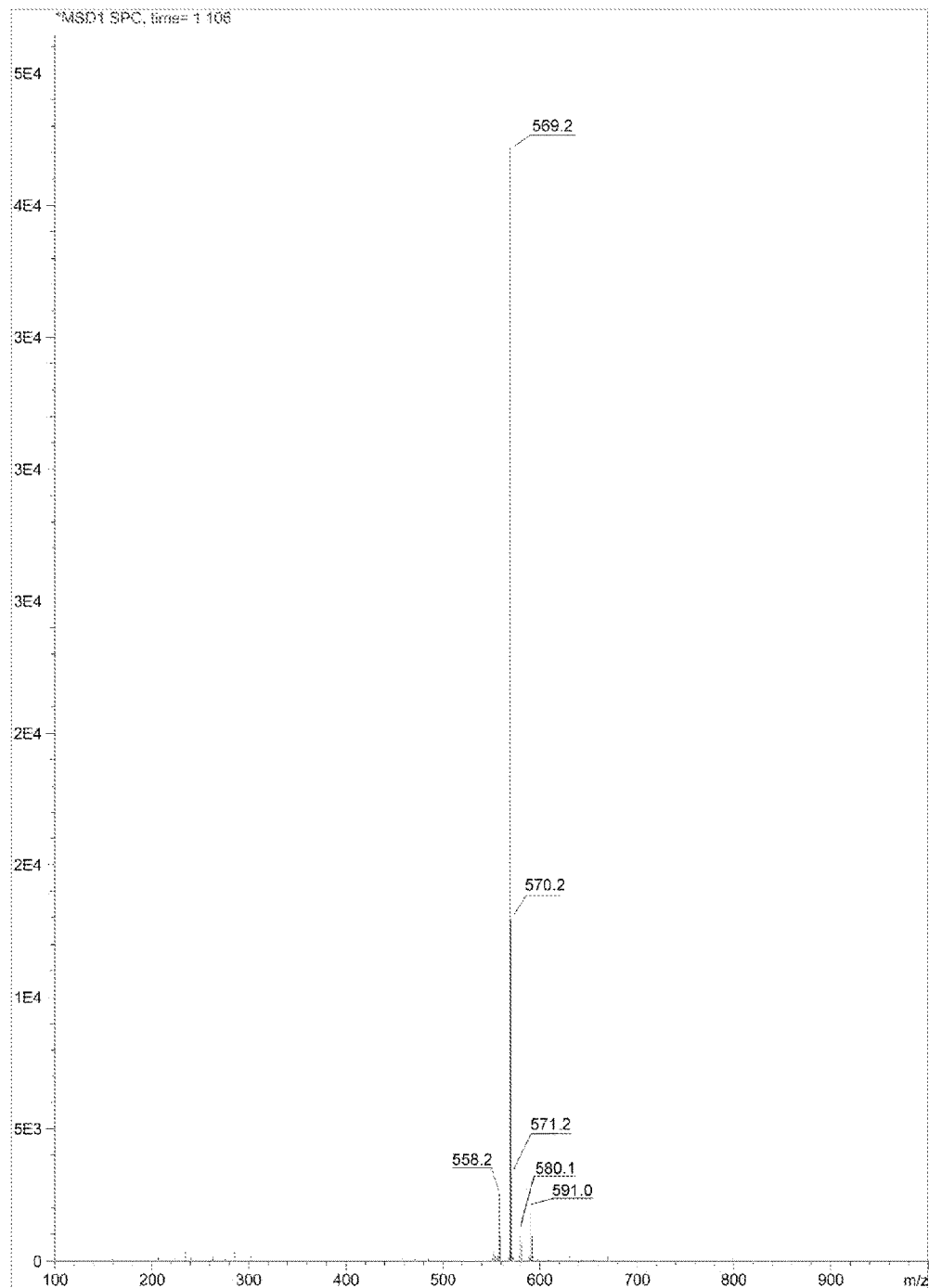
Figure 3:
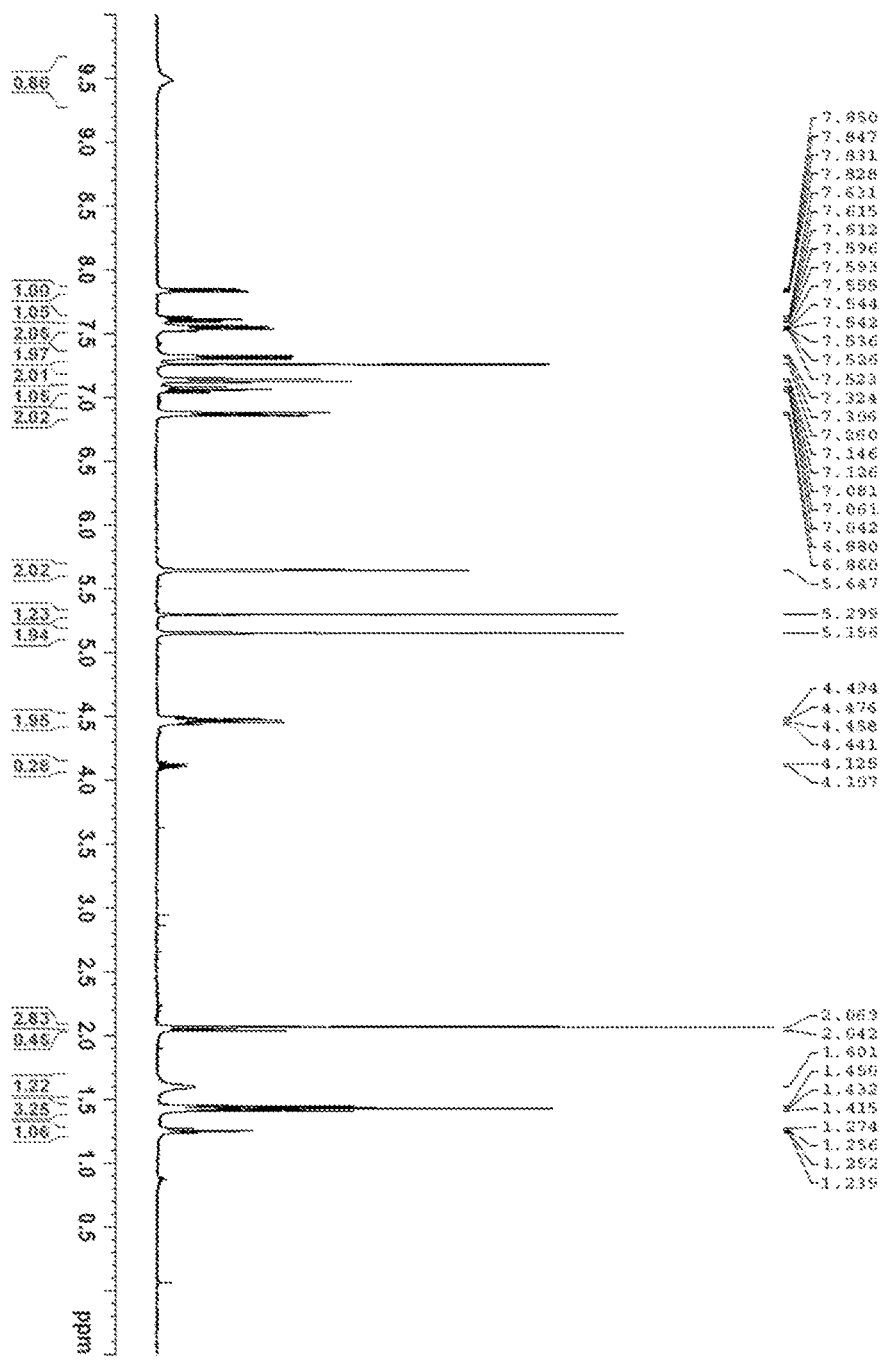

FIG. 1 is a LCMS spectrum of the product QR01023 as prepared in Example 23;
FIG. 2 is a MS spectrum of the product QR01023 as prepared in Example 23, MS+: 569.2;
FIG. 3 is a nuclear magnetic resonance hydrogen (NMRH) spectrum of the product QR01023 as prepared in Example 23.

SPECIFIC MODES FOR CARRYING OUT THE INVENTION

The invention is further described in detailed in combination with the following specific embodiments, with the purpose of enabling those skilled in the art to more clearly understand the invention. However, the following contents should be understood in no way to limit the protection scope as claimed by the claims of the invention. If not otherwise specified, the technical means as used in the examples are all conventional means well known for those skilled in the art.

Example 1

Synthesis of (isopropyloxo-carbonyloxy) methyl-2-ethoxy-1-{[2'-(5-oxo-4, 5-dihydro-1,2,4-oxadiazole)-3-yl)biphenyl-4-yl]methyl}-1H-benzimidazole-7-carboxylate

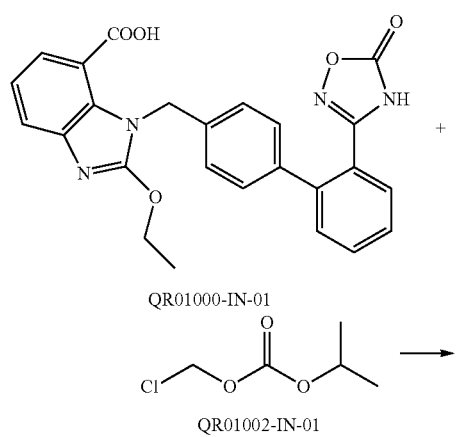

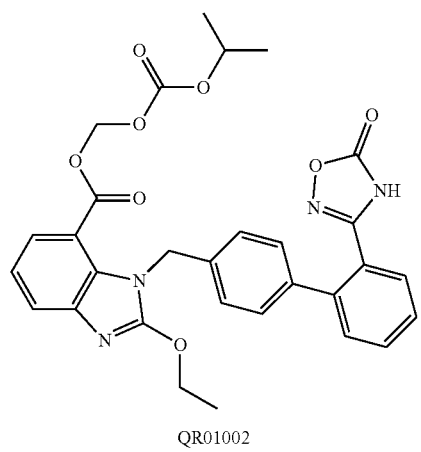

QR01002

The QR01000-IN-01 (2.2 mmol, 1.0 eq.) and the QR01002-IN-01 (3.3 mmol, 1.5 eq.) were dissolved in 20 mL of N-methylpyrrolidone, and then triethylamine (4.4 mmol, 2.0 eq.) was added thereto. The resulting mixture was heated to 65° C. and the TLC was used to monitor the reaction until the reaction is completed. To the reaction solution was added water and ethyl acetate, to perform an extraction, and the resulting organic layer was washed with water and saturated brine. The organic layer was dried and concentrated, and it is purified by column chromatography to give the title compound QR01002, its structure being dually confirmed by LCMS and NMRH spectra.

Example 2

Synthesis of 1-(isopropyloxo-carbonyloxy) ethyl-2-ethoxy-1-{[2'-(5-oxo-4,5-dihydro-1,2,4-oxadiazole)-3-yl)biphenyl-4-yl]methyl}-1H-benzimidazole-7-carboxylate

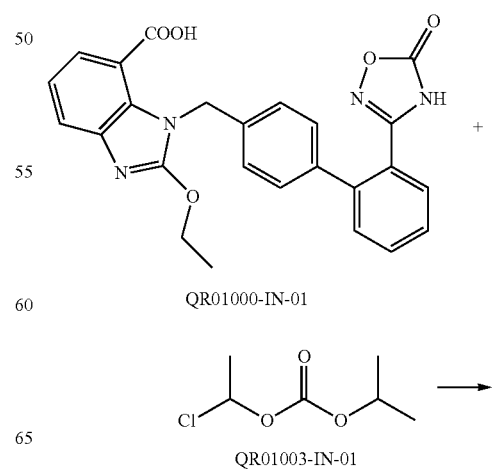

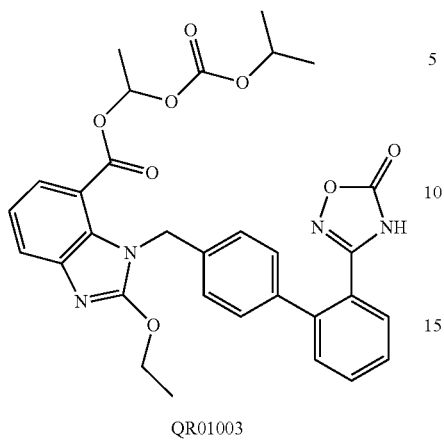

QR01003

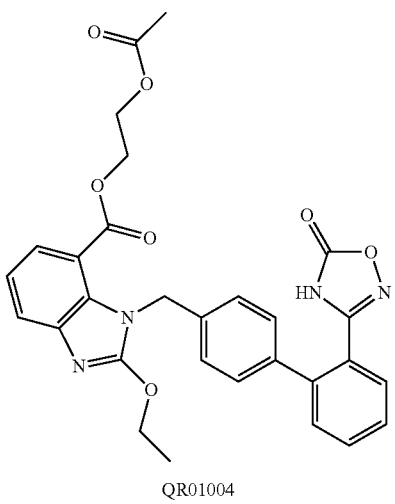

QR01004

The QR01000-IN-01 (2.2 mmol, 1.0 eq.) and the QR01003-IN-01 (3.3 mmol, 1.5 eq.) were dissolved in 20 mL of N-methylpyrrolidone, and then triethylamine (4.4 mmol, 2.0 eq.) was added thereto. The resulting mixture was heated to 65° C. and the TLC was used to monitor the reaction until the reaction is completed. To the reaction solution was added water and ethyl acetate, to perform an extraction, and the resulting organic layer was washed with water and saturated brine. The organic layer was dried and concentrated, and it is purified by column chromatography to give the title compound QR01003, its structure being dually confirmed by LCMS and NMRH spectra.

Example 3

Synthesis of acetoxyethyl-2-ethoxy-1-{[2'-(5-oxo-4,5-dihydro-1,2,4-oxadiazole)-3-yl)biphenyl-4-yl]methyl}-1H-benzimidazole-7-carboxylate

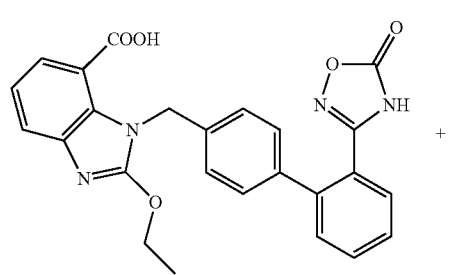

QR01000-IN-01

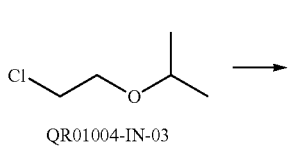

QR01004-IN-03

The QR01000-IN-01 (2.2 mmol, 1.0 eq.) and the QR01004-IN-01 (3.3 mmol, 1.5 eq.) were dissolved in 20 mL of N-methylpyrrolidone, and then triethylamine (4.4 mmol, 2.0 eq.) was added thereto. The resulting mixture was heated to 65° C. and the TLC was used to monitor the reaction until the reaction is completed. To the reaction solution was added water and ethyl acetate, to perform an extraction, and the resulting organic layer was washed with water and saturated brine. The organic layer was dried and concentrated, and it is purified by column chromatography to give the title compound QR01004, its structure being dually confirmed by LCMS and NMRH spectra.

Example 4

Synthesis of pivaloyloxymethyl-2-ethoxy-1-{[2'-(5-oxo-4,5-dihydro-1,2,4-oxadiazole)-3-yl)biphenyl-4-yl]methyl}-1H-benzimidazole-7-carboxylate

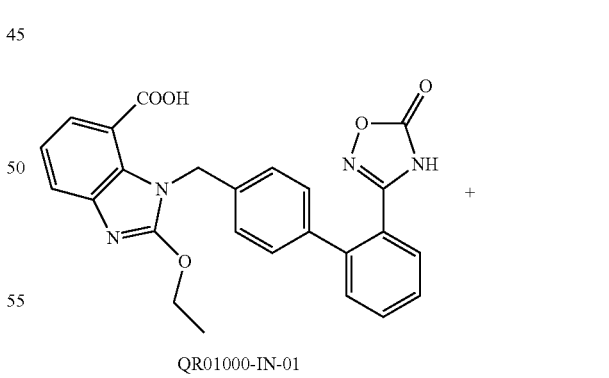

QR01000-IN-01

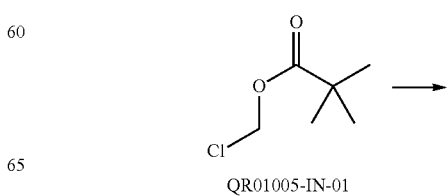

QR01005-IN-01

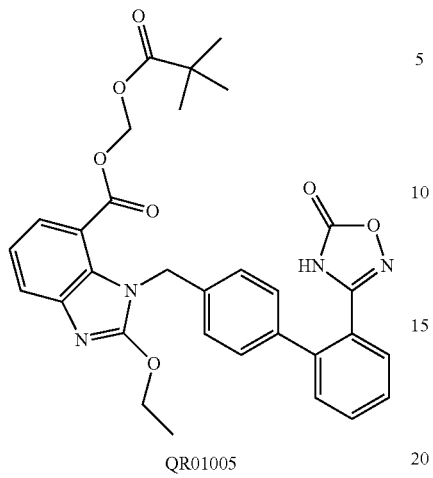

QR01005

The QR01000-IN-01 (2.2 mmol, 1.0 eq.) and the QR01005-IN-01 (3.3 mmol, 1.5 eq.) were dissolved in 20 mL of N-methylpyrrolidone, and then triethylamine (4.4 mmol, 2.0 eq.) was added thereto. The resulting mixture was heated to 65° C. and the TLC was used to monitor the reaction until the reaction is completed. To the reaction solution was added water and ethyl acetate, to perform an extraction, and the resulting organic layer was washed with water and saturated brine. The organic layer was dried and concentrated, and it is purified by column chromatography to give the title compound QR01005, its structure being dually confirmed by LCMS and NMRH spectra.

Example 5

Synthesis of (3,5,6-trimethylpyrazine-2-yl) methyl-2-ethoxy-1-{[2'-(5-oxo-4,5-dihydro-1,2,4-oxadiazole)-3-yl)biphenyl-4-yl]methyl}-1H-benzimidazole-7-carboxylate

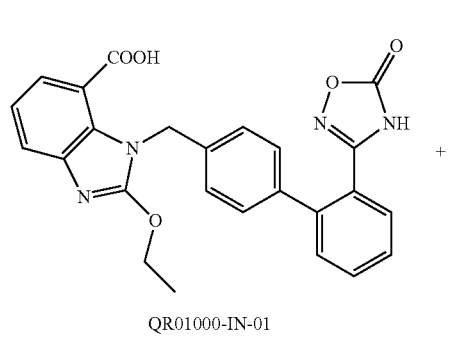

QR01000-IN-01

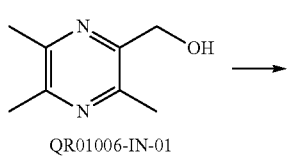

QR01006-IN-01

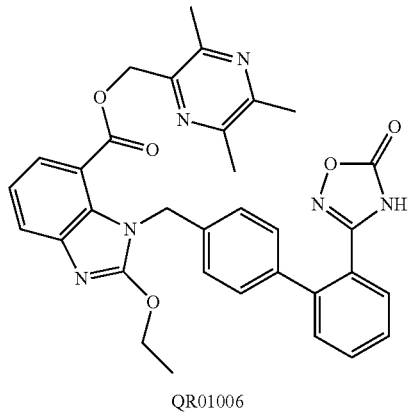

QR01006

The QR01000-IN-01 (2.2 mmol, 1.0 eq.) and the QR01006-IN-01 (2.6 mmol, 1.2 eq.) were dissolved in 20 ml of dimethylformamide, cooled to 10° C. To the resulting solution, potassium carbonate (2.6 mmol, 1.2 eq.), p-toluenesulfonyl chloride (2.6 mmol, 1.2 eq.), and a dimethylaminopyridine catalyst were added and the resulting mixture was stirred for 3 h. After the completion of the reaction, water was added to the reaction solution, extracted with ethyl acetate. The resulting organic layer was washed with water and saturated brine. Crude product was purified by column chromatography to give the title compound QR01006, its structure being dually confirmed by LCMS and NMRH spectra.

Example 6

Synthesis of 6-(nitrooxyester) hexahydrofuran[3,2-b]furan-3-yl-2-ethoxy-1-{[2'-(5-oxo-4,5-dihydro-1,2,4-oxadiazole)-3-yl)biphenyl-4-yl]methyl}-1H-benzimidazole-7-carboxylate

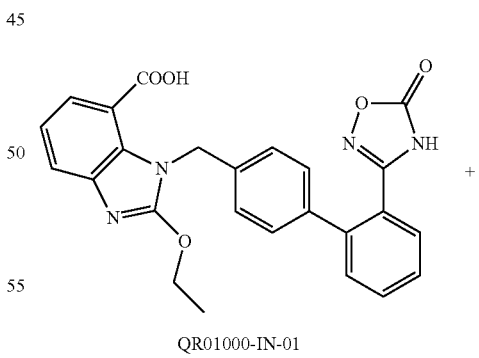

QR01000-IN-01

QR01007-IN-01

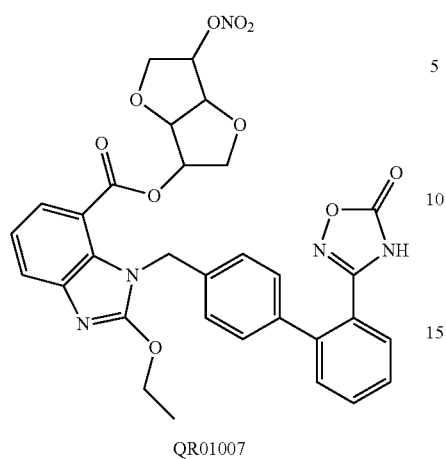

QR01007

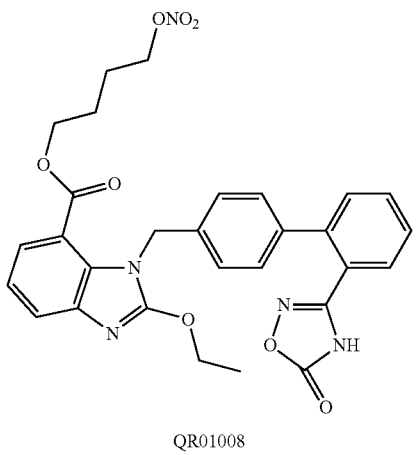

QR01008

The QR01000-IN-01 (2.2 mmol, 1.0 eq.) and the QR01007-IN-01 (2.6 mmol, 1.2 eq.) were dissolved in 20 ml of dimethylformamide, cooled to 10° C. To the resulting solution, potassium carbonate (2.6 mmol, 1.2 eq.), p-toluenesulfonyl chloride (2.6 mmol, 1.2 eq.), and a dimethylaminopyridine catalyst were added and the resulting mixture was stirred for 3 h. After the completion of the reaction, water was added to the reaction solution, extracted with ethyl acetate. The resulting organic layer was washed with water and saturated brine. Crude product was purified by column chromatography to give the title compound QR01007, its structure being dually confirmed by LCMS and NMRH spectra.

Example 7

Synthesis of 4-nitrooxybutyl-2-ethoxy-1-{[2'-(5-oxo-4,5-dihydro-1,2,4-oxadiazole)-3-yl)biphenyl-4-yl]methyl}-1H-benzimidazole-7-carboxylate

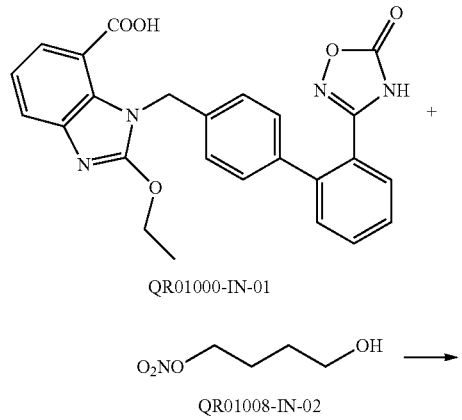

The QR01000-IN-01 (2.2 mmol, 1.0 eq.) and the QR01008-IN-01 (3.3 mmol, 1.5 eq.) were dissolved in 20 ml of dimethylformamide, cooled to 10° C. Then, to the resulting solution, potassium carbonate (2.6 mmol, 1.2 eq.), p-toluenesulfonyl chloride (2.6 mmol, 1.2 eq.), and a dimethylaminopyridine catalyst were added and the resulting mixture was stirred for 3 h. After the completion of the reaction, water was added to the reaction solution, extracted with ethyl acetate. The resulting organic layer was washed with water and saturated brine. Crude product is purified by column chromatography to give the title compound QR01008, its structure being dually confirmed by LCMS and NMRH spectra.

Example 8

Synthesis of 3-(4-phenyl-1,2,5-oxadiazole-2-oxide-3-)methyl-2-ethoxy-1-{[2'-(5-oxo-4,5-dihydro-1,2,4-oxadiazole)-3-yl)biphenyl-4-yl]methyl}-1H-benzimidazole-7-carboxylate

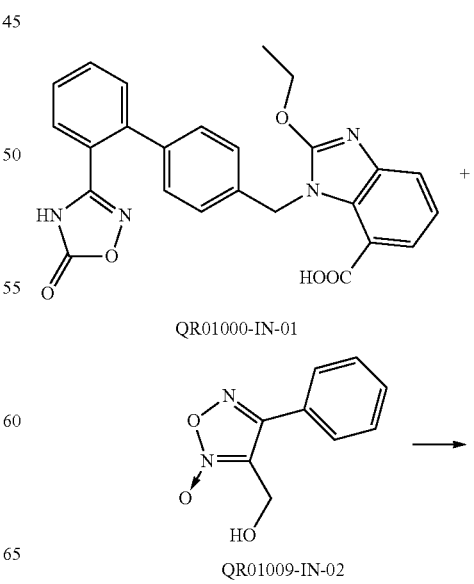

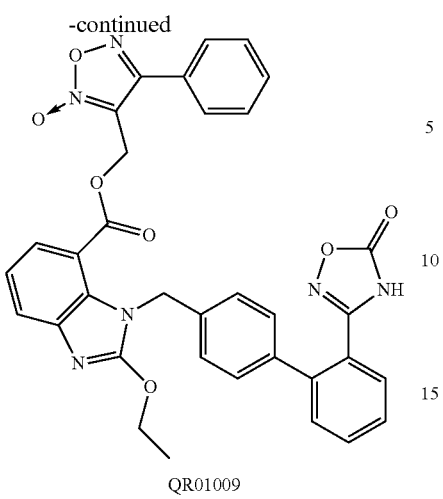

QR01009

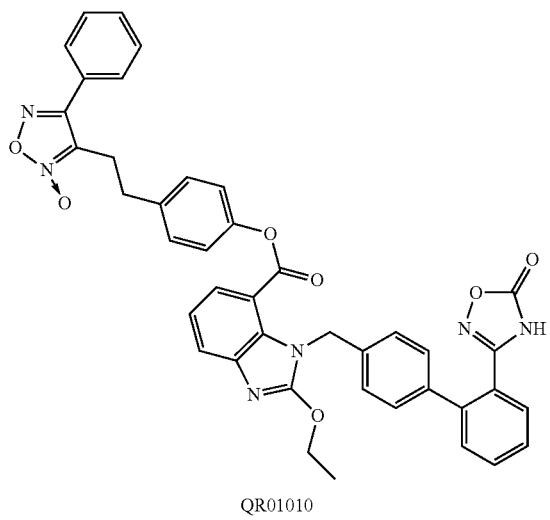

QR01010

The QR01000-IN-01 (2.2 mmol, 1.0 eq.) and the QR01009-IN-01 (2.6 mmol, 1.2 eq.) were dissolved in 20 ml of dimethylformamide, cooled to 10° C. To the resulting solution, potassium carbonate (2.6 mmol, 1.2 eq.), p-toluenesulfonyl chloride (2.6 mmol, 1.2 eq.), and a dimethylaminopyridine catalyst were added and the resulting mixture was stirred for 3 h. After the completion of the reaction, water was added to the reaction solution, extracted with ethyl acetate. The resulting organic layer was washed with water and saturated brine. Crude product is purified by column chromatography to give the title compound QR01009, its structure being dually confirmed by LCMS and NMRH spectra.

Example 9

Synthesis of 3-(4-phenyl-1,2,5-oxadiazole-2-oxide-3-)methyl-2-ethoxy-1-{[2'-(5-oxo-4,5-dihydro-1,2,4-oxadiazole)-3-yl)biphenyl-4-yl]methyl}-1H-benzimidazole-7-carboxylate The QR01000-IN-01 (2.2 mmol, 1.0 eq.) and the QR01010-IN-02 (2.6 mmol, 1.2 eq.) were dissolved in 20 mL of dichloromethane, and dicyclohexyl carbodiimide (4.4 mmol, 2.0 eq.) was added thereto, stirred at room temperature overnight. After the completion of the reaction, water was added to the reaction solution, extracted with ethyl acetate. The resulting organic layer was washed with water and saturated brine. Crude product is purified by column chromatography to give the title compound QR01010, its structure being dually confirmed by LCMS and NMRH spectra.

Example 10

Synthesis 4-(3-benzosulfonyl-1,2,5-oxadiazole-2-oxide-3-)oxybutyl-2-ethoxy-1-{[2'-(5-oxo-4,5-dihydro-1,2,4-oxadiazole)-3-yl)biphenyl-4-yl]methyl}-1H-benzimidazole-7-carboxylate

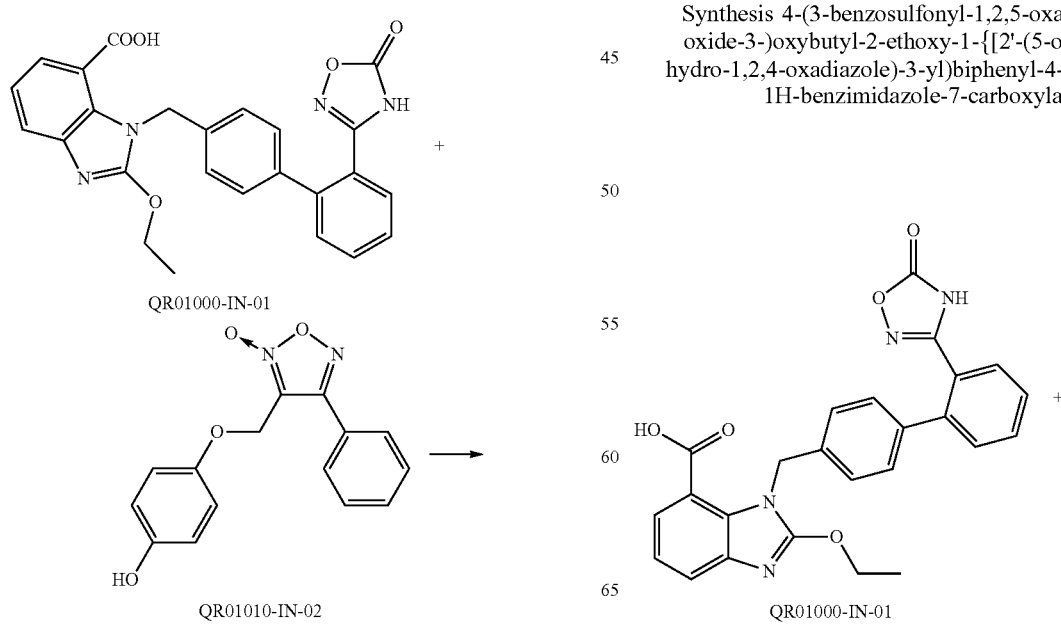

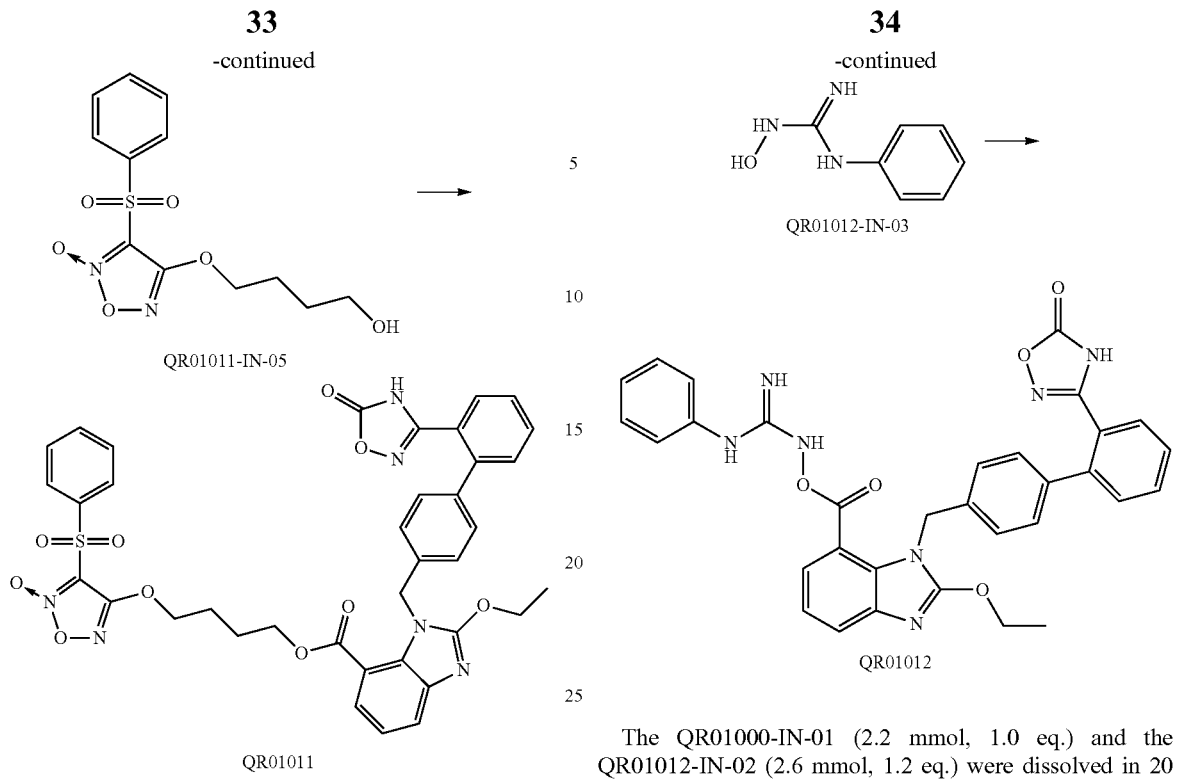

The QR01000-IN-01 (2.2 mmol, 1.0 eq.) and the QR01011-IN-02 (2.6 mmol, 1.2 eq.) were dissolved in 20 mL of dichloromethane, and dicyclohexyl carbodiimide (4.4 mmol, 2.0 eq.) and the dimethylaminopyridine catalyst were added thereto, stirred at room temperature overnight. After the completion of the reaction, water was added to the reaction solution, extracted with dichloromethane. The resulting organic layer was washed with water and saturated brine. Crude product is purified by column chromatography to give the title compound QR01011, its structure being dually confirmed by LCMS and NMRH spectra.

Example 11

Synthesis of 2-ethoxy-1-{[2'-(5-oxo-4,5-dihydro-1,2,4-oxadiazole)-3-yl) biphenyl-4-yl]methyl}-1H-benzimidazole-7-carboxylic acid-(N-phenyl-N'-hydroxyguanidine) ester

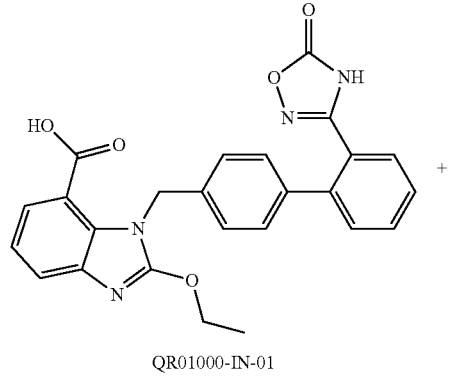

The QR01000-IN-01 (2.2 mmol, 1.0 eq.) and the QR01012-IN-02 (2.6 mmol, 1.2 eq.) were dissolved in 20 mL of dichloromethane, and dicyclohexyl carbodiimide (4.4 mmol, 2.0 eq.) and the catalyst dimethylaminopyridine were added thereto, stirred at room temperature overnight. After the completion of the reaction, water was added to the reaction solution, extracted with dichloromethane. The resulting organic layer was washed with water and saturated brine. Crude product is purified by column chromatography to give the title compound QR01012, its structure being dually confirmed by LCMS and NMRH spectra.

Example 12

Synthesis of 5-methyl-3-thio-1,3-dioxole-4-yl)methyl-2-ethoxy-1-{[2'-(5-oxo-4,5-dihydro-1,2,4-oxadiazole)-3-yl)biphenyl-4-yl]methyl}-1H-benzimidazole-7-carboxylate

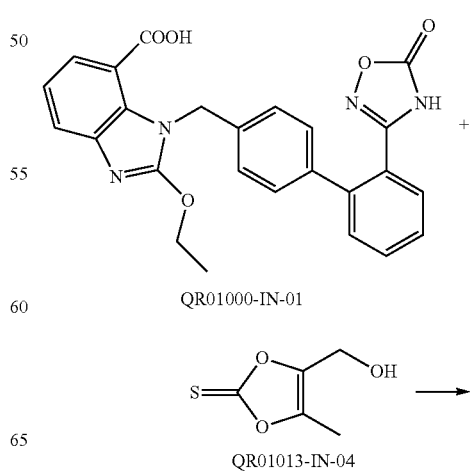

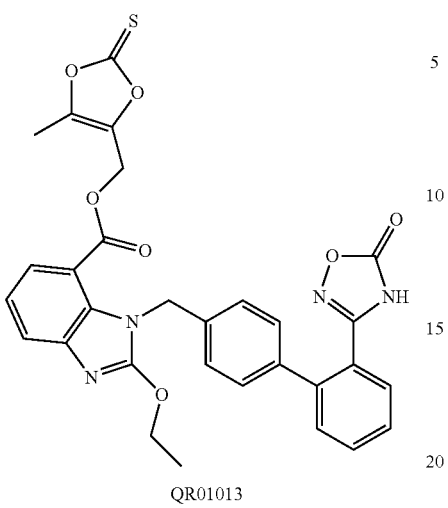

QR01013

The QR01000-IN-01 (2.2 mmol, 1.0 eq.) and the QR01013-IN-01 (2.6 mmol, 1.2 eq) were dissolved in 20 ml of dimethylformamide, cooled to 10° C. To the resulting mixture, potassium carbonate (2.6 mmol, 1.2 eq.), p-toluenesulfonyl chloride (2.6 mmol, 1.2 eq.), and the catalyst dimethylaminopyridine were added and the resulting mixture is stirred for 3 h. After the completion of the reaction, water was added to the reaction solution, extracted with ethyl acetate. The resulting organic layer was washed with water and saturated brine. Crude product is purified by column chromatography to give the title compound QR01013, its structure being dually confirmed by LCMS and NMRH spectra.

Example 13

Synthesis (3-methyl-5,6-dioxy-5,6-dihydro-1,4-dioxa-2-) methyl-2-ethoxy-1-{[2'-(5-oxo-4,5-dihydro-1,2,4-oxadiazole)-3-yl)biphenyl-4-yl]methyl}-1H-benzimidazole-7-carboxylate

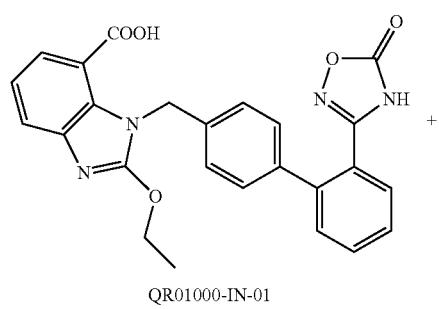

QR01000-IN-01

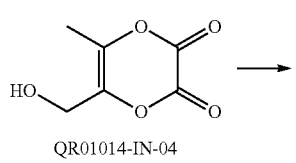

QR01014-IN-04

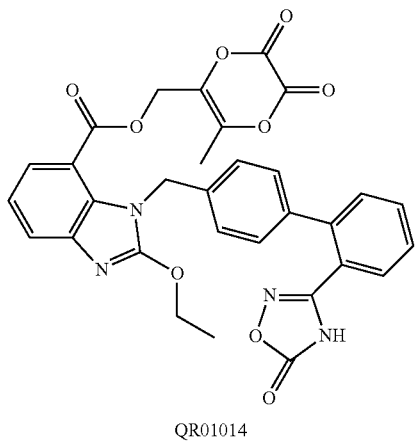

QR01014

The QR01000-IN-01 (2.2 mmol, 1.0 eq.) and the QR01014-IN-01 (2.6 mmol, 1.2 eq.) were dissolved in 20 ml of dimethylformamide, cooled to 10° C. To the resulting mixture, potassium carbonate (2.6 mmol, 1.2 eq.), p-toluenesulfonyl chloride (2.6 mmol, 1.2 eq.), and the catalyst dimethylaminopyridine were added and the resulting mixture is stirred for 3 h. After the completion of the reaction, water was added to the reaction solution, extracted with ethyl acetate. The resulting organic layer was washed with water and saturated brine. Crude product is purified by column chromatography to give the title compound QR01014, its structure being dually confirmed by LCMS and NMRH spectra.

Example 14

Synthesis of 3-[hydroxy-ethyl oxalate]-2-oxo-butyl-2-ethoxy-1-{[2'-(5-oxo-4,5-dihydro-1,2,4-oxadiazole)-3-yl)biphenyl-4-yl]methyl}-1H-benzimidazole-7-carboxylate

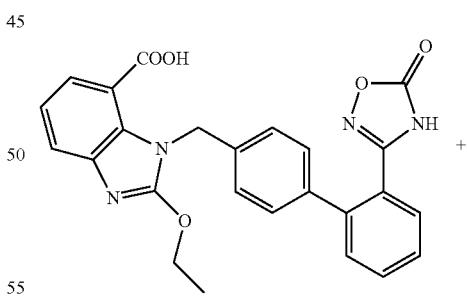

QR01000-IN-01

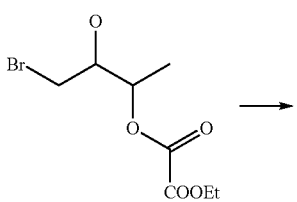

QR01015-IN-01

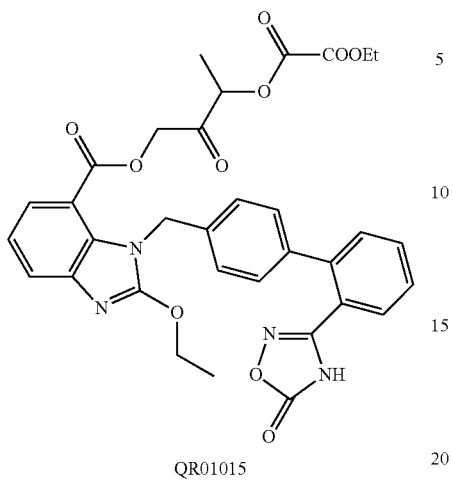

QR01015

The QR01000-IN-01 (2.2 mmol, 1.0 eq.) and the QR01015-IN-01 (3.3 mmol, 1.5 eq) were dissolved in 20 mL N-methylpyrrolidone, and triethylamine (4.4 mmol, 2.0 eq.) was added thereto. The resulting mixture was heated to 65° C. and the TLC was used to monitor the reaction until the reaction is completed. To the reaction solution was added water and ethyl acetate, to perform an extraction, and the resulting organic layer was washed with water and saturated brine. The organic layer was dried and concentrated, and it was purified by column chromatography to give the title compound QR01015, its structure being dually confirmed by LCMS and NMRH spectra.

Example 15

Synthesis of 2-nitrooxyethyl-2-ethoxy-1-{[2'-(5-oxo-4,5-dihydro-1,2,4-oxadiazole)-3-yl)biphenyl-4-yl]methyl}-1H-benzimidazole-7-carboxylate

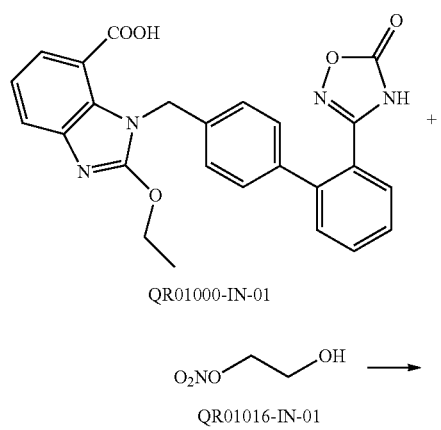

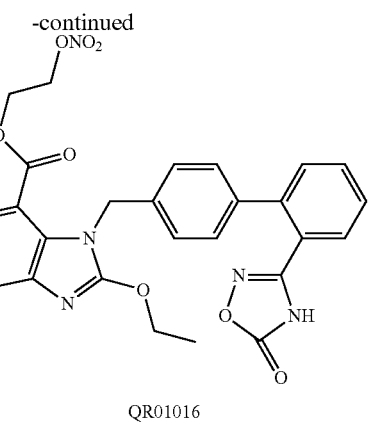

QR01016

The QR01000-IN-01 (2.2 mmol, 1.0 eq.) and the QR01016-IN-01 (3.3 mmol, 1.5 eq) were dissolved in 20 ml of dimethylformamide, cooled to 10° C. To the resulting solution, potassium carbonate (2.6 mmol, 1.2 eq.), p-toluenesulfonyl chloride (2.6 mmol, 1.2 eq.), and the catalyst dimethylaminopyridine were added and the resulting mixture was stirred for 3 h. After the completion of the reaction, water was added to the reaction solution, extracted with ethyl acetate. The resulting organic layer was washed with water and saturated brine. Crude product is purified by column chromatography to give the title compound QR01016, its structure being dually confirmed by LCMS and NMRH spectra.

Example 16

Synthesis of (3,5,6-trimethylpyrazine-2-methoxycarbonyloxy) methyl-2-ethoxy-1-{[2'-(5-oxo-4,5-dihydro-1,2,4-oxadiazole)-3-yl)biphenyl-4-yl] methyl}-1H-benzimidazole-7-carboxylate

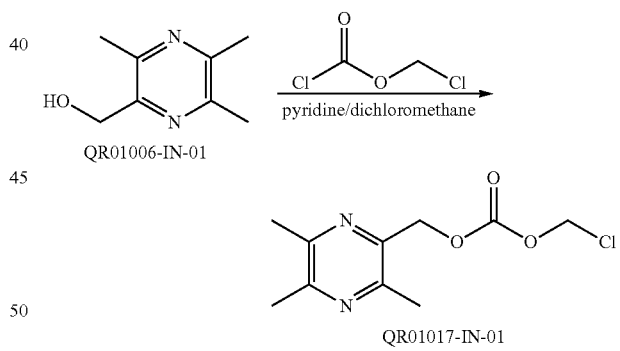

Step (1): to a 50 ml three-necked flask, the QR01006-IN-01 (500 mg, 3.29 mmol), dichloromethane (10 mL), chloromethyl chloroformate (460 mg, 3.6 mmol) were added. The resultant mixture solution was controlled at the temperature of −2° C., and then pyridine (0.32 mL) was dropwise added while controlling the temperature of no greater than 3° C. After the dropwise addition, the reaction solution was heated to room temperature and stirred overnight. The TLC (petroleum ether/ethyl acetate=1:3) was used to monitor the reaction until the raw materials were fully reacted. The reaction solution was filtered, and the resulting filtrate was dried by rotary evaporation, to give 1.1 g of yellow oil. The yellow oil was purified by preparative plate to give 620 mg of yellow liquid, with the yield of 77.3%. LCMS and HNMR spectra can confirm the structure of the target compound.

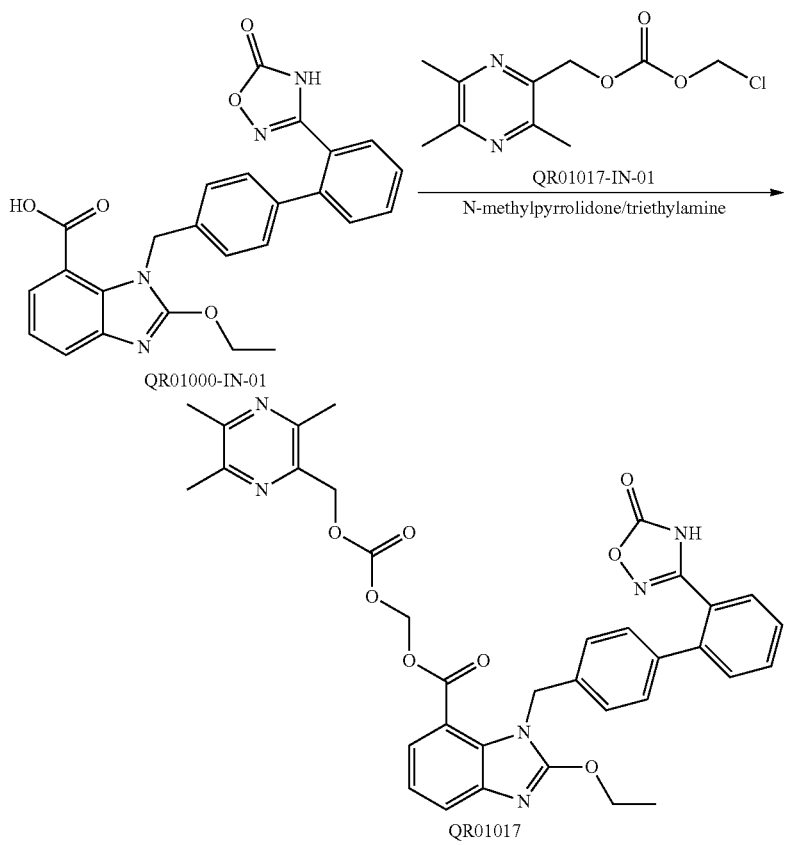

Step (2): to a 50 ml three-necked flask, the QR01000-IN-01 (0.77 g, 1.69 mmol), the QR01017-IN-01 (0.62 g, 2.54 mmol), N-methylpyrrolidone (15 ml) and triethylamine (0.34 g, 3.39 mmol) were added in succession. The resultant mixture solution was stirred at 65° C. for 2 hours, and the TLC (methane dichloride:methanol=10:1) was used to monitor the reaction until it is fully carried out.

Post treatment: the reaction solution was poured into 75 ml of water, and then 1N of HCL was added thereto to adjust the pH in the range of 6 to 7. The resulting solution is a white emulsion liquid. To the solution, methyl t-butyl ether (50 mL) was added to extract the solution, and the extract liquid was washed with saturated brine (50 mL*2) twice, dried with anhydrous Na2SO4, then dried by rotary evaporation, to give 1.2 g yellow liquid. The yellow liquid was purified by a silica-gel column to produce 586 mg of white gum, and the LCMS and HNMR spectra can confirm the structure of the target product QR01017.

Example 17

Synthesis of 1-(3,5,6-trimethylpyrazine-2-methoxycarbonyloxy) ethyl-2-ethoxy-1-{[2'-(5-oxo-4,5-dihydro-1,2,4-oxadiazole)-3-yl)biphenyl-4-yl]methyl}-1H-benzimidazole-7-carboxylate

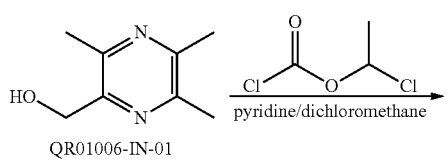

-continued

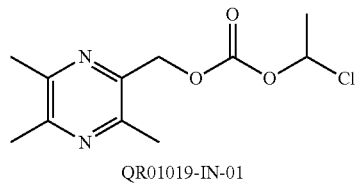

Step (1): to a 50 ml three-necked flask, the QR01006-IN-01 (500 mg, 3.29 mmol), dichloromethane (10 mL), 1-chloroethyl chloroformate (460 mg, 3.6 mmol) were added. The resulting mixture solution was controlled at the temperature of −2° C., and then pyridine (0.32 mL) was dropwise added while controlling the temperature of no greater than 3° C. After the dropwise addition, the reaction solution was heated to room temperature and stirred overnight. The TLC (petroleum ether/ethyl acetate=1:3) was used to monitor the reaction until the raw materials were fully reacted. The reaction solution was filtered, and the resultant filtrate was dried by rotary evaporation, to give 1.1 g of yellow oil. The yellow oil was purified by plate to give 650 mg of yellow liquid. LCMS and HNMR spectra can confirm the structure of the target compound.

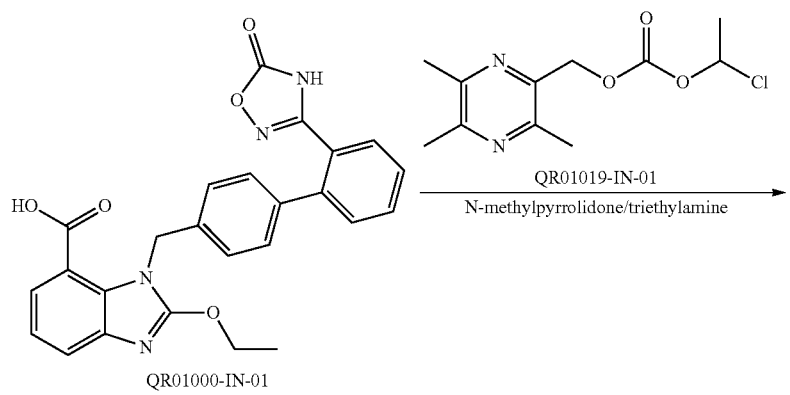

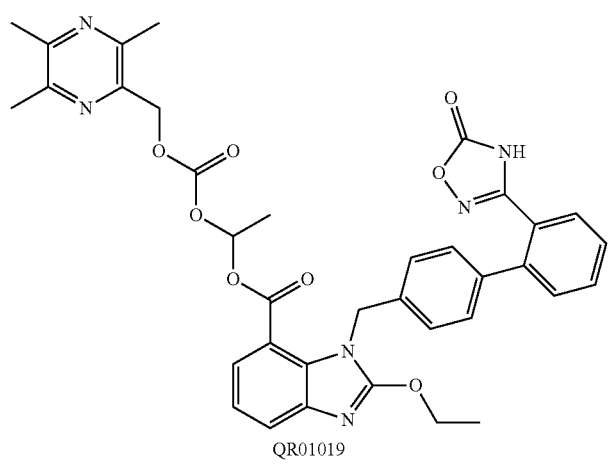

Step (2): to a 50 ml three-necked flask, the QR01000-IN-01 (0.77 g, 1.69 mmol), the QR01019-IN-01 (0.62 g, 2.54 mmol), N-methylpyrrolidone (15 ml) and triethylamine (0.34 g, 3.39 mmol) were added in succession. The resultant mixture solution was stirred at 65° C. for 2 hours, and the TLC (methane dichloride:methanol=10:1) was used to monitor the reaction until it is fully carried out.

Post treatment: the reaction solution was poured into 75 ml of water, and then 1N of HCL was added thereto to adjust the pH in the range of 6 to 7. The resulting solution is a white emulsion liquid. To the solution, methyl t-butyl ether (50 mL) was added to extract the solution, and the extract liquid was washed with saturated brine (50 mL*2) twice, dried with anhydrous Na2SO4, then dried by rotary evaporation, to give 1.2 g yellow liquid. The yellow liquid was purified by a silica-gel column to produce 550 mg of white gum, and the LCMS and HNMR spectra can confirm the structure of the target product QR01019.

Example 18

Synthesis (3-methyl-1,2,5-oxadiazole-2-oxide-3-methoxy-carbonyloxy) methyl-2-ethoxy-1-{[2'-(5-oxo-4,5-dihydro-1,2,4-oxadiazole)-3-yl)biphenyl-4-yl]methyl}-1H-benzimidazole-7-carboxylate

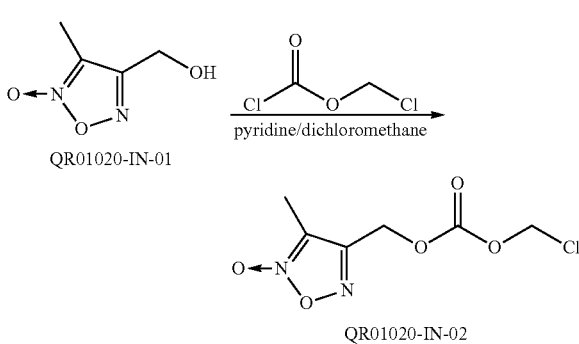

The specific procedures are the same as those in Example 16, except that the compound QR01006-IN-01 is substituted with the compound QR01020-IN-01, and the other operations are unchanged.

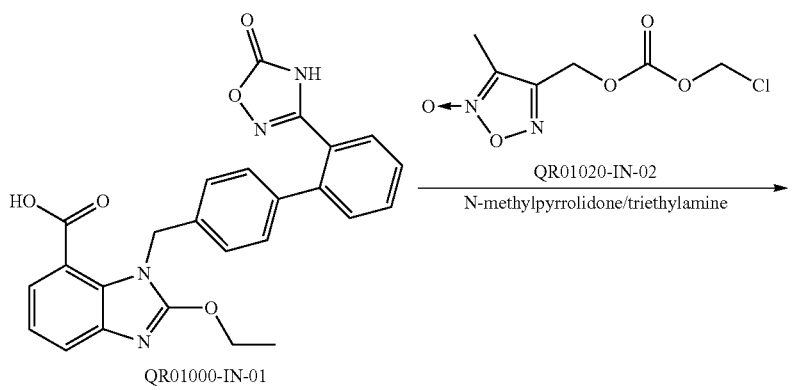

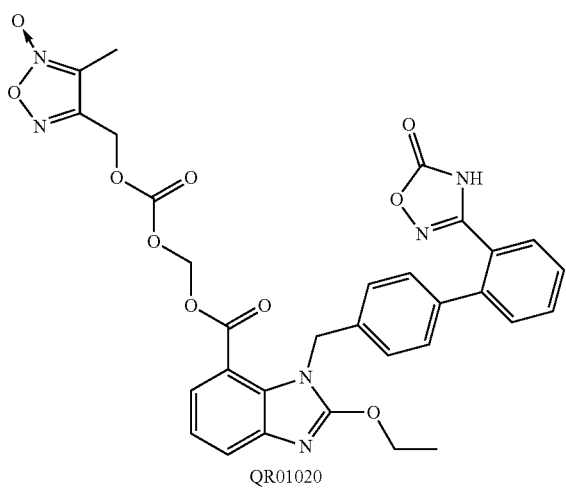

The specific procedures are the same as those in Example 16, except that the compound QR01017-IN-01 is substituted with the compound QR01020-IN-02, and the other operations are unchanged.

LCMS and HNMR spectra can confirm the structure of the target compound QR01020.

Example 19

Synthesis of 1-(3-methyl-1,2,5-oxadiazole-2-oxide-3-methoxy-carbonyloxy) ethyl-2-ethoxy-1-{[2'-(5-oxo-4,5-dihydro-1,2,4-oxadiazole)-3-yl)biphenyl-4-yl]methyl}-1H-benzimidazole-7-carboxylate

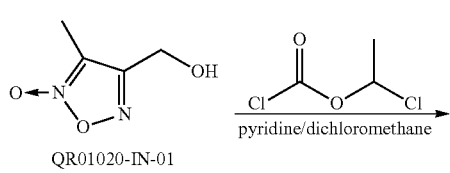

-continued

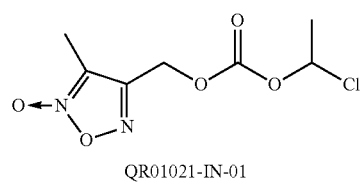

The specific procedures are the same as those in Example 17, except that the compound QR01006-IN-01 is substituted with the compound QR01020-IN-01, and the other operations are unchanged.

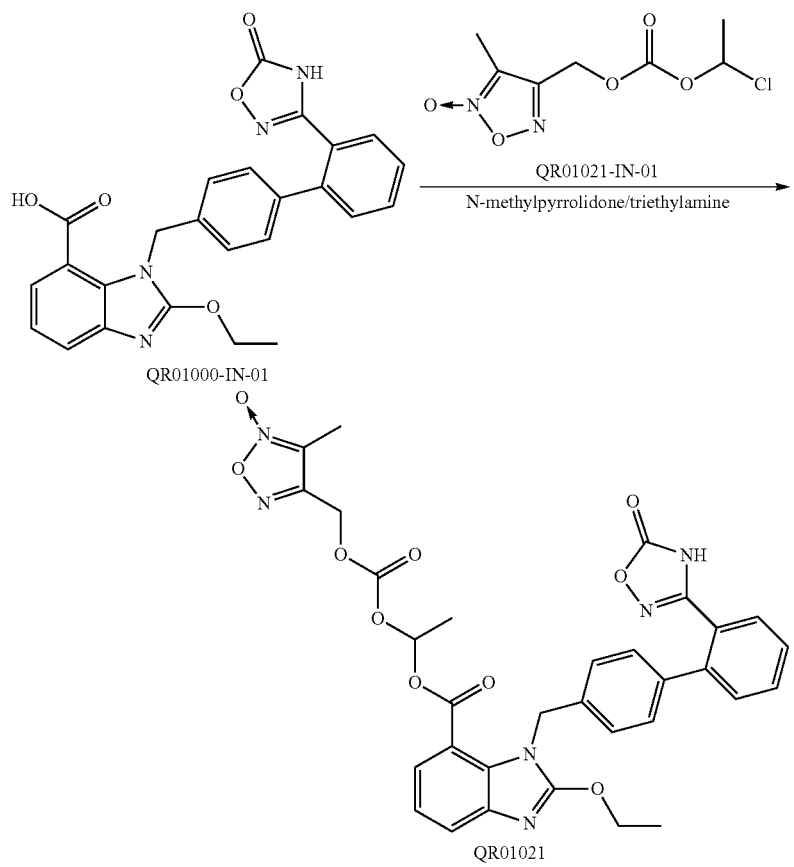

The specific procedures are as those in Example 17, except that the compound QR01019-IN-01 is substituted with the compound QR01021-IN-01, and the other operations are unchanged.

LCMS and HNMR spectra can confirm the structure of the target compound QR01021.

Example 20

Synthesis of 4-(3-methyl-1,2,5-oxadiazole-2-oxide-3-)methyl-2-ethoxy-1-{[2'-(5-oxo-4,5-dihydro-1,2,4-oxadiazole)-3-yl)biphenyl-4-yl]methyl}-1H-benzimidazole-7-carboxylate

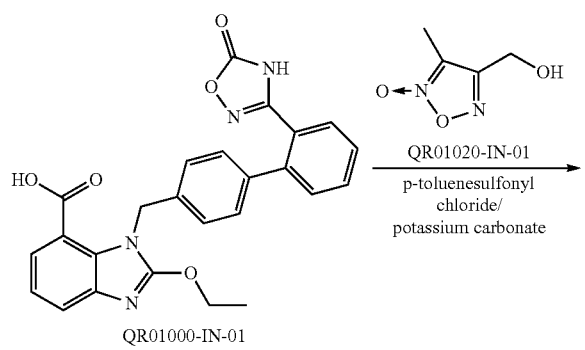

-continued

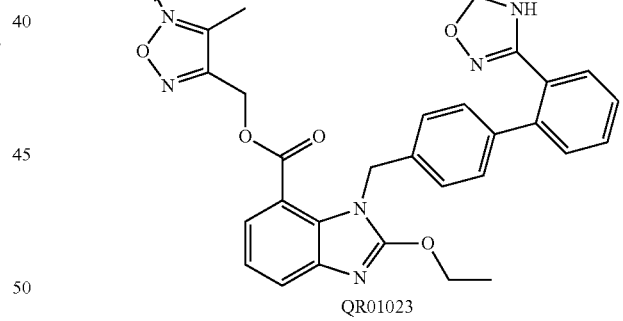

In a 100 ml one-necked flask, the QR01000-IN-01 (1.46 g, 3.2 mmol) was dissolved in 25 mL of N,N-dimethylformamide, and then the QR01020-IN-01 (0.5 g, 3.85 mmol), p-toluenesulfonyl chloride (0.73 g, 3.85 mmol), potassium carbonate (0.88 g, 6.4 mmol) and a catalytic amount of (0.06 g) of N,N-dimethylpyridine amine were added thereto in succession, stirred at room temperature for 3 hours. A new point is detected by the TLC (petroleum ether:ethyl acetate=1:3), and a small quantity of the raw material QR01020-IN-01 was still left.

Post treatment: 50 ml of water were added to the resultant reaction solution, extraction with ethyl acetate (60 ml*3). The resultant organic phase was washed with 100 ml of saturated sodium bicarbonate and 100 ml of saturated brine, and it was dried with anhydrous sodium sulfate, filtrated, and dried by rotary evaporation, to give 1.9 g yellow oily liquid. The yellow oily liquid was separated by column chromatography (petroleum:ethyl acetate=1.5:1 to 1:2), to produce 800 mg of white solid, with the yield of 44.4%.

LCMS and HNMR spectra In FIG. 1 can confirm the structure of the target compound QR01023, and in the LCMS spectrum, MS+: 569.2.

Example 21

Synthesis of 3-(4-methyl-1,2,5-oxadiazole-2-oxide-3-)methyl-2-ethoxy-1-{[2'-(5-oxo-4,5-dihydro-1,2,4-oxadiazole)-3-yl)biphenyl-4-yl]methyl}-1H-benzimidazole-7-carboxylate

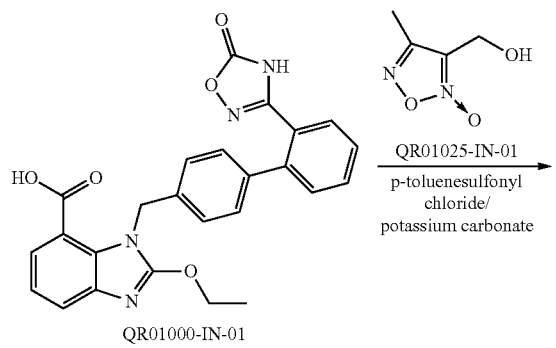

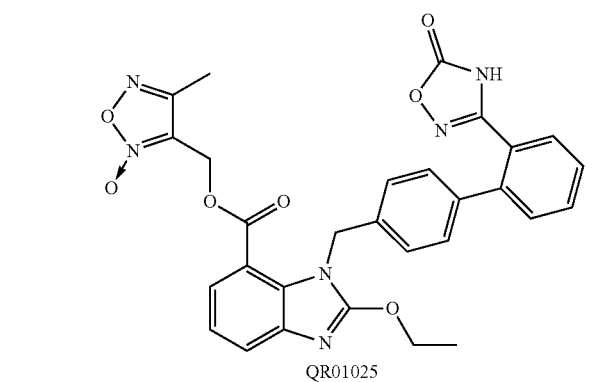

The specific procedures are the same as those in Example 20, except that the compound QR01020-IN-01 is substituted with the compound QR01025-IN-01, and the other operations are unchanged.

LCMS and HNMR spectra can confirm the structure of the target compound QR01025.

Example 22

Synthesis of 4-(3-tert-butyl-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate

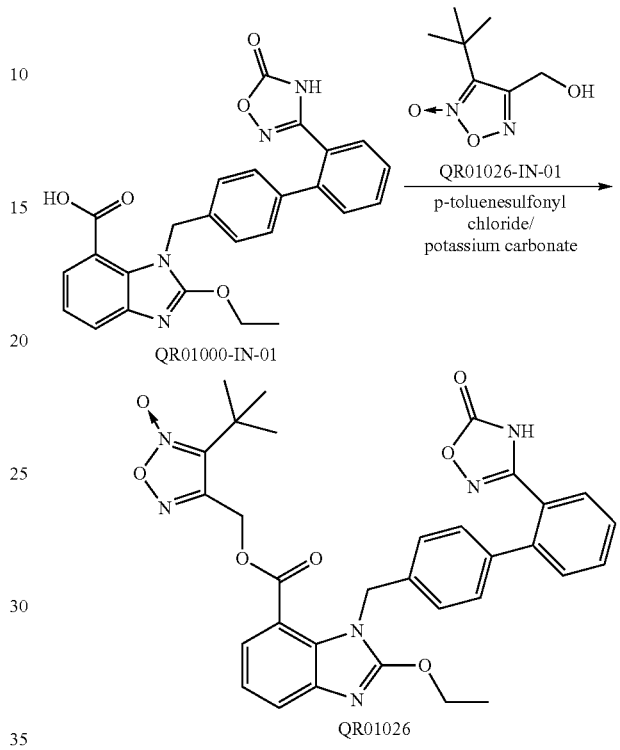

The specific procedures are as the same those in Example 20, except that the compound QR01020-IN-01 is substituted with the compound QR01026-IN-01, and the other operations are unchanged.

LCMS and HNMR spectra can confirm the structure of the target compound QR01026.

Example 23

Synthesis of 1-(3,5,6-trimethylpyrazine-2-methoxycarbonyloxy)isobutyl-2-ethoxy-1-{[2'-(5-oxo-4,5-dihydro-1,2,4-oxadiazole)-3-yl)biphenyl-4-yl]methyl}-1H-benzimidazole-7-carboxylate

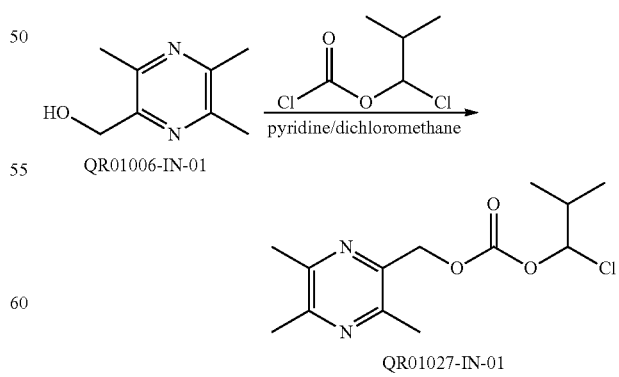

The specifics procedures are the same as those in Example 16, except for that chloromethyl chloroformate is substituted with 1-chloroisobutyl chloroformate, and the other operations are not changed;

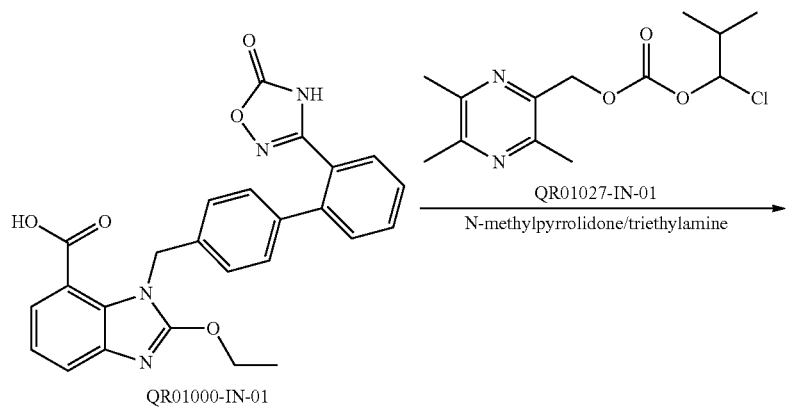

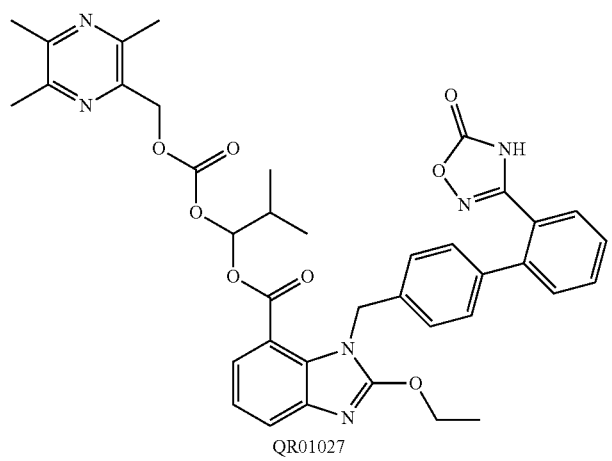

QR01027

The specific procedures are the same as those in Example 16, except that the compound QR01018-IN-01 is substituted with the compound QR01027-IN-01, and the other operations are unchanged.

LCMS and HNMR spectra can confirm the structure of the target compound QR01027.

Example 24

Synthesis of 1-(3,5,6-trimethylpyrazine-2-methoxycarbonyloxy)neopentyl-2-ethoxy-1-{[2'-(5-oxo-4,5-dihydro-1,2,4-oxadiazole)-3-yl)biphenyl-4-yl]methyl}-1H-benzimidazole-7-carboxylate

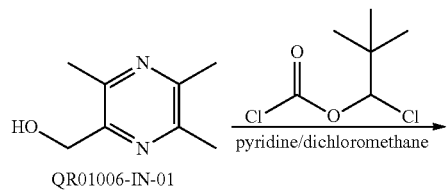

-continued

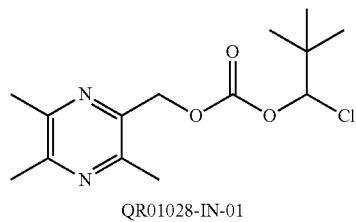

QR01028-IN-01

The specific procedures are the same as those in Example 16, except for that chloromethyl chloroformate is substituted with 1-chloroneopentyl chloroformate, and the other operations are not changed.

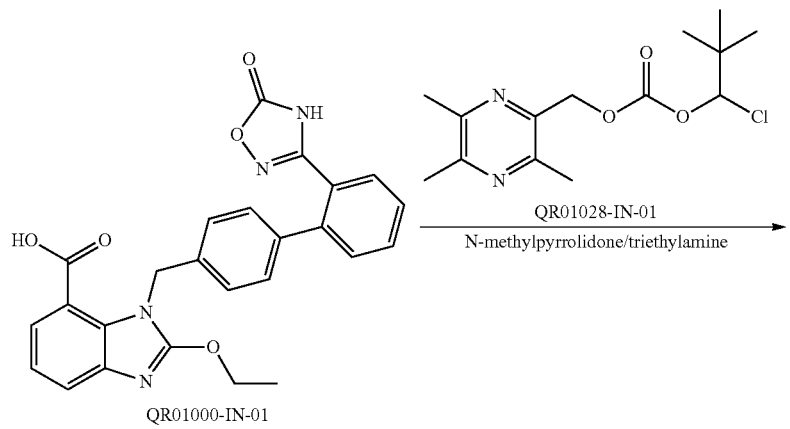

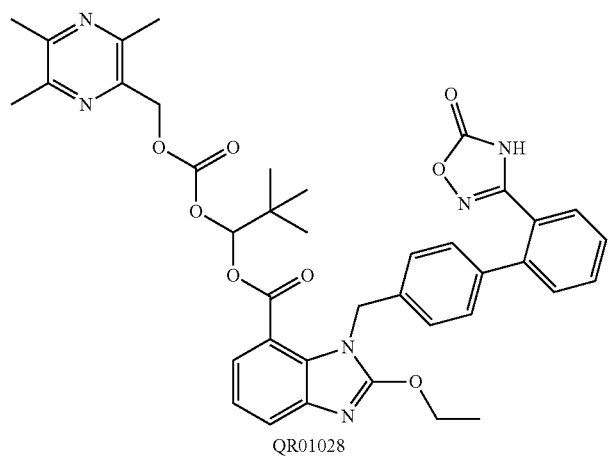

The specific procedures are the same as those in Example 16, except that the compound QR01018-IN-01 was replaced with the compound QR01028-IN-01, and the other operations are unchanged.

LCMS and HNMR spectra can confirm the structure of the target compound QR01028.

Example 25

Synthesis of 1-(6-methylpyrazine-2-methoxy-carbonyloxy)ethyl-2-ethoxy-1-{[2'-(5-oxo-4,5-dihydro-1,2,4-oxadiazole)-3-yl)biphenyl-4-yl]methyl}-1H-benzimidazole-7-carboxylate

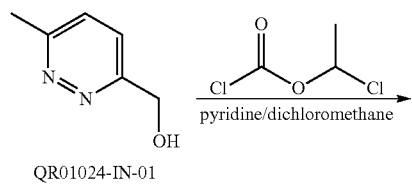

-continued

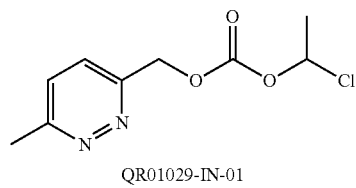

The specific procedures are the same as those in Example 17, except that the compound QR01006-IN-01 is substituted with the compound QR01024-IN-01, and the other operations are unchanged.

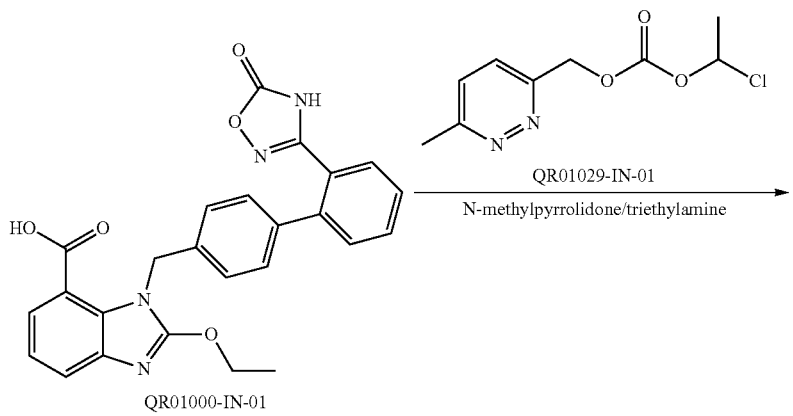

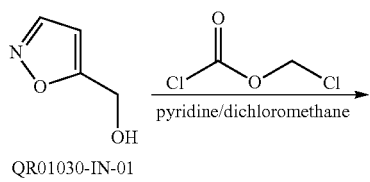

The specific procedures are the same as those in Example 17, except that the compound QR01019-IN-01 is substituted with the compound QR01029-IN-01, and the other operations are unchanged.

LCMS and HNMR spectra can confirm the structure of the target compound QR01029.

Example 26

Synthesis of (isoxazole-5-methoxy-carbonyloxy)methyl-2-ethoxy-1-{[2'-(5-oxo-4,5-dihydro-1,2,4-oxadiazole)-3-yl)biphenyl-4-yl]methyl}-1H-benzimidazole-7-carboxylate -continued The specific procedures are the same as those in Example 16, except that the compound QR01006-IN-01 is substituted with the compound QR01030-IN-01, and the other operations are unchanged.

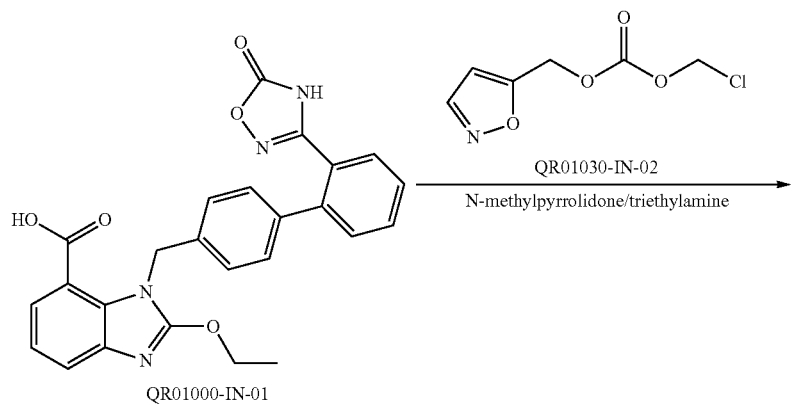

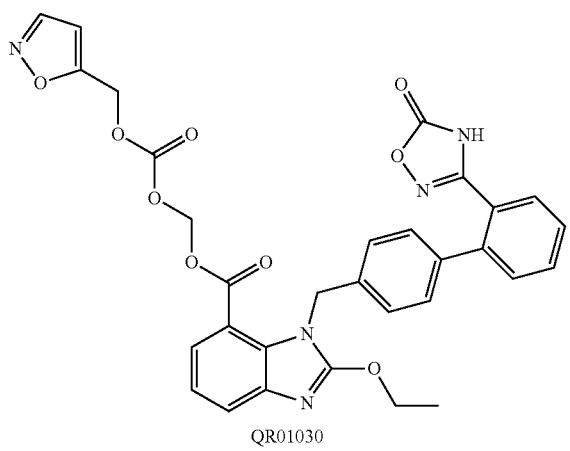

The specific procedures are the same as those in Example 16, except that the compound QR01017-IN-01 is substituted with the compound QR01030-IN-01, and the other operations are unchanged.

LCMS and HNMR spectra can confirm the structure of the target compound QR01030.

Example 27

Synthesis of (1-methylimidazole-4-methoxy-carbonyloxy)methyl-2-ethoxy-1-{[2'-(5-oxo-4,5-dihydro-1,2,4-oxadiazole)-3-yl)biphenyl-4-yl]methyl}-1H-benzimidazole-7-carboxylate

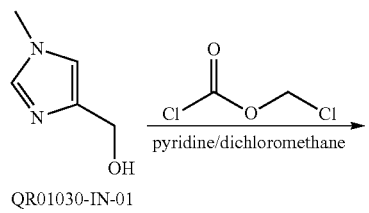

-continued

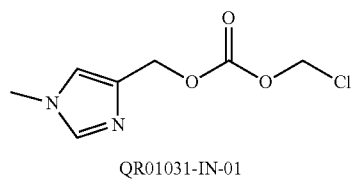

The specific procedures are the same as those in Example 16, except that the compound QR01006-IN-01 is substituted with the compound QR01030-IN-01, and the other operations are unchanged.

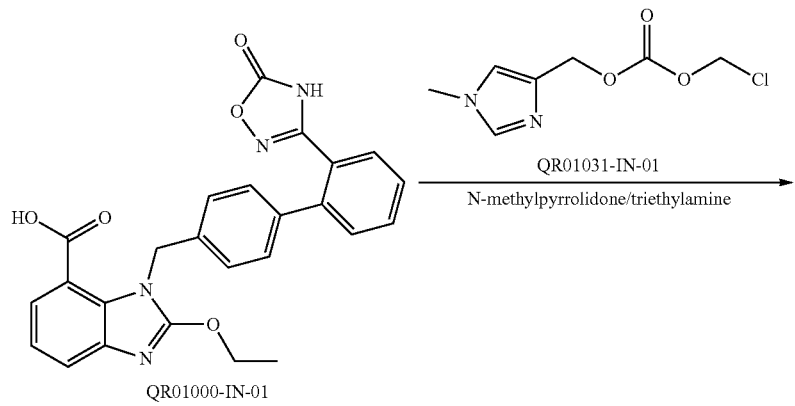

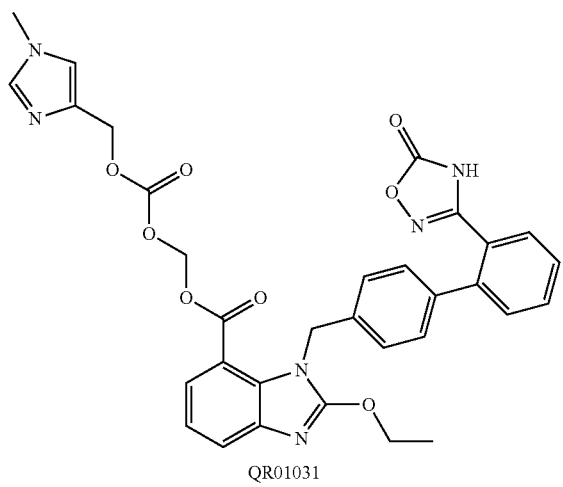

The specific procedures are as those in Example 16, except that the compound QR01017-IN-01 is substituted with the compound QR01031-IN-01, and the other operations are unchanged.

LCMS and HNMR spectra can confirm the structure of the target compound QR01031.

Example 28

Synthesis of (1-methylpyrazine-3-methoxy-carbonyloxy)methyl-2-ethoxy-1-{[2'-(5-oxo-4,5-dihydro-1,2,4-oxadiazole)-3-yl)biphenyl-4-yl]methyl}-1H-benzimidazole-7-carboxylate

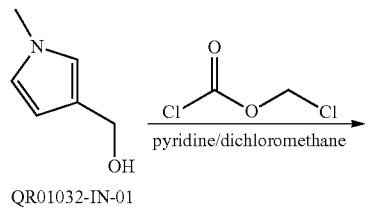

-continued

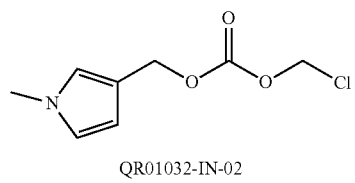

The specific procedures are the same as those in Example 16, except that the compound QR01006-IN-01 is substituted with the compound QR01032-IN-01, and the other operations are unchanged.

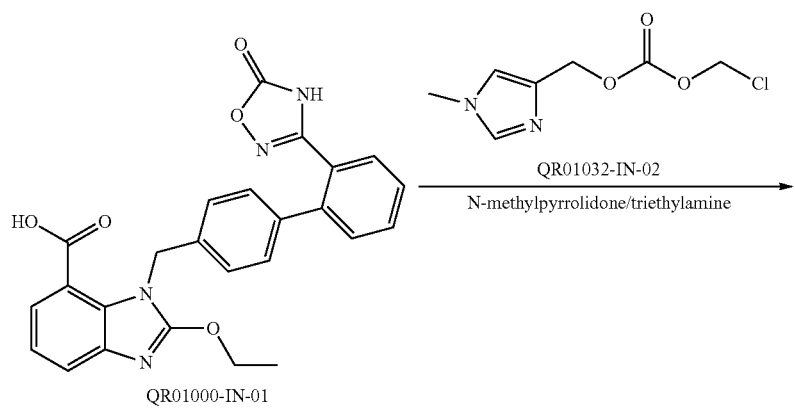

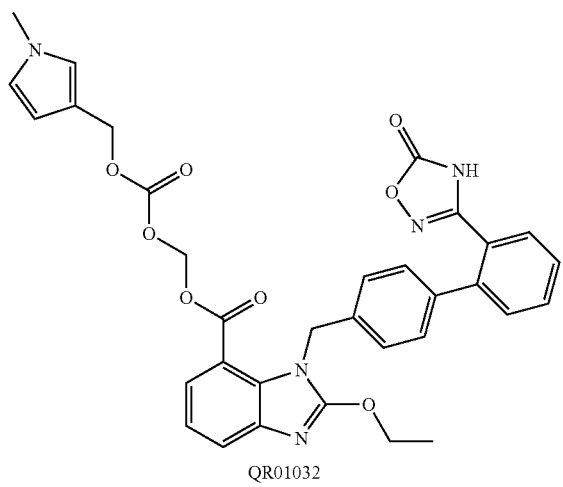

The specific procedures are the same as those in Example 16, except that the compound QR01017-IN-01 is substituted with the compound QR01032-IN-01, and the other operations are unchanged.

LCMS and HNMR spectra can confirm the structure of the target compound QR01032.

Example 29

Synthesis of 1-(1-methylpyrazine-3-methoxy-carbonyloxy)ethyl-2-ethoxy-1-{[2'-(5-oxo-4,5-dihydro-1,2,4-oxadiazole)-3-yl)biphenyl-4-yl]methyl}-1H-benzimidazole-7-carboxylate

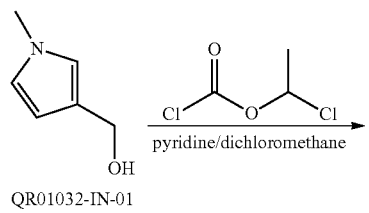

-continued

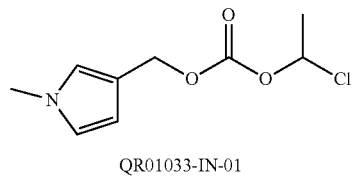

The specific procedures are the same as those in Example 17, except that the compound QR01006-IN-01 is substituted with the compound QR01032-IN-01, and the other operations are unchanged.

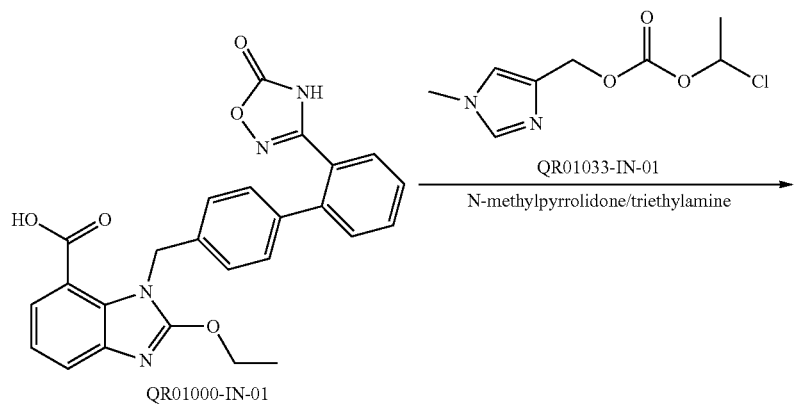

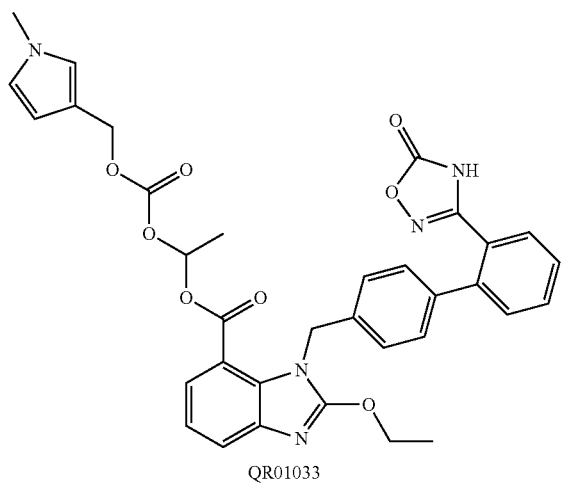

The specific procedures are the same as those in Example 17, except that the compound QR01019-IN-01 is substituted with the compound QR01033-IN-01, and the other operations are unchanged.

LCMS and HNMR spectra can confirm the structure of the target compound QR01033.

Example 30

Synthesis of (4-(3-nitratemethyl-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate

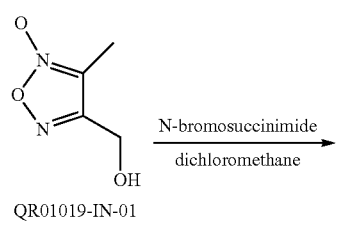

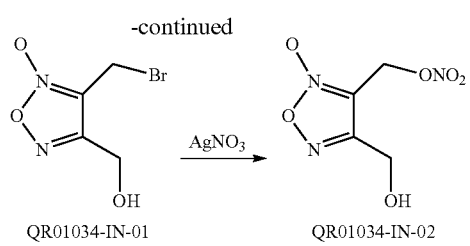

In a 100 mL one-necked flask, the QR01019-IN-01 (0.05 mol) was dissolved in dichloromethane (50 mL), and then N-bromosuccinimide (0.06 mol) and 5 mole % of benzoyl peroxide were added thereto, heated to reflux for 5 hours. The reaction was monitored by the TLC until the raw materials disappeared.

Post treatment: 50 mL of saturated sodium bicarbonate was added to quench the reaction. The reaction mixture was extracted with dichloromethane (60 mL*3), and the extract liquid was washed with 100 ml of saturated brine. Then, the extract liquid was dried with anhydrous sodium sulfate, filtrated, and dried by rotary evaporation, to give 6.5 g yellow oil. The yellow oil is separated by column chromatography, to produce 2.0 g of the compound QR01034-IN-01.

In a 100 mL one-necked flask, the QR01034-IN-01 (0.0048 mol) was dissolved in acetonitrile (50 mL), and then silver nitrate (0.0055 mol) was added thereto. The reaction mixture was heated to reflux for 0.5 h, and the reaction was monitored by the TLC until the raw materials disappeared.

Post treatment: 50 mL of water was added to quench the reaction. The reaction mixture was extracted with methane dichloride (60 mL*3), and the extract liquid was washed with 100 ml of saturated brine. Then, the extract liquid was dried with anhydrous sodium sulfate, filtrated, and dried by rotary evaporation, to give 0.9 g yellow oily liquid. The yellow oily liquid was separated by column chromatography, to produce 630 mg of the compound QR01034-IN-02.

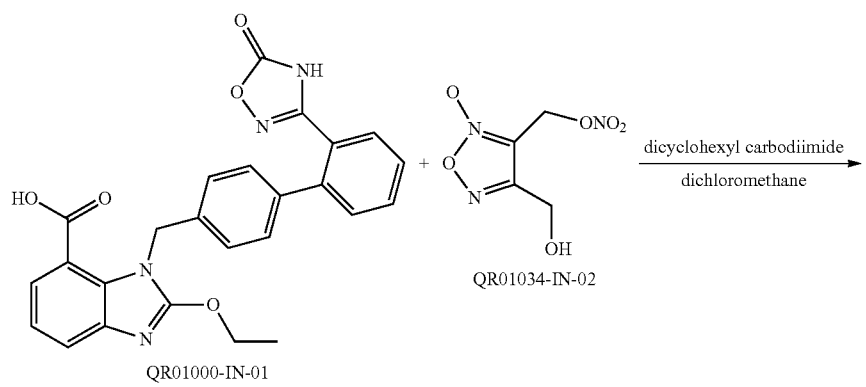

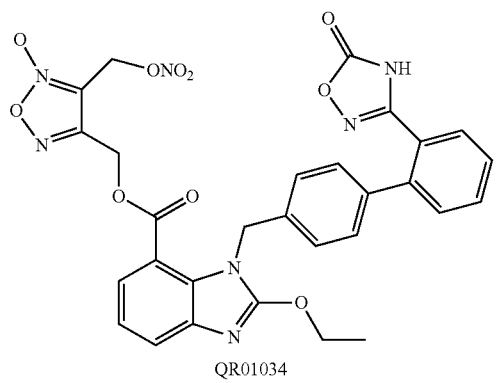

The QR01000-IN-01 (2.2 mmol, 1.0 eq.) and the QR01011-IN-02 (2.6 mmol, 1.2 eq.) were dissolved in 20 mL of dichloromethane, and then dicyclohexyl carbodiimide (4.4 mmol, 2.0 eq.) and the catalyst dimethylaminopyridine were added thereto and stirred at room temperature overnight. After the completion of the reaction, water was added to the reaction solution, extracted with ethyl acetate. The resulting organic layer was washed with water and saturated brine. Crude product was purified by column chromatography to give the title compound QR01034, its structure being confirmed by LCMS and NMRH spectra.

Example 31

Synthesis of 4-{2-ethoxy-1-[2'-(5-oxo-4,5-dihydro-1,2,4-oxadiazole)-3-yl) biphenyl-4-yl]methyl}-1H-benzimidazole-7-carboxylate-5,6-dihydro-4H-cyclopentyl[c]{[1,2,5]oxadiazole-2-oxide}-1-methyl

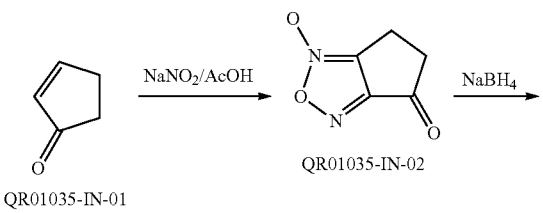

-continued

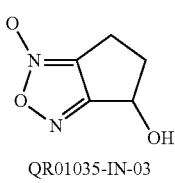

To a 100 mL three-necked flask, the QR01035-IN-01 (0.0071 mol) was added, and then 10 ml of acetic acid and saturated NaNO₂ solution (0.25 mol of NaNO₂ was dissolved in 21 mL of water) were added thereto slowly while controlling the temperature not greater than 20° C. The reaction was monitored by the TLC (PE:EA=1:1) to detect that two new points were formed, and the raw materials were fully reacted. Post treatment: 50 mL of water were added to the reaction solution, and then dichloromethane (100 mL*3) was added thereto to extract the reaction solution. The resultant organic phases were merged and washed with water (100 mL). The washed organic phase was dried with anhydrous Na₂SO₄, then dried by rotary evaporation, to give 7.2 g yellow oil with the yield of 78.8%.

In a 100 ml three-necked flask, the QR01035-IN-02 (0.023 mol) was dissolved in 10 mL of MeOH, and by controlling the temperature at −10° C., NaBH₄ solid (0.047 mol) was slowly added thereto. Then, by controlling the temperature not greater than 10° C., the addition of NaBH₄ solid was completed, and thereafter, the reaction solution was heated to 10° C. to react for 2 hours. The reaction was monitored by the TLC (petroleum ether:ethyl acetate=1:1) until the raw materials completely reacted. Post treatment: 40 mL of water was added dropwise slowly to the reaction solution by controlling the temperature at 0° C., and the temperature was controlled not to exceed 10° C., until the addition was completed. Ethyl acetate (100 mL*2) was added thereto to extract the reaction solution. The resultant organic phases were merged and dried with anhydrous sodium sulfate, and the dried organic phase was dried by rotary evaporation to give 2.2 g yellow liquid with the yield of 72.2%.

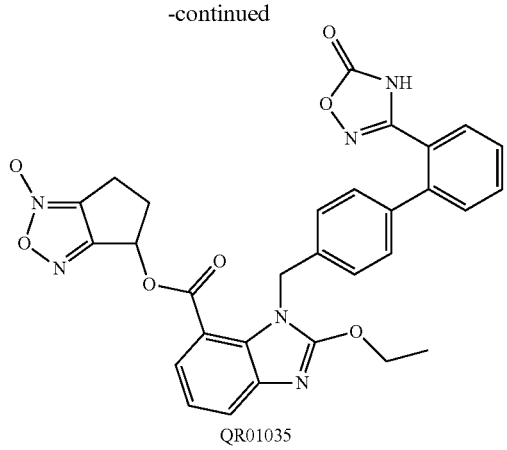

QR01035

The QR01000-IN-01 (2.2 mmol, 1.0 eq.) and the QR01035-IN-01 (2.6 mmol, 1.2 eq.) were dissolved in 20 ml of dimethylformamide, and the resultant solution is cooled to 10° C. Then, potassium carbonate (2.6 mmol, 1.2 eq.), p-toluenesulfonyl chloride (2.6 mmol, 1.2 eq.), and the catalyst dimethylaminopyridine were added to the solution, and the resultant mixture was stirred for 3 h. After the completion of the reaction, water was added to the reaction solution, extracted with ethyl acetate. The resulting organic layer was washed with water and saturated brine. Crude product was purified by column chromatography to give the title compound QR01035, its structure being confirmed by LCMS and NMRH spectra.

Example 32

Synthesis of 4-(3-cyano-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate

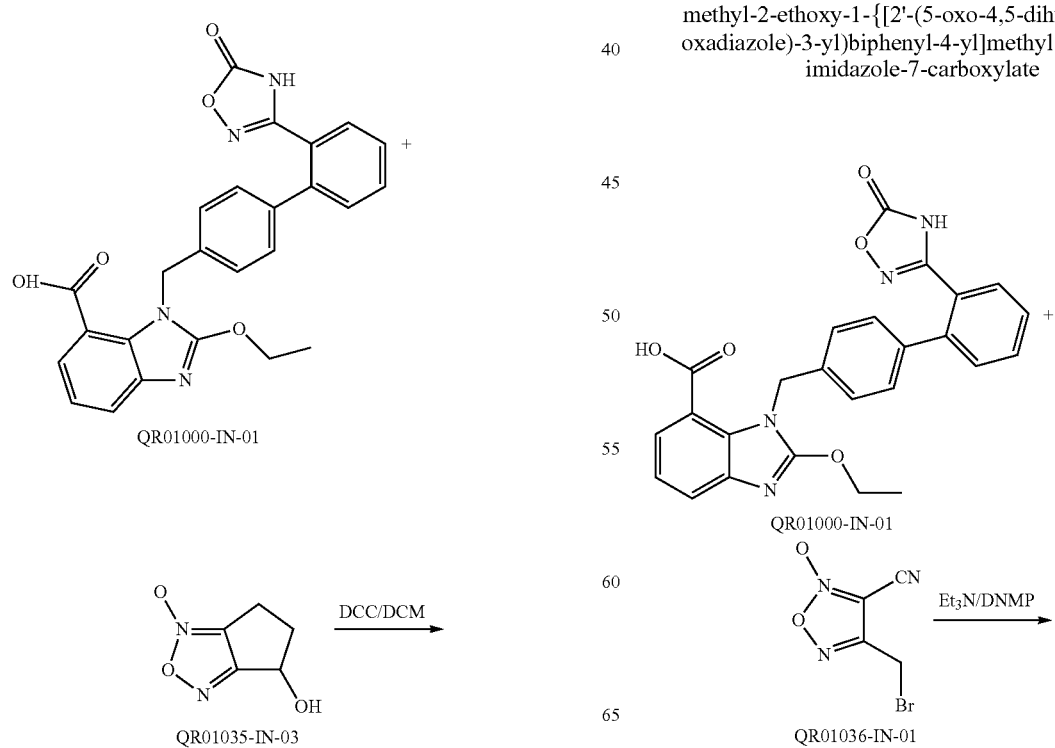

-continued

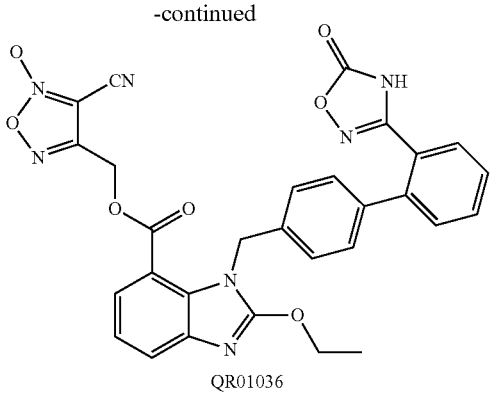

QR01036

The QR01000-IN-01 (2.2 mmol, 1.0 eq.) and the QR01036-IN-01 (3.3 mmol, 1.5 eq.) were dissolved in 20 mL N-methylpyrrolidone, and then triethylamine (4.4 mmol, 2.0 eq.) was added thereto. The resulting mixture was heated to 65° C. and the TLC was used to monitor the reaction until it was completed. To the reaction solution was added water and ethyl acetate, to perform an extraction, and the resulting organic layer was washed with water and saturated brine. The organic layer was dried and concentrated, and it was purified by column chromatography to give the title compound QR01036, its structure being dually confirmed by LCMS and NMRH spectra.

(Note: as to the preparation of the QR01036-IN-01, please see Medicinal Chemistry Research, 11(6), 322-332; 2002 for the reference).

Example 33

Synthesis of potassium salt of the QR01019: potassium 1-(3,5,6-trimethylpyrazine-2-methoxy-carbonyloxy)ethyl-2-ethoxy-1-{[2'-(5-oxo-4,5-dihydro-1,2,4-oxadiazole)-3-yl)biphenyl-4-yl]methyl}-1H-benzimidazole-7-carboxylate The QR01019 (1.0 g) was dissolved in acetone (20 ml) while being refluxed to form a solution. After the solution was cooled to 50° C., a solution of potassium 2-ethyl hexanoate (0.30 g) in acetone (1 ml) was slowly dropped thereto. The reaction mixture was cooled slowly to 0° C., and then it was kept at the temperature to be stirred for 5 hour. The resultant mixture was filtered, dried under vacuum at 60° C., and the resultant solid was the potassium salt of the QR01019.

Test Example

The compounds of the general formula I according to the invention (the products QR01002-QR01036 as prepared in Examples 1-32) were tested to study their Pharmacology and Pharmacodynamics.

1. Effect on Reducing Blood Pressure of Renovascular Hypertensive Rats by Single Oral Administration of Benzimidazole Derivatives Wistar rats (provided by Hubei Province Disease Prevention Control Center, Wuhan, Hubei), male, weighted of 180 to 200 g, were randomly classified into 5 groups, including negative control group (0.5% CMC-Na), positive control group (Azilsartan medoxomil as a positive drug, synthesized by Wuhan Qirui Pharmaceuticals Optics Valley Biolake Development Center, Pharmaceutical Chemical Department) and three groups with the test compounds QR01002-QR01036 in low, middle, and high dosages (0.5, 1.0, 2.0 mg/kg, all drugs were formulated in 0.5% CMC-Na), 6-8 animals per group. The unilateral renal arteries of the rats were ligated to form two-kidney, one-clip renovascular hypertensive rat (RHR) models. After the surgery, the blood pressure was measured weekly, and the measurement continued for 4 weeks. The rats whose blood pressures were steadily elevated by 4 kPa were successfully modeled rats. Before measuring blood pressure, the rat tails were heated by using a cyclic water bath tail sleeve at 39° C. to expand tail vessel, and thereafter, a tail sleeve method (BP2010A noninvasive blood pressure meter, Beijing Jiandeer Technology Limited Corporation, No. 1, Shangdi $10^{th}$ Street, Haidian District, Beijing) was used to measure blood pressures and heart rates of the rates before the administrations and at 1, 3, 5, 7, and 10 hours after oral administration, and each of the time points was measured three times to take the mean value. Maximum Blood pressure reduction (%)=maximum blood pressure reduction value after the administration/blood pressure value before the administration*100%.

TABLE 1

Effects on reducing blood pressure of renovascular hypertensive rats by oral administration of benzimidazole derivatives QR01002-QR01036 and positive drugs

| Compound | Maximum blood pressure reduction | Variations on heart rate |
| --- | --- | --- |
| Negative control, 0.5% CMC-Na, 1.0 ml/kg | 4.6 ± 1.2% | −5 ± 2% |
| Azilsartan medoxomil, 1.0 mg/kg | 30 ± 3.8% | −7 ± 3% |
| QR01002 | | |
| 0.5 mg/kg | 12 ± 2.4% | −5 ± 4% |
| 1.0 mg/kg | 15 ± 1.8% | −8 ± 3% |
| 2.0 mg/kg | 19 ± 4.2% | −6 ± 4% |
| QR01003 | | |
| 0.5 mg/kg | 15 ± 1.8% | +2 ± 1% |
| 1.0 mg/kg | 28 ± 2.9% | −3 ± 2% |
| 2.0 mg/kg | 36 ± 4.3% | −5 ± 2% |
| QR01004 | | |
| 0.5 mg/kg | 7 ± 1.2% | 0 ± 2% |
| 1.0 mg/kg | 10 ± 2.3% | −5 ± 3% |
| 2.0 mg/kg | 12 ± 3.4% | −3 ± 1% |
| QR01005 | | |
| 0.5 mg/kg | 16 ± 3.2% | −10 ± 3% |
| 1.0 mg/kg | 36 ± 3.1% | −21 ± 6% |
| 2.0 mg/kg | 43 ± 3.5% | −25 ± 6% |
| QR01006 | | |
| 0.5 mg/kg | 14 ± 3.4% | −4 ± 2% |
| 1.0 mg/kg | 18 ± 3.6% | −5 ± 3% |
| 2.0 mg/kg | 24 ± 4.1% | −5 ± 3% |
| QR01007 | | |
| 0.5 mg/kg | 10 ± 1.5% | −3 ± 1% |
| 1.0 mg/kg | 12 ± 2.0% | −8 ± 3% |
| 2.0 mg/kg | 18 ± 3.5% | −5 ± 2% |
| QR01008 | | |
| 0.5 mg/kg | 17 ± 3.1% | −8 ± 5% |
| 1.0 mg/kg | 28 ± 3.4% | −15 ± 3% |
| 2.0 mg/kg | 35 ± 3.4% | −18 ± 5% |
| QR01009 | | |
| 0.5 mg/kg | 22 ± 2.8% | −12 ± 4% |
| 1.0 mg/kg | 36 ± 3.2% | −25 ± 5% |
| 2.0 mg/kg | 43 ± 6.7% | −28 ± 8% |

TABLE 1-continued

Effects on reducing blood pressure of renovascular hypertensive rats by oral administration of benzimidazole derivatives QR01002-QR01036 and positive drugs

| Compound | Maximum blood pressure reduction | Variations on heart rate |
|---|---|---|
| QR01010 | | |
| 0.5 mg/kg | 21 ± 4.7% | +5 ± 2% |
| 1.0 mg/kg | 26 ± 5.4% | −3 ± 1% |
| 2.0 mg/kg | 30 ± 3.6% | −5 ± 3% |
| QR01011 | | |
| 0.5 mg/kg | 16 ± 4.3% | −5 ± 3% |
| 1.0 mg/kg | 28 ± 1.3% | −8 ± 6% |
| 2.0 mg/kg | 29 ± 4.0% | −6 ± 4% |
| QR01012 | | |
| 0.5 mg/kg | 17 ± 3.7% | +2 ± 2% |
| 1.0 mg/kg | 22 ± 1.0% | −3 ± 4% |
| 2.0 mg/kg | 27 ± 2.8% | −5 ± 2% |
| QR01013 | | |
| 0.5 mg/kg | 16 ± 3.0% | −6 ± 4% |
| 1.0 mg/kg | 25 ± 4.5% | −8 ± 3% |
| 2.0 mg/kg | 34 ± 7.1% | −10 ± 5% |
| QR01014 | | |
| 0.5 mg/kg | 16 ± 3.5% | −2 ± 3% |
| 1.0 mg/kg | 21 ± 4.3% | −4 ± 2% |
| 2.0 mg/kg | 26 ± 2.1% | −4 ± 5% |
| QR01015 | | |
| 0.5 mg/kg | 10 ± 1.5% | +4 ± 1% |
| 1.0 mg/kg | 12 ± 2.0% | +2 ± 3% |
| 2.0 mg/kg | 18 ± 3.5% | +3 ± 2% |
| QR01016 | | |
| 0.5 mg/kg | 11 ± 3.1% | +1 ± 3% |
| 1.0 mg/kg | 12 ± 9.2% | +5 ± 2% |
| 2.0 mg/kg | 15 ± 6.5% | +4 ± 3% |
| QR01017 | | |
| 0.5 mg/kg | 25 ± 6.2% | 10 ± 3% |
| 1.0 mg/kg | 38 ± 3.5% | 22 ± 6% |
| 2.0 mg/kg | 46 ± 2.6% | 28 ± 5% |
| QR01019 | | |
| 0.5 mg/kg | 24 ± 4.0% | 12 ± 4% |
| 1.0 mg/kg | 38 ± 3.8% | 25 ± 8% |
| 2.0 mg/kg | 45 ± 7.5% | 28 ± 6% |
| QR01020 | | |
| 0.5 mg/kg | 25 ± 4.3% | −15 ± 3% |
| 1.0 mg/kg | 34 ± 6.8% | −28 ± 6% |
| 2.0 mg/kg | 48 ± 2.6% | −25 ± 8% |
| QR01021 | | |
| 0.5 mg/kg | 15 ± 2.1% | −6 ± 5% |
| 1.0 mg/kg | 28 ± 4.5% | −3 ± 6% |
| 2.0 mg/kg | 32 ± 5.2% | −12 ± 5% |
| QR01023 | | |
| 0.5 mg/kg | 18 ± 2.3% | −8 ± 5% |
| 1.0 mg/kg | 32 ± 8.1% | −16 ± 7% |
| 2.0 mg/kg | 42 ± 4.6% | −23 ± 6% |
| QR01025 | | |
| 0.5 mg/kg | 18 ± 3.4% | 4 ± 6% |
| 1.0 mg/kg | 22 ± 4.5% | −7 ± 5% |
| 2.0 mg/kg | 28 ± 3.2% | −7 ± 3% |
| QR01026 | | |
| 0.5 mg/kg | 16 ± 2.8% | −8 ± 6% |
| 1.0 mg/kg | 24 ± 6.5% | −10 ± 5% |
| 2.0 mg/kg | 31 ± 2.8% | −10 ± 6% |
| QR01027 | | |
| 0.5 mg/kg | 14 ± 2.0% | −2 ± 3% |
| 1.0 mg/kg | 18 ± 2.9% | −5 ± 3% |
| 2.0 mg/kg | 23 ± 4.6% | −6 ± 4% |
| QR01028 | | |
| 0.5 mg/kg | 15 ± 0.9% | −6 ± 2% |
| 1.0 mg/kg | 18 ± 4.2% | −6 ± 4% |
| 2.0 mg/kg | 25 ± 3.6% | −12 ± 5% |
| QR01029 | | |
| 0.5 mg/kg | 12 ± 2.1% | −4 ± 3% |
| 1.0 mg/kg | 15 ± 4.3% | −5 ± 2% |
| 2.0 mg/kg | 24 ± 5.2% | −8 ± 2% |
| QR01030 | | |
| 0.5 mg/kg | 18 ± 2.0% | −12 ± 6% |
| 1.0 mg/kg | 25 ± 3.6% | −20 ± 6% |
| 2.0 mg/kg | 30 ± 4.6% | −18 ± 7% |
| QR01031 | | |
| 0.5 mg/kg | 18 ± 3.5% | −11 ± 5% |
| 1.0 mg/kg | 25 ± 5.7% | −18 ± 6% |
| 2.0 mg/kg | 32 ± 2.6% | −17 ± 5% |
| QR01032 | | |
| 0.5 mg/kg | 20 ± 4.1% | −8 ± 6% |
| 1.0 mg/kg | 28 ± 3.1% | −9 ± 4% |
| 2.0 mg/kg | 35 ± 4.6% | −9 ± 5% |
| QR01033 | | |
| 0.5 mg/kg | 19 ± 2.1% | −8 ± 2% |
| 1.0 mg/kg | 26 ± 3.7% | −15 ± 6% |
| 2.0 mg/kg | 32 ± 4.0% | −19 ± 7% |
| QR01034 | | |
| 0.5 mg/kg | 23 ± 1.9% | −12 ± 8% |
| 1.0 mg/kg | 36 ± 4.8% | −15 ± 7% |
| 2.0 mg/kg | 45 ± 6.0% | −21 ± 7% |
| QR01035 | | |
| 0.5 mg/kg | 20 ± 3.1% | −14 ± 6% |
| 1.0 mg/kg | 28 ± 4.5% | −23 ± 6% |
| 2.0 mg/kg | 36 ± 4.6% | −26 ± 5% |
| QR01036 | | |
| 0.5 mg/kg | 19 ± 3.5% | −12 ± 9% |
| 1.0 mg/kg | 38 ± 4.2% | −18 ± 7% |
| 2.0 mg/kg | 46 ± 5.0% | −25 ± 7% |

Conclusion:

in the hypertensive animal model of renal artery-ligated rat, all the test compounds as prepared in the invention exhibited blood pressure reduction effects in different levels, in which the blood pressure reduction effects of the QR-01005, QR-01009, QR-01017, QR01019, QR01020, QR01023, QR01034 and QR01036 were obviously superior to that of the Azilsartan medoxomil positive drug, and the lasting time of the pressure blood reduction effect was close to that of Azilsartan medoxomil. At 24 hours after the administration, the blood pressure reduction of the Azilsartan medoxomil positive drug was 20%, while the QR-01005 was 21%, the QR01009 was 25%, the QR01017 was 20%, the QR01019 was 26%, the QR01020 was 15%, the QR01023 was 18%, the QR01034 was 25%, and the QR01036 was 24%, and thus the blood pressure reduction was close to that of Azilsartan medoxomil. In a safe dosage range, the maximum blood pressure reduction effects of the other compounds, such as QR01003, QR01008, QR01011, QR01021, QR01032 and QR01035, were close to that of Azilsartan medoxomil. In addition, since high blood pressure usually caused the increase of high heart rate by 20-50%, all the test compounds as prepared in the invention can have certain reduction effects on the heart rate of renal artery-ligated rats. This demonstrates that, in addition to significant blood pressure reduction effect, these compounds even have the effect of reducing heart rate to an extent.

2. Effect on Reducing Blood Pressure of Spontaneously Hypertensive Rats (SHR) by Multiple Oral Administrations of Benzimidazole Derivatives Male SHR (provided by Beijing Vital River Laboratory Animal Technology Co., Ltd., Beijing), aged with 40 weeks, weighted of 250 to 300 g, were randomly classified into 5 groups, including negative control group (0.5% CMC-Na), positive control group (Azilsartan medoxomil as a positive drug, synthesized by Wuhan Qirui Pharmaceuticals Optics Valley Biolake Development Center, Pharmaceutical Chemical Department) and three groups with the test compounds QR01002-QR01036 in low, middle, and high dosages (all drugs were formulated in 0.5% CMC-Na), 4-5 animals per group. The rats were administrated once per day, and the administration continued for 14 days. At 1 hour after the administration, the blood pressure and heart rate were measured. Before measuring blood pressure, the rat tails were heated by using a cyclic water bath tail sleeve at 39° C. to expand tail vessel, and thereafter, a tail sleeve method (BP2010A noninvasive blood pressure meter, Beijing Jiandeer Technology Limited Corporation, No. 1, Shangdi 10th Street, Haidian District, Beijing) was used to measure the blood pressures and heart rates of the rats, and each time point was measured three times to take the mean value. Maximum Blood pressure reduction (%)=maximum blood pressure reduction value after the administration/blood pressure value before the administration*100%.

TABLE 2

Effects on reducing blood pressure of spontaneously hypertensive rats (SHR) by oral administrations of benzimidazole derivatives

| Compound | Maximum blood pressure reduction | | |
|---|---|---|---|
| | $1^{st}$-day Administration | $7^{th}$-day administration | $14^{th}$-day administration |
| Negative control, 0.5 CMC-Na, 1.0 ml/kg | 8 ± 2.4% | 6.8 ± 2.1% | 7.5 ± 2.5% |
| Azilsartan medoxomil, 1.0 mg/kg | 32 ± 3.5% | 34 ± 2.8% | 36 ± 3.6% |
| QR01003 | | | |
| 0.5 mg/kg | 18 ± 4.6% | 21 ± 6.3% | 17 ± 6.8% |
| 1.0 mg/kg | 31 ± 6.8% | 35 ± 7.3% | 36 ± 8.1% |
| 2.0 mg/kg | 39 ± 5.0% | 41 ± 5.7% | 44 ± 6.1% |
| QR01005 | | | |
| 0.5 mg/kg | 16 ± 4.8% | 18 ± 5.2% | 21 ± 3.9% |
| 1.0 mg/kg | 38 ± 3.7% | 40 ± 6.2% | 42 ± 6.1% |
| 2.0 mg/kg | 45 ± 4.8% | 41 ± 6.2% | 45 ± 7.2% |
| QR01009 | | | |
| 0.5 mg/kg | 24 ± 6.8% | 28 ± 5.3% | 25 ± 4.9% |
| 1.0 mg/kg | 42 ± 6.3% | 41 ± 5.9% | 45 ± 6.7% |
| 2.0 mg/kg | 45 ± 5.6% | 48 ± 4.6% | 43 ± 7.2% |
| QR01013 | | | |
| 0.5 mg/kg | 14 ± 5.9% | 15 ± 7.1% | 17 ± 5.8% |
| 1.0 mg/kg | 24 ± 5.8% | 28 ± 6.0% | 27 ± 6.4% |
| 2.0 mg/kg | 34 ± 5.9% | 38 ± 5.7% | 39 ± 7.1% |

TABLE 2-continued

Effects on reducing blood pressure of spontaneously hypertensive rats (SHR) by oral administrations of benzimidazole derivatives

| Compound | Maximum blood pressure reduction | | |
|---|---|---|---|
| | $1^{st}$-day Administration | $7^{th}$-day administration | $14^{th}$-day administration |
| QR01017 | | | |
| 0.5 mg/kg | 22 ± 5.0% | 22 ± 3.3% | 23 ± 3.9% |
| 1.0 mg/kg | 34 ± 4.4% | 35 ± 3.9% | 36 ± 3.2% |
| 2.0 mg/kg | 36 ± 4.5% | 38 ± 2.1% | 38 ± 3.6% |
| QR01019 | | | |
| 0.5 mg/kg | 16 ± 6.2% | 15 ± 7.9% | 18 ± 4.5% |
| 1.0 mg/kg | 36 ± 6.3% | 38 ± 4.6% | 35 ± 6.7% |
| 2.0 mg/kg | 42 ± 4.8% | 46 ± 6.7% | 48 ± 8.6% |
| QR01020 | | | |
| 0.5 mg/kg | 19 ± 6.8% | 18 ± 6.9% | 21 ± 4.6% |
| 1.0 mg/kg | 30 ± 5.5% | 32 ± 8.3% | 35 ± 6.2% |
| 2.0 mg/kg | 36 ± 5.3% | 42 ± 7.5% | 43 ± 7.0% |
| QR01021 | | | |
| 0.5 mg/kg | 23 ± 6.4% | 24 ± 4.1% | 25 ± 5.0% |
| 1.0 mg/kg | 42 ± 7.7% | 40 ± 3.8% | 44 ± 5.1% |
| 2.0 mg/kg | 44 ± 6.0% | 44 ± 8.7% | 46 ± 5.9% |
| QR01023 | | | |
| 0.5 mg/kg | 25 ± 8.2% | 24 ± 7.1% | 25 ± 6.8% |
| 1.0 mg/kg | 39 ± 6.0% | 38 ± 7.0% | 42 ± 5.3% |
| 2.0 mg/kg | 45 ± 7.3% | 48 ± 9.5% | 40 ± 8.2% |
| QR01034 | | | |
| 0.5 mg/kg | 25 ± 8.1% | 28 ± 7.4% | 26 ± 5.1% |
| 1.0 mg/kg | 39 ± 7.5% | 39 ± 6.8% | 42 ± 5.9% |
| 2.0 mg/kg | 44 ± 8.6% | 45 ± 7.0% | 46 ± 7.3% |
| QR01036 | | | |
| 0.5 mg/kg | 20 ± 5.3% | 24 ± 8.6% | 24 ± 5.9% |
| 1.0 mg/kg | 35 ± 7.8% | 35 ± 4.6% | 40 ± 7.8% |
| 2.0 mg/kg | 46 ± 9.2% | 45 ± 8.3% | 48 ± 7.2% |

TABLE 3

Effect on reducing heart rate of spontaneously hypertensive rats (SHR) by oral administrations of benzimidazole derivatives

| Compound | Heart Rate |
|---|---|
| Negative control, 0.5 CMC-Na, 1.0 ml/kg | 6 ± 4% |
| Azilsartan medoxomil, 1.0 mg/kg | 8 ± 3% |
| QR01005 | |
| 5 mg/kg | 18 ± 5% |
| 1.0 mg/kg | 23 ± 6% |
| 2.0 mg/kg | 21 ± 4% |
| QR01009 | |
| 0.5 mg/kg | 23 ± 3% |
| 1.0 mg/kg | 24 ± 2% |
| 2.0 mg/kg | 27 ± 5% |
| QR01017 | |
| 0.5 mg/kg | 18 ± 5% |
| 1.0 mg/kg | 24 ± 4% |
| 2.0 mg/kg | 29 ± 6% |
| QR01019 | |
| 0.5 mg/kg | 20 ± 6% |
| 1.0 mg/kg | 18 ± 4% |
| 2.0 mg/kg | 29 ± 2% |

TABLE 3-continued

Effect on reducing heart rate of spontaneously hypertensive rats (SHR) by oral administrations of benzimidazole derivatives

| Compound | Heart Rate |
|---|---|
| QR01020 | |
| 0.5 mg/kg | 16 ± 4% |
| 1.0 mg/kg | 25 ± 3% |
| 2.0 mg/kg | 18 ± 5% |
| QR01023 | |
| 0.5 mg/kg | 20 ± 3% |
| 1.0 mg/kg | 14 ± 4% |
| 2.0 mg/kg | 23 ± 5% |
| QR01034 | |
| 0.5 mg/kg | 19 ± 2% |
| 1.0 mg/kg | 15 ± 4% |
| 2.0 mg/kg | 21 ± 3% |
| QR01036 | |
| 0.5 mg/kg | 14 ± 4% |
| 1.0 mg/kg | 25 ± 2% |
| 2.0 mg/kg | 21 ± 3% |

Conclusion:

in the animal model of spontaneously hypertensive rat, all the test compounds as prepared in the invention exhibited blood pressure reduction effects, in which the blood pressure reduction effects of the QR-01005, QR-01009, QR01019, QR01021, QR01023, QR01034, QR01034 and QR01036 were obviously superior to that of the Azilsartan medoxomil positive drug. After long-term administration, the blood pressure reduction effects of the compounds were stable, and the states of the corresponding animals were superior to the group of the animals administrated with Azilsartan medoxomil. In the range of safe dosages, the blood pressure reduction effect of the other compounds was comparable to that of Azilsartan medoxomil. During the whole administration, the compounds QR01005, QR01009, QR01017, QR01019, QR01020, QR01023, QR01034, and QR01036 as prepared in the invention can exhibit significant reduction effects on the heart rate of SHR rats to a certain extent, and this shows that the compounds, in addition to significant blood pressure reduction, even have better effect of reducing heart rate.

3. Effect on Blood Pressure of Normal Rats by Single Oral Administration of Benzimidazole Derivatives Wistar rats (provided by Hubei Province Disease Prevention Control Center, Wuhan, Hubei), male, weighted of 200 to 200 g, are randomly classified into 5 groups, including negative control group (0.5% CMC-Na, 1.0 ml/kg), positive control group (Azilsartan medoxomil as a positive drug, synthesized by Wuhan Qirui Pharmaceuticals Optics Valley Biolake Development Center, Pharmaceutical Chemical Department) and three groups with the test compounds QR01002-QR01036 in low, middle, and high dosages (0.5, 1.0, 2.0 mg/kg, p.o., all drugs were formulated in 0.5% CMC-Na), 8-10 animals per group. Before measuring blood pressure, the rat tails were heated by using a cyclic water bath tail sleeve at 39° C. to expand tail vessel, and thereafter, a tail sleeve method (BP2010A noninvasive blood pressure meter, Beijing Jiandeer Technology Limited Corporation, No. 1, Shangdi 10th Street, Haidian District, Beijing) was used to measure the blood pressures and heart rates of the rats before the administrations and at 0.5, 1, 2, 4, and 8 hours after oral administration, and each of the time points was measured three times to take the mean value.

TABLE 4

Effects on reducing blood pressure of normal rats by oral administration of benzimidazole derivatives QR01002-QR01036 and positive drugs

| Compound | blood pressure reduction at 8 h after the administration | variations on heart rate |
|---|---|---|
| Negative control | 5.2 ± 3.1% | −6 ± 7% |
| Azilsartan medoxomil, 1.0 mg/kg | 6.4 ± 2.1% | −5 ± 2% |
| QR01002 | | |
| 0.5 mg/kg | 5.6 ± 2.3% | −4 ± 5% |
| 1.0 mg/kg | 6.4 ± 2.1% | −5 ± 4% |
| 2.0 mg/kg | 6.4 ± 2.1% | +5 ± 6% |
| QR01003 | | |
| 0.5 mg/kg | 5.6 ± 3.1% | −2 ± 2% |
| 1.0 mg/kg | 5.4 ± 1.9% | +4 ± 3% |
| 2.0 mg/kg | 6.4 ± 3.4% | −3 ± 4% |
| QR01004 | | |
| 0.5 mg/kg | 7.5 ± 1.4% | −1 ± 2% |
| 1.0 mg/kg | 6.7 ± 1.3% | −2 ± 1% |
| 2.0 mg/kg | 5.7 ± 2.6% | +3 ± 2% |
| QR01005 | | |
| 0.5 mg/kg | 6.3 ± 1.3% | −3 ± 1% |
| 1.0 mg/kg | 3.6 ± 2.1% | −6 ± 6% |
| 2.0 mg/kg | 4.8 ± 2.3% | +8 ± 4% |
| QR01006 | | |
| 0.5 mg/kg | 6.3 ± 2.8% | −3 ± 4% |
| 1.0 mg/kg | 7.2 ± 1.9% | +2 ± 1% |
| 2.0 mg/kg | 4.2 ± 2.1% | −5 ± 6% |
| QR01007 | | |
| 0.5 mg/kg | 3.5 ± 3.4% | −3 ± 2% |
| 1.0 mg/kg | 2.5 ± 4.6% | −7 ± 2% |
| 2.0 mg/kg | 3.7 ± 4.3% | +5 ± 4% |
| QR01008 | | |
| 0.5 mg/kg | 4.5 ± 2.7% | −6 ± 2% |
| 1.0 mg/kg | 4.6 ± 2.5% | +4 ± 2% |
| 2.0 mg/kg | 2.1 ± 2.4% | −2 ± 3% |
| QR01009 | | |
| 0.5 mg/kg | 3.1 ± 2.4% | −5 ± 2% |
| 1.0 mg/kg | 5.6 ± 1.9% | +4 ± 5% |
| 2.0 mg/kg | 4.8 ± 5.8% | −8 ± 5% |
| QR01010 | | |
| 0.5 mg/kg | 2.1 ± 3.2% | +5 ± 3% |
| 1.0 mg/kg | 4.6 ± 4.7% | −5 ± 1% |
| 2.0 mg/kg | 5.7 ± 2.3% | −4 ± 5% |
| QR01011 | | |
| 0.5 mg/kg | 2.7 ± 3.6% | −3 ± 5% |
| 1.0 mg/kg | 3.8 ± 2.1% | +6 ± 3% |
| 2.0 mg/kg | 3.7 ± 5.0% | −5 ± 3% |
| QR01012 | | |
| 0.5 mg/kg | 1.9 ± 3.2% | +1 ± 3% |
| 1.0 mg/kg | 3.9 ± 2.1% | −3 ± 2% |
| 2.0 mg/kg | 4.6 ± 2.4% | −3 ± 4% |
| QR01013 | | |
| 0.5 mg/kg | 4.2 ± 2.7% | −3 ± 4% |
| 1.0 mg/kg | 6.2 ± 2.3% | +5 ± 2% |
| 2.0 mg/kg | 3.4 ± 4.2% | −5 ± 4% |
| QR01014 | | |
| 0.5 mg/kg | 2.9 ± 3.4% | −4 ± 2% |
| 1.0 mg/kg | 2.7 ± 3.6% | −3 ± 3% |
| 2.0 mg/kg | 4.6 ± 3.2% | +4 ± 5% |

TABLE 4-continued

Effects on reducing blood pressure of normal rats by oral administration of benzimidazole derivatives QR01002-QR01036 and positive drugs

| Compound | blood pressure reduction at 8 h after the administration | variations on heart rate |
|---|---|---|
| QR01015 | | |
| 0.5 mg/kg | 3.7 ± 2.6% | +3 ± 2% |
| 1.0 mg/kg | 2.3 ± 1.8% | +1 ± 2% |
| 2.0 mg/kg | 1.8 ± 2.4% | −3 ± 3% |
| QR01016 | | |
| 0.5 mg/kg | 3.6 ± 2.8% | +1 ± 2% |
| 1.0 mg/kg | 4.2 ± 5.7% | +5 ± 4% |
| 2.0 mg/kg | 5.9 ± 3.2% | +3 ± 2% |
| QR01017 | | |
| 0.5 mg/kg | 2.9 ± 4.5% | −5 ± 2% |
| 1.0 mg/kg | 3.3 ± 4.1% | −2 ± 4% |
| 2.0 mg/kg | 5.1 ± 3.2% | −4 ± 3% |
| QR01019 | | |
| 0.5 mg/kg | 2.4 ± 3.0% | −5 ± 5% |
| 1.0 mg/kg | 4.2 ± 3.5% | −4 ± 6% |
| 2.0 mg/kg | 4.5 ± 6.5% | +8 ± 3% |
| QR01020 | | |
| 0.5 mg/kg | 2.8 ± 5.3% | −1 ± 4% |
| 1.0 mg/kg | 3.9 ± 4.3% | −7 ± 3% |
| 2.0 mg/kg | 5.6 ± 3.2% | +3 ± 2% |
| QR01021 | | |
| 0.5 mg/kg | 2.7 ± 3.2% | −4 ± 3% |
| 1.0 mg/kg | 3.9 ± 3.8% | −2 ± 5% |
| 2.0 mg/kg | 2.8 ± 3.1% | −1 ± 3% |
| QR01023 | | |
| 0.5 mg/kg | 5.3 ± 1.4% | −3 ± 2% |
| 1.0 mg/kg | 3.6 ± 6.1% | +6 ± 3% |
| 2.0 mg/kg | 4.3 ± 2.1% | −3 ± 5% |
| QR01025 | | |
| 0.5 mg/kg | 3.3 ± 3.2% | −2 ± 3% |
| 1.0 mg/kg | 6.2 ± 3.8% | +6 ± 5% |
| 2.0 mg/kg | 3.7 ± 4.1% | −3 ± 4% |
| QR01026 | | |
| 0.5 mg/kg | 5.2 ± 3.2% | −5 ± 8% |
| 1.0 mg/kg | 4.3 ± 5.1% | −3 ± 7% |
| 2.0 mg/kg | 3.8 ± 4.5% | −4 ± 7% |
| QR01027 | | |
| 0.5 mg/kg | 5.2 ± 3.0% | −3 ± 4% |
| 1.0 mg/kg | 4.8 ± 4.2% | +5 ± 2% |
| 2.0 mg/kg | 2.8 ± 3.9% | −3 ± 4% |
| QR01028 | | |
| 0.5 mg/kg | 1.7 ± 5.3% | −4 ± 3% |
| 1.0 mg/kg | 3.9 ± 5.2% | −3 ± 4% |
| 2.0 mg/kg | 2.5 ± 4.6% | −2 ± 3% |
| QR01029 | | |
| 0.5 mg/kg | 4.2 ± 3.2% | −3 ± 1% |
| 1.0 mg/kg | 5.8 ± 2.2% | −4 ± 5% |
| 2.0 mg/kg | 3.4 ± 4.8% | +4 ± 5% |
| QR01030 | | |
| 0.5 mg/kg | 2.9 ± 3.0% | −2 ± 4% |
| 1.0 mg/kg | 5.2 ± 4.3% | +4 ± 2% |
| 2.0 mg/kg | 3.7 ± 5.8% | −3 ± 5% |
| QR01031 | | |
| 0.5 mg/kg | 2.9 ± 2.6% | −5 ± 5% |
| 1.0 mg/kg | 4.5 ± 3.8% | −4 ± 3% |
| 2.0 mg/kg | 4.7 ± 3.1% | −8 ± 4% |
| QR01032 | | |
| 0.5 mg/kg | 4.7 ± 3.1% | −8 ± 6% |
| 1.0 mg/kg | 5.2 ± 2.7% | −5 ± 2% |
| 2.0 mg/kg | 4.8 ± 3.6% | −3 ± 5% |
| QR01033 | | |
| 0.5 mg/kg | 2.3 ± 3.2% | −3 ± 4% |
| 1.0 mg/kg | 6.4 ± 2.9% | −5 ± 3% |
| 2.0 mg/kg | 4.2 ± 5.0% | −1 ± 7% |
| QR01034 | | |
| 0.5 mg/kg | 3.4 ± 2.6% | −2 ± 5% |
| 1.0 mg/kg | 5.1 ± 3.6% | +5 ± 8% |
| 2.0 mg/kg | 3.4 ± 5.0% | −2 ± 5% |
| QR01035 | | |
| 0.5 mg/kg | 6.4 ± 2.1% | −4 ± 3% |
| 1.0 mg/kg | 3.4 ± 2.5% | −3 ± 3% |
| 2.0 mg/kg | 6.1 ± 3.8% | +6 ± 5% |
| QR01036 | | |
| 0.5 mg/kg | 2.8 ± 2.1% | −1 ± 6% |
| 1.0 mg/kg | 5.2 ± 3.5% | −8 ± 2% |
| 2.0 mg/kg | 6.3 ± 2.0% | −5 ± 5% |

Results and Conclusions: the three dosages of all the test compounds as prepared in the invention (0.5, 1.0 and 2.0 mg/kg, p.o., formulated in 0.5% CMC-Na) did not significant effects on the blood pressure and heart rate of normal rats, and this shows that the kind of the compounds do not significant effects on normal blood pressure and heart rate.

4. Effect on Reducing Blood Pressure of Renovascular Hypertensive Rats by Single Oral Administration of Potassium Salt of QR01019

Wistar rats (provided by Hubei Province Disease Prevention Control Center, Wuhan, Hubei), male, weighted of 180 to 200 g, are randomly classified into 5 groups, including negative control group (0.5% CMC-Na), positive control group (1.0 mg/kg of potassium salt of Azilsartan medoxomil as the positive drug) and three groups with the test compound, QR01019 potassium salt (1.0 mg/kg), 6-8 animals per group. The unilateral renal artery of the rates were ligated to form two-kidney, one-clip renovascular hypertensive rat (RHR) models. After the surgery, the blood pressure was measured for weekly, and the measurement continued for 4 weeks. The rats whose blood pressures were steadily elevated by 4 kPa were successfully modeled rats. Before measuring blood pressure, the rat tails were heated by using a cyclic water bath tail sleeve at 39° C. to expand tail vessel, and thereafter, a tail sleeve method (BP2010A noninvasive blood pressure meter, Beijing Jiandeer Technology Limited Corporation, No. 1, Shangdi 10th Street, Haidian District, Beijing) was used to measure the blood pressures and heart rates of the rats before the administrations and at 1, 3, 5, 7, and 10 hours after oral administration, and each of the time points was measured three times to take the mean value. Maximum Blood pressure reduction (%)=maximum blood pressure reduction value after the administration/blood pressure value before the administration*100%.

5. Effect on Reducing Blood Pressure of Renovascular Hypertensive Rats by Oral Administration of Potassium Salt of QR01019 and Positive Drugs

| Compound | Maximum blood pressure reduction | Variations on heart rate |
| --- | --- | --- |
| Negative control | 4.6 ± 1.2% | −8 ± 3% |
| Positive control | 34 ± 3.6% | −14 ± 7% |
| QR01019 potassium salt | 38 ± 4.3% | −18 ± 5% |

Results and conclusions: the potassium salt of the test compound QR01019 as prepared in the invention can have significant blood pressure reduction effect at the same dosage as compared with control group, and its regulation on the heart rate is obviously superior to the positive control group.

At last, it should be noted that the above examples are only used for illustrating the technical solution of the invention, but not for limiting it. Although the invention is described in detail by referring to the preceding examples, a person skilled in the art should understand that the technical solutions as recited in the preceding examples can still be amended or a part or all technical features therein may be equivalently substituted. These amendments or substitutions cannot make the nature of the corresponding technical solution away from the scope as covered by the technical solution in each example.

What is claimed is:

1. A compound of general formula I and pharmaceutically acceptable salts thereof,

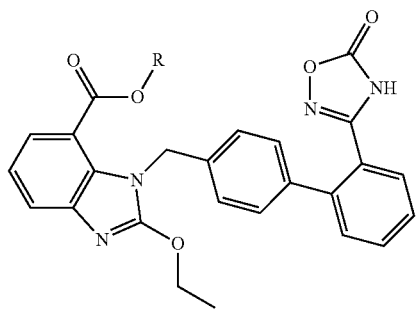

I wherein
R in the formula I represents

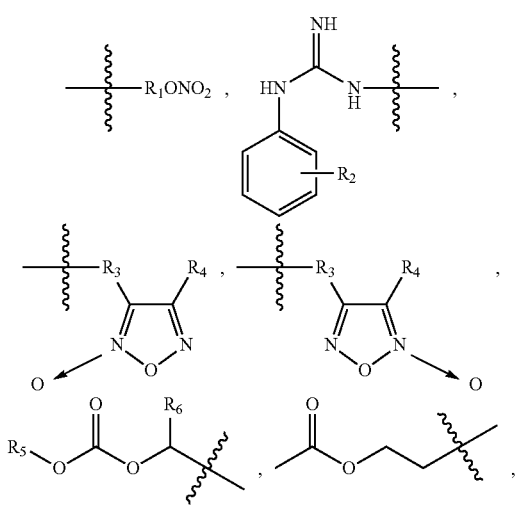

wherein a=0, 1, 2, 3, 4, 5 or 6;

$R_1$ represents $C_2$-$C_8$ alkyl, $C_2$-$C_8$ alkenyl, $C_2$-$C_8$ alkynyl,

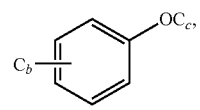

$(CH_2)_nO(CH_2)_m$,

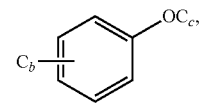

phenyl, substituted phenyl, aromatic heterocycle or substituted aromatic heterocycle, where in

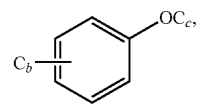

b, c=0, 1, 2, 3, 4, 5 or 6; in $(CH_2)_nO(CH_2)_m$, n, m=1, 2, 3, 4, 5 or 6;

$R_2$ represents hydrogen, halogens, trifluoromethyl, $C_1$-$C_8$ alkoxy, $C_1$-$C_8$ alkyl, nitro, sulfonamido, amino or cyano;

$R_3$ represents $C_1$-$C_8$ alkylidene, $C_1$-$C_8$ alkoxy, $C_2$-$C_8$ alkenyloxy, $C_2$-$C_8$ alkynyloxy, $(C_1$-$C_6)O(C_1$-$C_6)$,

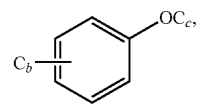

phenyl, substituted phenyl, aromatic heterocycle or substituted aromatic heterocycle, where in

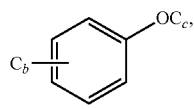

b, c=0, 1, 2, 3, 4, 5 or 6;

- $R_4$ represents a phenyl, substituted phenyl, benzene sulphonyl, 5- to 6-membered aromatic heterocycle, substituted 5- to 6-membered aromatic heterocycle, cyano, trifluoromethyl, $C_1$-$C_8$ alkyoxy, $C_1$-$C_8$ nitrate ester group or $C_1$-$C_8$ alkyl;
- $R_5$ represents phenyl, substituted phenyl, 5- to 6-membered aromatic heterocycle, substituted 5- to 6-membered aromatic heterocycle, cyano, trifluoromethyl, $C_1$-$C_8$ alkoxy, $C_1$-$C_8$ nitrate ester group, $C_1$-$C_8$ alkyl, $C_2$-$C_8$ alkenyl, $C_2$-$C_8$ alknyl,

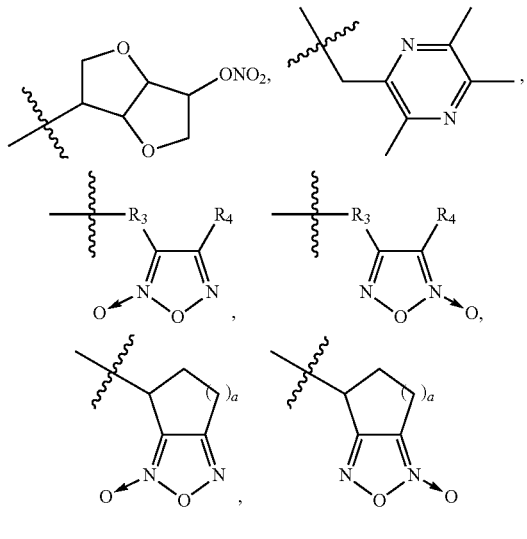

or $(CH_2)_nO(CH_2)_m$;

- $R_6$ and $R_7$ independently represent hydrogen, $C_1$-$C_8$ alkoxy or $C_1$-$C_8$ alkyl;
- $R_8$ and $R_9$ independently represent hydrogen, $C_1$-$C_8$ alkoxy, $C_1$-$C_8$ nitrate ester group or $C_1$-$C_8$ alkyl;
- wherein the substituted phenyl is a phenyl which is substituted with one or more substituents selected from the group consisting of hydroxyl, $C_1$-$C_6$ alkyl, $C_1$-$C_6$ alkoxy, halogens, nitro, amino, cyano, trifluoromethyl, and —CH=CHCO$_2$R$_{11}$, wherein the substituents are same or different, wherein $R_{11}$ represents hydrogen or $C_1$-$C_6$ alkyl;
- the aromatic heterocycle is a 5 to 7-membered aromatic cycle containing 1 to 4 heteroatoms, the heteroatoms are independently selected from the group consisting of O, S, and N;
- the substituted aromatic heterocycle is optionally substituted with one or more substituents selected from the group consisting of $C_1$-$C_6$ alkyl, $C_1$-$C_6$ alkoxy, halogen, wherein the substituents are same or different.

2. The compound and pharmaceutically acceptable salts of claim 1, wherein R represents

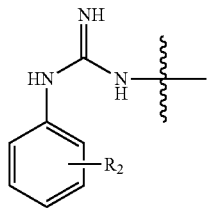

and $R_2$ is a meta- or para-substituent.

3. The compound and pharmaceutically acceptable salts of claim 1, wherein R represents

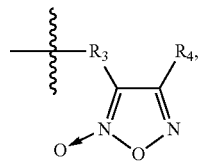

$R_3$ represents $C_1$-$C_8$ alkylidene, and $R_4$ represents a phenyl, or a substituted phenyl at meta- or para-position.

4. The compound and pharmaceutically acceptable salts of claim 1, wherein R represents

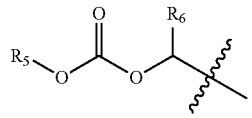

$R_5$ represents

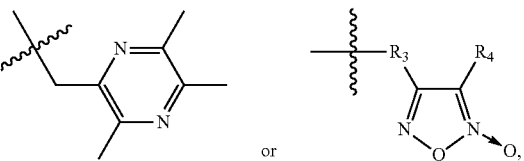

and $R_6$ represents hydrogen or $C_1$-$C_8$ alkyl.

5. The compound and pharmaceutically acceptable salts of claim 4, wherein $R_3$ represents $C_1$-$C_8$ alkylidene.

6. The compound and pharmaceutically acceptable salts of claim 1, wherein R represents

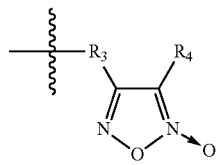

$R_3$ represents $C_1$-$C_8$ alkylidene, and $R_4$ represents $C_1$-$C_8$ alkyl, $C_1$-$C_8$ nitrate ester, or cyano.

7. The compound and pharmaceutically acceptable salts of claim 1, wherein the compound is
(4-phenyl-1,2,5-oxadiazole-2-oxide-3-)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

(3,5,6-trimethylpyrazine-2-methoxy-carbonyloxy)
methyl-2-ethoxy-1-{[2'-(5-oxo-4,5-dihydro-1,2,4-oxadiazole)-3-yl)biphenyl-4-yl]methyl}-1H-benzimidazole-7-carboxylate;

1-(3,5,6-trimethylpyrazine-2-methoxy-carbonyloxy)
ethyl-2-ethoxy-1-{[2'-(5-oxo-4,5-dihydro-1,2,4-oxadiazole)-3-yl)biphenyl-4-yl]methyl}-1H-benzimidazole-7-carboxylate;

(3-methyl-1,2,5-oxadiazole-2-oxide-3-methoxy-carbonyloxy)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

1-(3-methyl-1, 2,5-oxadiazole-2-oxide-3-methoxy-carbonyloxy)ethyl-2-ethoxy-1-{[2'-(5-oxo-4,5-dihydro-1,2,4-oxadiazole)-3-yl)biphenyl-4-yl]methyl}-1H-benzimidazole-7-carboxylate;

4-(3-methyl-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate;

4-(3-nitratemethyl-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate; or 4-(3-cyano-1,2,5-oxadiazole-2-oxide)methyl-2-ethoxy-1-{[2'-(5-oxo-4,5-dihydro-1,2,4-oxadiazole)-3-yl)biphenyl-4-yl]methyl}-1H-benzimidazole-7-carboxylate.

8. The compound and pharmaceutically acceptable salts of claim 1, wherein the pharmaceutically acceptable salt is a potassium salt.

9. The compound and pharmaceutically acceptable salts of claim 8, wherein the pharmaceutically acceptable salt is a salt of formula II:

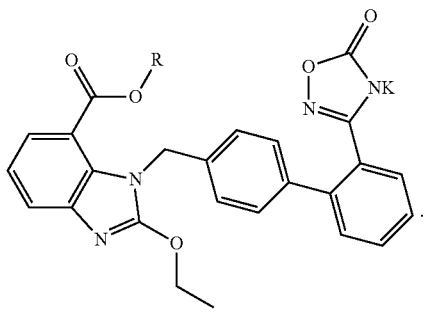

10. A process for manufacturing the compound of claim 1, comprising:
reacting Azilsartan with an acylating agent in the presence of an alkali to produce a mixed acid anhydride, and reacting the mixed acid anhydride with an alcohol having a structure of R—OH in the presence of an alkali, wherein R is defined in claim 1.

11. A process for manufacturing the compound of claim 1, comprising:
reacting Azilsartan with an alkylating agent having a structure of R—X, wherein X is a halogen atom, in the presence of an alkali, wherein R is defined in claim 1.

12. A process for manufacturing the compound of claim 1, comprising an esterification step of Azilsartan and an alcohol having a structure of R—OH in the presence of a condensation agent, wherein R is defined in claim 1.

13. The process according to claim 12, wherein the alcohol having the structure of R—OH is a diol and R represents $-R_1ONO_2$ and after esterification of the diol and Azilsartan to produce a monoester, reacting the monoester with fuming nitric acid.

14. The process according to claim 12, wherein the alcohol having the structure of R—OH is N-aryl-N'-hydroxyguanidine, wherein R represents

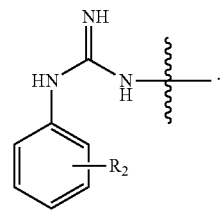

15. A process of manufacturing the compound of claim 1, characterized in that the process comprises the step of reacting Azilsartan with furazan oxynitride NO donors in the presence of an alkali catalyst of DCC/DMAP or Et$_3$N/N-methylpyrrolidone, in which R represents

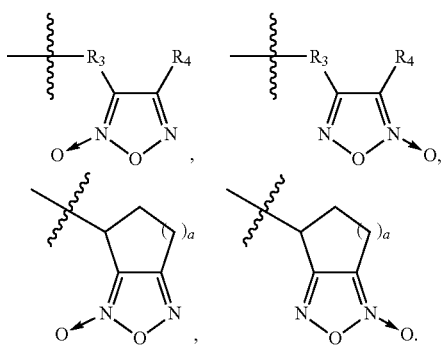

16. A process of manufacturing the pharmaceutically acceptable salt of the formula II according to claim 9, comprising:
dissolving the compound of claim 1 in a solvent;
adding a potassium salt to the solvent;
refluxing the solvent; and
cooling the solvent and precipitating crystals from the solvent, wherein the solvent is selected from the group consisting of ether solvents, ketone solvents, alcohol solvent, ester solvents, alkane solvents, aromatic hydrocarbon solvents, nitrile solvents and combinations thereof.

17. A pharmaceutical composition, characterized in that the pharmaceutical composition comprises a therapeutically effective amount of the compound of claim 1, or a pharmaceutically acceptable salt thereof, and a pharmaceutically acceptable adjuvant.

18. A method of treating a cardiovascular disease, comprising the step of administrating the pharmaceutical composition according to claim 17 to a patient in need thereof, wherein the cardiovascular disease is hypertension or high heart rate caused by hypertension.

19. The process according to claim 10, wherein the acylating agent is paramethybenzenesulfonyl chloride, and the alkali is potassium carbonate/N,N-dimethylpyridylamine.

20. The process according to claim 11, wherein the alkali is Et$_3$N/N-methypyrrolidone and the alkylating agent is prepared by reacting chloromethyl chloroformate or 2-chloro-ethyl chloroformate with an alcohol a structure of R—OH.

21. The process according to claim 12, wherein the condensation agent is DCC/DMAP.

22. The process according to claim 12, where the alcohol having the structure of R—OH is a halogenated alcohol, and after the halogenated alcohol and Azilsartan take the esterification to produce an ester, further reacting the ester with silver nitrate, wherein R represents -$\xi$-R$_1$ONO$_2$.

* * * * *